(12) United States Patent
Dasseux et al.

(10) Patent No.: US 6,734,169 B2
(45) Date of Patent: May 11, 2004

(54) APOLIPOPROTEIN A-I AGONISTS AND THEIR USE TO TREAT DYSLIPIDEMIC DISORDERS

(75) Inventors: Jean-Louis Dasseux, Mannheim (DE); Renate Sekul, Wichernstr. 13, Ladenburg (DE), D-68526; Klaus Büttner, Eichendorffstr. 6, Epfenbach (DE), D-68535; Isabelle Cornut, Meisenweg 10, Edingen-Neckarhausen (DE), 98535; Günther Metz, Lessingstr. 14, Edingen-Necharhausen (DE), 68535

(73) Assignees: Jean Louis Dasseux, Brighton, MI (US); Renate Sekul, Ladenburg (DE); Klaus Buttner, Epfenbach (DE); Isabelle Cornut, Cry (FR); Gunther Metz, Heidelberg (DE); Jean DuFourcq, Pessac (FR)

( * ) Notice: Subject to any disclaimer, the term of this patent is extended or adjusted under 35 U.S.C. 154(b) by 169 days.

(21) Appl. No.: 09/865,989

(22) Filed: May 25, 2001

(65) Prior Publication Data

US 2004/0029807 A9 Feb. 12, 2004

Related U.S. Application Data

(63) Continuation of application No. 09/465,719, filed on Dec. 17, 1999, now Pat. No. 6,265,377, which is a continuation of application No. 08/940,093, filed on Sep. 29, 1997, now Pat. No. 6,037,323.

(51) Int. Cl.[7] .................... A61K 38/10; A61K 38/16; C07K 7/08; C07K 14/775

(52) U.S. Cl. ................ 514/12; 514/13; 514/14; 530/324; 530/326; 530/327

(58) Field of Search .............. 514/12, 13, 17; 530/324, 325, 326, 327

(56) References Cited

U.S. PATENT DOCUMENTS

| | | | |
|---|---|---|---|
| 4,229,360 A | 10/1980 | Schneider et al. | 424/450 |
| 4,411,894 A | 10/1983 | Schrank et al. | 514/221 |
| 4,643,988 A | 2/1987 | Segrest et al. | 514/12 |
| 4,857,319 A | 8/1989 | Crowe et al. | 424/94.1 |
| 4,880,635 A | 11/1989 | Janoff et al. | 424/450 |
| 6,004,925 A * | 12/1999 | Dasseux et al. | 514/2 |
| 6,037,323 A * | 3/2000 | Dasseux et al. | 514/12 |
| 6,265,377 B1 * | 7/2001 | Dasseux et al. | 514/12 |

FOREIGN PATENT DOCUMENTS

| | | |
|---|---|---|
| EP | 0 162 414 | 5/1985 |
| WO | WO 93/25581 | 12/1993 |
| WO | WO 94/13819 | 6/1994 |
| WO | WO 96/04916 | 2/1996 |
| WO | WO 96/37608 | 11/1996 |
| WO | WO-99/16459 A1 * | 4/1999 |

OTHER PUBLICATIONS

Anantharamaiah, 1986, *Methods in Enzymology* 128:627–647.
Anantharamaiah et al., 1985, *J. Biol. Chem.* 260:10248–10255.
Anantharamaiah et al., 1986, *Proteins of Biological Fluids* 34:63–66.
Anantharamaiah et al., 1990, *Arteriosclerosis* 10(10):95–105.
Anantharamaiah et al., 1991, *Adv. Exp. Med. Biol.* 285:131–140.

(List continued on next page.)

Primary Examiner—Jeffrey E. Russel
(74) Attorney, Agent, or Firm—Jones Day

(57) ABSTRACT

The present invention provides peptides and peptide analogues that mimic the structural and pharmacological properties of human ApoA-I. The peptides and peptide analogues are useful to treat a variety of disorders associated with dyslipidemia.

27 Claims, 11 Drawing Sheets

HELICAL WHEEL
PEPTIDE 210

OTHER PUBLICATIONS

Badimon et al., 1990, *J. Clin. Invest.* 85:1234–1241.
Barrans et al., 1996, *Biochim. Biophys. Acta* 1300:73–85.
Beitz et al., 1992, *Prostaglandins, Leukotrienes and Essential Fatty Acids* 47:149–152.
Berard et al., 1997, *Nature Medicine* 3(7):744–749.
Blondelle et al., 1993, *Biochim. Biophys. Acta* 1202:331–336.
Brasseur, 1991, *J. Biol. Chem.* 266(24):16120–16127.
Brasseur et al., 1990, *Biochim. Biophys. Acta* 1043:245–252.
Brasseur et al., 1993, *Biochim. Biophys. Acta* 1170:1–7.
Brouilette and Anantharamaiah, 1995, *Biochim. Biophys. Acta* 1256:103–129.
Burkey et al., 1992, *Circulation, Supplement 1* 86:1–472, Abstract No. 1876.
Burkey et al., 1995, *J. Lipid Res.* 36:1463–1473.
Cheung et al., 1991, Lipid Res. 32:383–394.
Chung et al., 1985, *J. Biol. Chem.* 260:10256–10262.
Collet et al., 1997, *Journal of Lipid Research* 38634–644.
Corijn et al., 1993, *Biochim. Biophys. Acta* 1170:8–16.
Cox et al., *The Interaction of Calmodulin with Amphipathic Peptides J. Biol. Chem.* 260(4):2527–2534.
Davidson et al., 1994, *J. Biol. Chem.* 269(37):22975–22982.
Davidson et al., 1996, *Proc. Natl. Acad. Sci. U.S.A.* 93:13605–13610.
Deamer et al., 1983, *Liposomes* (Ostro, Ed.), Marcel Dekker, Inc., New York.
Demoor et al., 1996, *24th European Chemical Peptide Symposium*.
Demoor et al., 1996, *Eur. J. Biochem.* 239:74–84.
Dufourcq et al., 1986, *Biochim. Biophys. Acta* 859:33–48.
Duverger, 1996, *Circulation* 94:713–717.
Duverger et al., 1996, *Arterioscler. Thromb. Vasc. Biol.* 16:1424–1429.
Emmanuel et al., 1994, *J. Biol. Chem.* 269(47):29883–29890.
Epand et al., 1987, *J. Biol. Chem.* 262:9389–9396.
Epand et al., 1995, *Biopolymers (Peptide Science)* 37:319–338.
Esposito et al., 1997, *Biopolymers* 41:27–35.
Fielding and Fielding, 1995, *J. Lipid Res.* 36:211–228.
Fournier et al., 1996, *J. Lipid Res.* 37:1704–1711.
Francone et al., 1995, *J. Clin. Invet.* 96:1440–1448.
Frank et al., 1997, *Biochemistry* 36:1789–1806.
Fruchart and Ailhaud, 1992, *Clin. Chem.* 38:793–797.
Fukushima et al., 1979, *J. Am. Chem. Soc.* 101(13):3703–3704.
Fukushima et al., 1980, *J. Biol. Chem.* 255:10651–10657.
Garber et al., 1992, *Arteriosclerosis and Thrombosis* 12:886–894.
Gordon et al., 1989, *Circulation* 79:8–15.
Gordon and Rifkind, 1989, *N. Eng. J. Med.* 321:1311–1316.
Groebke et al., 1996, *Proc. Natl. Acad. Sci. U.S.A.* 93:4025–4029.
Hirano et al., 1997, *Arterioscler. Thromb. Vasc. Biol.* 17(6):1053–1059.
Holvoet et al., 1995, *Biochemistry* 34:13334–13342.
Hope et al., 1986, *Chemistry and Physics of Lipids* 40:89–107.
Huyghues–Despointes et al., 1995, *Biochemistry* 34(41):13267–13271.
Ji and Jonas, 1995, *J. Biol. Chem.* 270:11290–11297.
Johnson et al., 1971, *Biochim. Biophys. Acta* 233:820.
Jonas, 1986, *Methods in Enzymol.* 128:553–582.
Jonas, 1992, "Lipid–Binding Properties of Apolipoproteins," In: *Structure and Function of Apolipoproteins*, CRC Press, Ch. 8, pp. 217–250.
Kaiser, 1970, *Anal. Biochem.* 34:595–598.
Kaiser and Kezdy, 1983, *Proc. Natl. Acad. Sci. U.S.A.* 80:1137–1143.
Kannelis et al., 1980, *J. Biol. Chem.* 255(3):11464–11472.
Koizumi et al., 1988, J. Lipid Res. 29:1405–1415.
Kneib–Cordonnier et al., 1990, *Int. J. Peptide Protein Res.* 35:527–538.
Knott et al., 1985, *Science* 230:37–43.
Labeur et al., 1997, *Arterioscler. Throm. Vasc. Biol.* 17:580–588.
Lacko and Miller, 1997, *J. Lip. Res.* 38:1267–1273.
Li et al., 1996, *Proc. Natl. Acad. Sci. U.S.A.* 93:6676–6681.
Lins et al., 1993, *Biochim. Biophys. Acta Biomembranes* 1151:137–142.
Liu et al., 1994, *J. Lipid Res.* 35:2263–2267.
Livingstone, 1974, *Methods in Enzymology: Immunoaffinity Chromatography of Proteins* 34:723–731.
Lund–Katz et al., 1990, *J. Biol. Chem.* 265(21):12217–12223.
Lund–Katz et al., 1995, *Biochemistry* 34:9219–9226.
Marqusee et al., 1987, *Proc. Natl. Acad. Sci. U.S.A.* 84(24):8898–8902.
Mendez et al., 1994, *J. Clin. Invest.* 94:1698–1705.
Mezdour et al., 1995, *Atherosclerosis* 113:237–246.
Miller, 1987, *Amer. Heart* 113:589–597.
Milner–White and Poet, 1987, *Trends Biochem. Sci.* 12:189–192.
Minnich et al., 1992, *J. Biol. Chem.* 267:16553–16560.
Mishra et al., 1994, *J. Biol. Chem.* 269(10):7185–7191.
Mishra et al., 1995, *J. Biol. Chem.* 270(4):1602–1611.
Nakagawa et al., 1985, *J. Am. Chem. Soc.* 107:7087–7092.
Nedelec et al., 1989, *Biochimie* 71:145–151.
Palgunachari et al., 1996, *Arterioscler. Thromb. Vasc. Biol.* 16:328–338.
Paszty et al., 1994, *J. Clin. Invest.* 94:899–903.
Plump et al., 1994, *Proc. Natl. Acad. Sci. U.S.A.* 91:9607–9611.
Ponsin et al., 1984, *Biochemistry* 23:5337–5342.
Ponsin et al., 1986, *J. Biol. Chem.* 261(20):9202–9205.
Pownall et al., 1980, *Proc. Natl. Acad. Sci. U.S.A.* 77(6):3154–3158.
Rogers et al., 1997, *Biochemistry* 36:288–300.
Rosseneu et al., In: *Structure and Function of the Lipoproteins*, Ch. 6, 159–183, CRC Press, Inc., 1992.
Rosseneu and Labeur, 1995, *FASEB J.* 9:768–776.
Rubin et al., 1991, *Nature* 353:265–267.
Schnölzer and Kent, 1992, *Science* 256:221–225.
Schultz et al., 1993, *Nature* 365:762–764.
Segrest, 1974, *FEBS Lett.* 38:247–253.
Segrest, 1976, *FEBS Lett.* 69(1):111–114.
Segrest et al., 1983, *J. Biol. Chem.* 258:2290–2295.
Segrest et al., 1990, *Proteins: Structure, Function and Genetics* 8:103–117.
Segrest et al., 1992, *J. Lipid Res.* 33:141–166.
Segrest et al., 1994, *Advances in Protein Chemistry* 45:303–369.
Sorci–Thomas et al., 1993, *J. Biol. Chem.* 268:21403–21409.
Sorci–Thomas et al., 1997, *J. Biol. Chem.* 272(11):7278–7284.
Sparks et al., 1995, *J. Biol. Chem.* 270(10):5151–5157.

Sparrow and Gotto, 1980, *Ann. N.Y. Acad. Sci. 348*:187–211.
Sparrow and Gotto, 1982, *CRC Crit. Rev. Biochem. 13*:87–107.
Sparrow and Gotto, Ch. 10: "Lipid–Protein Interactions: Structure–Functions Relationships", (not dated).
Sparrow et al., 1981, In: "Peptides: Synthesis–Structure–Function," Roch and Gross, Eds., Pierce Chem. Co., Rockford, IL, 253–256.
Spuhler et al., 1994, *J. Biol. Chem. 269*(39):23904–23910.
Subbarao et al., 1988, *PROTEINS: Structure, Function and Genetics 3*:187–198.
Tam, 1988, *Proc. Natl. Acad. Sci. U.S.A. 85*:5409–5413.
Tytler et al., 1993, *J. Biol. Chem. 268*(29):22112–22118.
Vanloo et al., 1992, *Biochim. Biophys. Acta 1128*:258–266.
Venkatachalapathi et al., 1991, *Mol. Conformation and Biol. Interactions, Indian Acad. Sci. B*:585–596.
Venkatachalapathi et al., 1993, *PROTEINS: Structure, Function and Genetics 15*:349–359.
Wang et al., 1996, *Biochim. Biophys. Acta 1301*:174–184.
Wilmot and Thornton, 1988, *J. Mol. Biol. 203*:221–232.
Yancey et al., 1995, *Biochemistry 34*:7955–7965.
Yokoyama et al., 1980, *J. Biol. Chem. 255*(15):7333–7339.

* cited by examiner

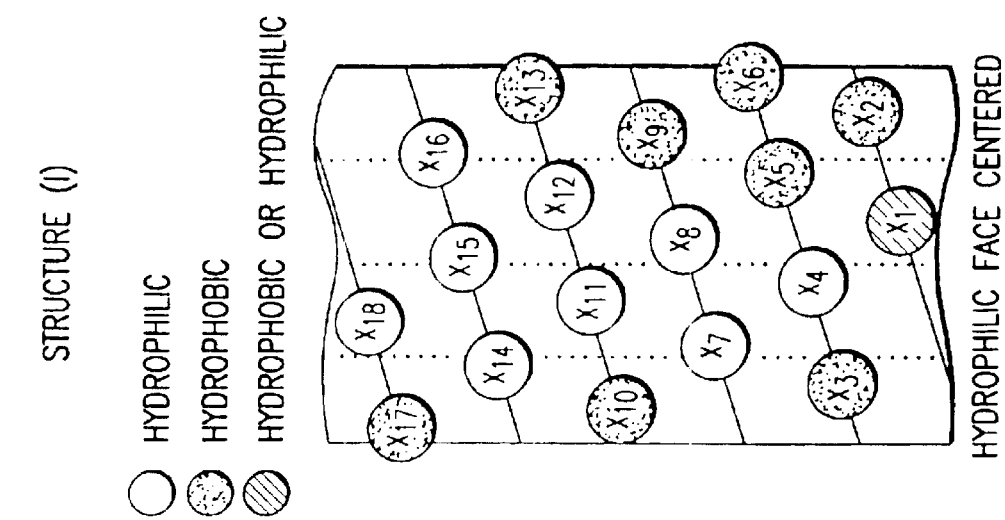
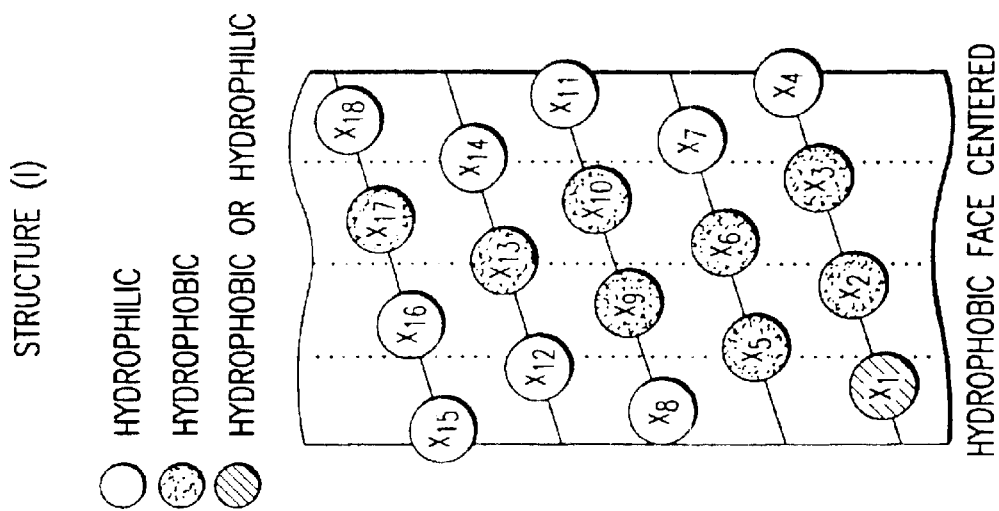
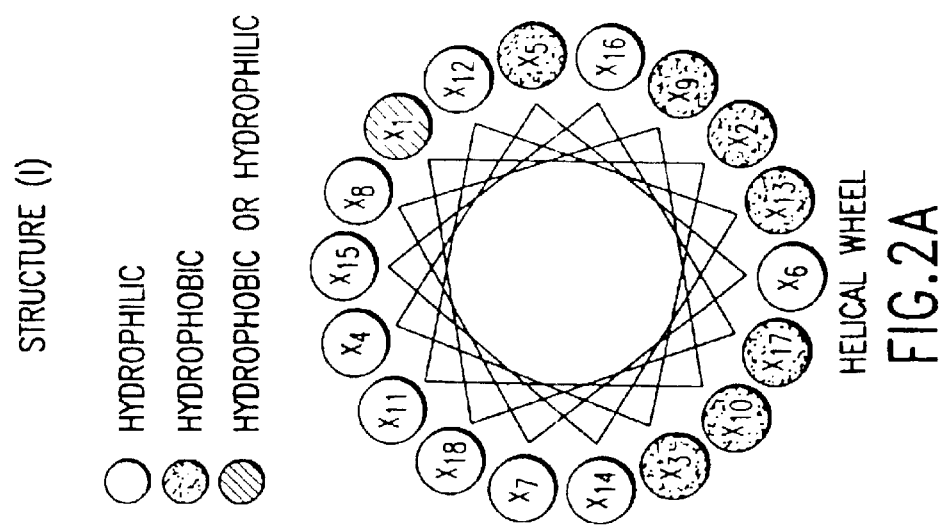

APOLIPOPROTEIN A-I AGONISTS AND THEIR USE TO TREAT DYSLIPIDEMIC DISORDERS

This is a continuation of application Ser. No. 09/465,719, filed Dec. 17, 1999, now U.S. Pat. No. 6,265,377, which is a continuation of application Ser. No. 08/940,093, filed Sep. 29, 1997, now U.S. Pat. No. 6,037,323.

1. INTRODUCTION

The invention relates to apolipoprotein A-I (ApoA-I) agonist compositions for treating disorders associated with dyslipoproteinemia, including hypercholesterolemia, cardiovascular disease, atherosclerosis, restenosis, and other disorders such as septic shock.

2. BACKGROUND OF THE INVENTION

Circulating cholesterol is carried by plasma lipoproteins—particles of complex lipid and protein composition that transport lipids in the blood. Low density lipoproteins (LDL), and high density lipoproteins (HDL) are the major cholesterol carriers. LDL are believed to be responsible for the delivery of cholesterol from the liver (where it is synthesized or obtained from dietary sources) to extrahepatic tissues in the body. The term "reverse cholesterol transport" describes the transport of cholesterol from extrahepatic tissues to the liver where it is catabolized and eliminated. It is believed that plasma HDL particles play a major role in the reverse transport process, acting as scavengers of tissue cholesterol.

The evidence linking elevated serum cholesterol to coronary heart disease is overwhelming. For example, atherosclerosis is a slowly progressive disease characterized by the accumulation of cholesterol within the arterial wall. Compelling evidence supports the concept that lipids deposited in atherosclerotic lesions are derived primarily from plasma LDL; thus, LDLs have popularly become known as the "bad" cholesterol. In contrast, HDL serum levels correlate inversely with coronary heart disease—indeed, high serum levels of HDL are regarded as a negative risk factor. It is hypothesized that high levels of plasma HDL are not only protective against coronary artery disease, but may actually induce regression of atherosclerotic plaques (e.g., see Badimon et al., 1992, Circulation 86 (Suppl. III):86–94). Thus, HDL have popularly become known as the "good" cholesterol.

2.1. CHOLESTEROL TRANSPORT

The fat-transport system can be divided into two pathways: an exogenous one for cholesterol and triglycerides absorbed from the intestine, and an endogenous one for cholesterol and triglycerides entering the bloodstream from the liver and other non-hepatic tissue.

In the exogenous pathway, dietary fats are packaged into lipoprotein particles called chylomicrons which enter the bloodstream and deliver their triglycerides to adipose tissue (for storage) and to muscle (for oxidation to supply energy). The remnant of the chylomicron, containing cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDLs consists mostly of triglycerides synthesized in the liver, with a smaller amount of cholesteryl esters (either synthesized in the liver or recycled from chylomicrons). Two predominant proteins are displayed on the surface of VLDLs, apoprotein B-100 and apoprotein E. When a VLDL reaches the capillaries of adipose tissue or of muscle, its triglycerides are extracted resulting in a new kind of particle, decreased in size and enriched in cholesteryl esters but retaining its two apoproteins, called intermediate-density lipoprotein (IDL).

In human beings, about half of the IDL particles are removed from the circulation quickly (within two to six hours of their formation), because they bind tightly to liver cells which extract their cholesterol to make new VLDL and bile acids. The IDL particles which are not taken up by the liver remain in the circulation longer. In time, the apoprotein E dissociates from the circulating particles, converting them to LDL having apoprotein B-100 as their sole protein.

Primarily, the liver takes up and degrades most of the cholesterol to bile acids, which are the end products of cholesterol metabolism. The uptake of cholesterol containing particles is mediated by LDL receptors, which are present in high concentrations on hepatocytes. The LDL receptor binds both apoprotein E and apoprotein B-100, and is responsible for binding and removing both IDLs and LDLs from the circulation. However, the affinity of apoprotein E for the LDL receptor is greater than that of apoprotein B-100. As a result, the LDL particles have a much longer circulating life span than IDL particles—LDLs circulate for an average of two and a half days before binding to the LDL receptors in the liver and other tissues. High serum levels of LDL (the "bad" cholesterol) are positively associated with coronary heart disease. For example, in atherosclerosis, cholesterol derived from circulating LDLs accumulates in the walls of arteries leading to the formation of bulky plaques that inhibit the flow of blood until a clot eventually forms, obstructing the artery causing a heart attack or stroke.

Ultimately, the amount of intracellular cholesterol liberated from the LDLs controls cellular cholesterol metabolism. The accumulation of cellular cholesterol derived from VLDLs and LDLs controls three processes: first, it reduces cellular cholesterol synthesis by turning off the synthesis of HMGCOA reductase—a key enzyme in the cholesterol biosynthetic pathway. Second, the incoming LDL-derived cholesterol promotes storage of cholesterol by activating ACAT—the cellular enzyme which converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading. (For a review, see Brown & Goldstein, In, The Pharmacological Basis Of Therapeutics, 8th Ed., Goodman & Gilman, Pergamon Press, NY, 1990, Ch. 36, pp. 874–896).

2.2. REVERSE CHOLESTEROL TRANSPORT

In sum, peripheral (non-hepatic) cells obtain their cholesterol from a combination of local synthesis and the uptake of preformed sterol from VLDLs and LDLs. In contrast, reverse cholesterol transport (RCT) is the pathway by which peripheral cell cholesterol can be returned to the liver for recycling to extrahepatic tissues, or excretion into the intestine in bile, either in modified or in oxidized form as bile acids. The RCT pathway represents the only means of eliminating cholesterol from most extrahepatic tissues, and is crucial to maintenance of the structure and function of most cells in the body.

The RCT consists mainly of three steps: (a) cholesterol efflux, the initial removal of cholesterol from various pools of peripheral cells; (b) cholesterol esterification by the action of lecithin:cholesterol acyltransferase (LCAT), preventing a re-entry of effluxed cholesterol into cells; and (c) uptake/delivery of HDL cholesteryl ester to liver cells. The RCT pathway is mediated by HDLs. HDL is a generic term for lipoprotein particles which are characterized by their high density. The main lipidic constituents of HDL complexes are various phospholipids, cholesterol (ester) and triglycerides. The most prominent apolipoprotein components are A-I and A-II which determine the functional characteristics of HDL; furthermore minor amounts of apolipoprotein C-I, C-II, C-III, D, E, J, etc. have been observed. HDL can exist in a wide variety of different sizes and different mixtures of the above-mentioned constituents depending on the status of remodeling during the metabolic RCT cascade.

The key enzyme involved in the RCT pathway is LCAT. LCAT is produced mainly in the liver and circulates in plasma associated with the HDL fraction. LCAT converts cell derived cholesterol to cholesteryl esters which are sequestered in HDL destined for removal. Cholesteryl ester transfer protein (CETP) and phospholipid transfer protein (PLTP) contribute to further remodeling the circulating HDL population. CETP can move cholesteryl esters made by LCAT to other lipoproteins, particularly ApoB-containing lipoproteins, such as VLDL and LDL. PLTP supplies lecithin to HDL. HDL triglycerides can be catabolized by the extracellular hepatic triglyceride lipase, and lipoprotein cholesterol is removed by the liver via several mechanisms.

Each HDL particle contains at least one copy (and usually two to four copies) of ApoA-I. ApoA-I is synthesized by the liver and small intestine as preproapolipoprotein which is secreted as a proprotein that is rapidly cleaved to generate a mature polypeptide having 243 amino acid residues. ApoA-I consists mainly of 6 to 8 different 22 amino acid repeats spaced by a linker moiety which is often proline, and in some cases consists of a stretch made up of several residues. ApoA-I forms three types of stable complexes with lipids: small, lipid-poor complexes referred to as pre-beta-1 HDL; flattened discoidal particles containing polar lipids (phospholipid and cholesterol) referred to as pre-beta-2 HDL; and spherical particles containing both polar and nonpolar lipids, referred to as spherical or mature HDL ($HDL_3$ and $HDL_2$). Most HDL in the circulating population contain both ApoA-I and ApoA-II (the second major HDL protein) and are referred to herein as the AI/AII-HDL fraction of HDL. However, the fraction of HDL containing only ApoA-I (referred to herein as the AI-HDL fraction) appear to be more effective in RCT. Certain epidemiologic studies support the hypothesis that the AI-HDL fraction is anti-atherogenic. (Parra et al., 1992, Arterioscler. Thromb. 12:701–707; Decossin et al., 1997, Eur. J. Clin. Invest. 27:299–307).

Although the mechanism for cholesterol transfer from the cell surface (i.e., cholesterol efflux) is unknown, it is believed that the lipid-poor complex, pre-beta-1 HDL is the preferred acceptor for cholesterol transferred from peripheral tissue involved in RCT. (See Davidson et al., 1994, J. Biol. Chem. 269:22975–22982; Bielicki et al., 1992, J. Lipid Res. 33:1699–1709; Rothblat et al., 1992, J. Lipid Res. 33:1091–1097; and Kawano et al., 1993, Biochemistry 32:5025–5028; Kawano et al., 1997, Biochemistry 36:9816–9825). During this process of cholesterol recruitment from the cell surface, pre-beta-1 HDL is rapidly converted to pre-beta-2 HDL. PLTP may increase the rate of pre-beta-2 disc formation, but data indicating a role for PLTP in RCT is lacking. LCAT reacts preferentially with discoidal and spherical HDL, transferring the 2-acyl group of lecithin or other phospholipids to the free hydroxyl residue of cholesterol to generate cholesteryl esters (retained in the HDL) and lysolecithin. The LCAT reaction requires ApoA-I as activator; i.e., ApoA-I is the natural cofactor for LCAT. The conversion of cholesterol to its ester sequestered in the HDL prevents re-entry of cholesterol into the cell, the result being that cholesteryl esters are destined for removal. Cholesteryl esters in the mature HDL particles in the AI-HDL fraction (i.e., containing ApoA-I and no ApoA-II) are removed by the liver and processed into bile more effectively than those derived from HDL containing both ApoA-I and ApoA-II (the AI/AII-HDL fraction). This may be due, in part, to the more effective binding of AI-HDL to the hepatocyte membrane. The existence of an HDL receptor has been hypothesized, and recently a scavenger receptor, SR-BI, was identified as an HDL receptor (Acton et al., 1996, Science 271:518–520; Xu et al., 1997, J. Lipid Res. 38:1289–1298). The SR-BI is expressed most abundantly in steroidogenic tissues (e.g., the adrenals), and in the liver (Landshulz et al., 1996, J. Clin. Invest. 98:984–995; Rigotti et al., 1996, J. Biol. Chem. 271:33545–33549).

CETP does not appear to play a major role in RCT, and instead is involved in the metabolism of VLDL- and LDL-derived lipids. However, changes in CETP activity or its acceptors, VLDL and LDL, play a role in "remodeling" the HDL population. For example, in the absence of CETP, the HDLs become enlarged particles which are not cleared. (For reviews on RCT and HDLs, see Fielding & Fielding, 1995, J. Lipid Res. 36:211–228; Barrans et al., 1996, Biochem. Biophys. Acta. 1300:73–85; Hirano et al., 1997, Arterioscler. Thromb. Vasc. Biol. 17(6):1053–1059).

2.3. CURRENT TREATMENTS FOR DYSLIPOPROTEINEMIAS

A number of treatments are currently available for lowering serum cholesterol and triglycerides (see, e.g., Brown & Goldstein, supra). However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), and colestipol hydrochloride (Colestid®, The Upjohn Company). When taken orally, these positively-charged resins bind to the negatively charged bile acids in the intestine. Because the resins cannot be absorbed from the intestine, they are excreted carrying the bile acids with them. The use of such resins, however, at best only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

The statins are cholesterol lowering agents that block cholesterol synthesis by inhibiting HMGCOA reductase—the key enzyme involved in the cholesterol biosynthetic pathway. The statins, e.g., lovastatin (Mevacor®, Merck & Co., Inc.), and pravastatin (Pravachol®, Bristol-Myers Squibb Co.) are sometimes used in combination with bile-acid-binding resins. The statins significantly reduce serum cholesterol and LDL-serum levels, and slow progression of coronary atherosclerosis. However, serum HDL cholesterol levels are only moderately increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (Physicians Desk Reference, Medical Economics Co., Inc., Montvale, N.J., 1997). Recently, the FDA has approved atorvastatin (an HMGCOA reductase inhibitor developed by Parke-Davis) (Warner Lambert) for the market to treat rare but urgent cases of familial hypercholesterolemia (1995, Scrip 20(19):10).

Niacin, or nicotinic acid, is a water soluble vitamin B-complex used as a dietary supplement and antihyperlipidemic agent. Niacin diminishes production of VLDL and is effective at lowering LDL. In some cases, it is used in combination with bile-acid binding resins. Niacin can increase HDL when used at adequate doses, however, its usefulness is limited by serious side effects when used at such high doses.

Fibrates are a class of lipid-lowering drugs used to treat various forms of hyperlipidemia (i.e., elevated serum triglycerides) which may also be associated with hypercholesterolemia. Fibrates appear to reduce the VLDL fraction and modestly increase HDL—however the effects of these drugs on serum cholesterol is variable. In the United States, fibrates have been approved for use as antilipidemic drugs, but have not received approval as hypercholesterolemia agents. For example, clofibrate (Atromid-S®, Wyeth-Ayerst Laboratories) is an antilipidemic agent which acts (via an unknown mechanism) to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®, Parke-Davis) is a lipid regulating agent which moderately decreases serum triglycerides and VLDL cholesterol, and moderately increases HDL cholesterol—the $HDL_2$ and $HDL_3$ subfractions as well as both ApoA-I and A-II (i.e., the AI/AII-HDL fraction). However, the lipid response is heterogeneous, especially among different patient populations. Moreover, while prevention of coronary heart disease was observed in male patients between 40–55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates including toxicity such as malignancy, (especially gastrointestinal cancer), gallbladder disease and an increased incidence in non-coronary mortality. These drugs are not indicated for the treatment of patients with high LDL or low HDL as their only lipid abnormality (Physician's Desk Reference, 1997, Medical Economics Co., Inc. Montvale, N.J.).

Oral estrogen replacement therapy may be considered for moderate hypercholesterolemia in post-menopausal women. However, increases in HDL may be accompanied with an increase in triglycerides. Estrogen treatment is, of course, limited to a specific patient population (postmenopausal women) and is associated with serious side effects including induction of malignant neoplasms, gall bladder disease, thromboembolic disease, hepatic adenoma, elevated blood pressure, glucose intolerance, and hypercalcemia.

Thus, there is a need to develop safer drugs that are efficacious in lowering serum cholesterol, increasing HDL serum levels, preventing coronary heart disease, and/or treating existing disease, especially atherosclerosis.

2.4. ApoA-I AS A TARGET

None of the currently available drugs for lowering cholesterol safely elevate HDL levels and stimulate RCT—most appear to operate on the cholesterol transport pathway, modulating dietary intake, recycling, synthesis of cholesterol, and the VLDL population.

While it is desirable to find drugs that stimulate cholesterol efflux and removal, several potential targets in the RCT exist—e.g., LCAT, HDL and its various components (ApoA-I, ApoA-II and phospholipids), PLTP, and CETP—and it is not known which target would be most effective at achieving desirable lipoprotein profiles and protective effects. Perturbation of any single component in the RCT pathway ultimately affects the composition of circulating lipoprotein populations, and the efficiency of RCT.

Several lines of evidence based on data obtained in vivo implicate the HDL and its major protein component, ApoA-I, in the prevention of atherosclerotic lesions, and potentially, the regression of plaques—making these attractive targets for therapeutic intervention. First, an inverse correlation exists between serum ApoA-I (HDL) concentration and atherogenesis in man (Gordon & Rifkind, 1989, N. Eng. J. Med. 321:1311–1316; Gordon et al., 1989, Circulation 79:8–15). Indeed, specific subpopulations of HDL have been associated with a reduced risk for atherosclerosis in humans (Miller, 1987, Amer. Heart 113:589–597; Cheung et al., 1991, Lipid Res. 32:383–394); Fruchart & Ailhaud, 1992, Clin. Chem. 38:79).

Second, animal studies support the protective role of ApoA-I (HDL). Treatment of cholesterol fed rabbits with ApoA-I or HDL reduced the development and progression of plaque (fatty streaks) in cholesterol-fed rabbits. (Koizumi et al., 1988, J. Lipid Res. 29:1405–1415; Badimon et al., 1989, Lab. Invest. 60:455–461; Badimon et al., 1990, J. Clin. Invest. 85:1234–1241). However, the efficacy varied depending upon the source of HDL (Beitz et al., 1992, Prostaglandins, Leukotrienes and Essential Fatty Acids 47:149–152; Mezdour et al., 1995, Atherosclerosis 113:237–246).

Third, direct evidence for the role of ApoA-I was obtained from experiments involving transgenic animals. The expression of the human gene for ApoA-I transferred to mice genetically predisposed to diet-induced atherosclerosis protected against the development of aortic lesions (Rubin et al., 1991, Nature 353:265–267). The ApoA-I transgene was also shown to suppress atherosclerosis in ApoE-deficient mice and in Apo(a) transgenic mice (Paszty et al., 1994, J. Clin. Invest. 94:899–903; Plump et al., 1994, Proc. Natl. Acad. Sci. USA 91:9607–9611; Liu et al., 1994, J. Lipid Res. 35:2263–2266). Similar results were observed in transgenic rabbits expressing human ApoA-I (Duverger, 1996, Circulation 94:713–717; Duverger et al., 1996, Arterioscler. Thromb. Vasc. Biol. 16:1424–1429), and in transgenic rats where elevated levels of human ApoA-I protected against atherosclerosis and inhibited restenosis following balloon angioplasty (Burkey et al., 1992, Circulation, Supplement I, 86:I-472, Abstract No. 1876; Burkey et al., 1995, J. Lipid Res. 36:1463–1473).

The AI-HDL appear to be more efficient at RCT than the AI/AII-HDL fraction. Studies with mice transgenic for human ApoA-I or Apo-I and ApoA-II (AI/AII) showed that the protein composition of HDL significantly affects its role—AI-HDL is more anti-atherogenic than AI/AII-HDL (Schultz et al., 1993, Nature 365:762–764). Parallel studies involving transgenic mice expressing the human LCAT gene demonstrate that moderate increases in LCAT activity significantly change lipoprotein cholesterol levels, and that LCAT has a significant preference for HDL containing ApoA-I (Francone et al., 1995, J. Clinic. Invest. 96:1440–1448; Berard et al., 1997, Nature Medicine 3(7): 744–749). While these data support a significant role for ApoA-I in activating LCAT and stimulating RCT, additional studies demonstrate a more complicated scenario: a major component of HDL that modulates efflux of cell cholesterol is the phospholipids (Fournier et al., 1996, J. Lipid Res. 37:1704–1711).

In view of the potential role of HDL, i.e., both ApoA-I and its associated phospholipid, in the protection against atherosclerotic disease, human clinical trials utilizing recombinantly produced ApoA-I were commenced, discontinued and apparently re-commenced by UCB Belgium (Pharmaprojects, Oct. 27, 1995; IMS R&D Focus, Jun. 30, 1997; Drug Status Update, 1997, Atherosclerosis 2(6) :261–265); see also M. Eriksson at Congress, "The Role of HDL in Disease Prevention," Nov. 7–9, 1996, Fort Worth; Lacko & Miller, 1997, J. Lip. Res. 38:1267–1273; and WO94/13819) and were commenced and discontinued by Bio-Tech (Pharmaprojects, Apr. 7, 1989). Trials were also attempted using ApoA-I to treat septic shock (Opal, "Reconstituted HDL as a Treatment Strategy for Sepsis," IBC's 7th International Conference on Sepsis, Apr. 28–30, 1997, Washington, D.C.; Gouni et al., 1993, J. Lipid Res. 94:139–146; Levine, WO96/04916). However, there are many pitfalls associated with the production and use of ApoA-I, making it less than ideal as a drug; e.c., ApoA-I is a large protein that is difficult and expensive to produce; significant manufacturing and reproducibility problems must be overcome with respect to stability during storage, delivery of an active product and half-life in vivo.

In view of these drawbacks, attempts have been made to prepare peptides that mimic ApoA-I. Since the key activities of ApoA-I have been attributed to the presence of multiple repeats of a unique secondary structural feature in the protein—a class A amphipathic α-helix (Segrest, 1974, FEBS Lett. 38:247–253), most efforts to design peptides which mimic the activity of ApoA-I have focused on designing peptides which form class A-type amphipathic α-helices.

Class A-type amphipathic α-helices are unique in that positively charged amino acid residues are clustered at the hydrophobic-hydrophilic interface and negatively charged amino acid residues are clustered at the center of the hydrophilic face. Furthermore, class A α-helical peptides have a hydrophobic angle of less than 180° (Segrest et al., 1990, PROTEINS: Structure, Function and Genetics 8:103–117). The initial de novo strategies to design ApoA-I mimics were not based upon the primary sequences of naturally occurring apolipoproteins, but rather upon incorporating these unique Class A helix features into the sequences of the peptide analogues, as well as some of the properties of the ApoA-I domains (see, e.g., Davidson et al., 1996, Proc. Natl. Acad. Sci. USA 93:13605–13610; Rogers et al., 1997, Biochemistry 36:288–300; Lins et al., 1993, Biochim. Biophys. Acta biomembranes 1151:137–142; Ji and Jonas, 1995, J. Biol. Chem. 270:11290–11297; Collet et al., 1997, Journal of Lipid Research, 38:634–644; Sparrow and Gotto, 1980, Ann. N.Y. Acad. Sci. 348:187–211; Sparrow and Gotto, 1982, CRC Crit. Rev. Biochem. 13:87–107; Sorci-Thomas et al., 1993, J. Biol. Chem. 268:21403–21409; Wang et al., 1996, Biochim. Biophys. Acta 174–184; Minnich et al., 1992, J. Biol. Chem. 267:16553–16560; Holvoet et al., 1995, Biochemistry 34:13334–13342; Sorci-Thomas et al., 1997, J. Biol. Chem. 272(11):7278–7284; and Frank et al., 1997, Biochemistry 36:1798–1806).

In one study, Fukushima et al. synthesized a 22-residue peptide composed entirely of Glu, Lys and Leu residues arranged periodically so as to form an amphipathic α-helix with equal hydrophilic and hydrophobic faces ("ELK peptide") (Fukushima et al., 1979, J. Amer. Chem. Soc. 101(13):3703–3704; Fukushima et al., 1980, J. Biol. Chem. 255:10651–10657). The ELK peptide shares 41% sequence homology with the 198–219 fragment of ApoA-I. As studied by quantitative ultrafiltration, gel permeation chromatography and circular dichroism, this ELK peptide was shown to effectively associate with phospholipids and mimic some of the physical and chemical properties of ApoA-I (Kaiser et al., 1983, Proc. Natl. Acad. Sci. USA 80:1137–1140; Kaiser et al., 1984, Science 223:249–255; Fukushima et al., 1980, supra; Nakagawa et al., 1985, J. Am. Chem. Soc. 107:7087–7092). Yokoyama et al. concluded from such studies that the crucial factor for LCAT activation is simply the presence of a large enough amphipathic structure (Yokoyama et al., 1980, J. Biol. Chem. 255(15):7333–7339). A dimer of this 22-residue peptide was later found to more closely mimic ApoA-I than the monomer; based on these results, it was suggested that the 44-mer, which is punctuated in the middle by a helix breaker (either Gly or Pro), represented the minimal functional domain in ApoA-I (Nakagawa et al., 1985, supra).

Another study involved model amphipathic peptides called "LAP peptides" (Pownall et al., 1980, Proc. Natl. Acad. Sci. USA 77(6):3154–3158; Sparrow et al., 1981, In: Peptides: Synthesis-Structure-Function, Roch and Gross, Eds., Pierce Chem. Co., Rockford, Ill., 253–256). Based on lipid binding studies with fragments of native apolipoproteins, several LAP peptides were designed, named LAP-16, LAP-20 and LAP-24 (containing 16, 20 and 24 amino acid residues, respectively). These model amphipathic peptides share no sequence homology with the apolipoproteins and were designed to have hydrophilic faces organized in a manner unlike the class A-type amphipathic helical domains associated with apolipoproteins (Segrest et al., 1992, J. Lipid Res. 33:141–166). From these studies, the authors concluded that a minimal length of 20 residues is necessary to confer lipid-binding properties to model amphipathic peptides.

Studies with mutants of LAP20 containing a proline residue at different positions in the sequence indicated that a direct relationship exists between lipid binding and LCAT activation, but that the helical potential of a peptide alone does not lead to LCAT activation (Ponsin et al., 1986 J. Biol. Chem. 261(20):9202–9205). Moreover, the presence of this helix breaker (Pro) close to the middle of the peptide reduced its affinity for phospholipid surfaces as well as its ability to activate LCAT. While certain of the LAP peptides were shown to bind phospholipids (Sparrow et al., supra), controversy exists as to the extent to which LAP peptides are helical in the presence of lipids (Buchko et al., 1996, J. Biol. Chem. 271(6):3039–3045; Zhong et al., 1994, Peptide Research 7(2):99–106).

Segrest et al. have synthesized peptides composed of 18 to 24 amino acid residues that share no sequence homology with the helices of ApoA-I (Kannelis et al., 1980, J. Biol. Chem. 255(3):11464–11472; Segrest et al., 1983, J. Biol. Chem. 258:2290–2295). The sequences were specifically designed to mimic the amphipathic helical domains of class A exchangeable apolipoproteins in terms of hydrophobic moment (Eisenberg et al., 1982, Nature 299:371–374) and charge distribution (Segrest et al., 1990, Proteins 8:103–117; U.S. Pat. No. 4,643,988). One 18-residue peptide, the "18A" peptide, was designed to be a model class-A α-helix (Segrest et al., 1990, supra). Studies with these peptides and other peptides having a reversed charged distribution, like the "18R" peptide, have consistently shown that charge distribution is critical for activity; peptides with a reversed charge distribution exhibit decreased lipid affinity relative to the 18A class-A mimics and a lower helical content in the presence of lipids (Kanellis et al., 1980, J. Biol. Chem. 255:11464–11472; Anantharamaiah et al., 1985, J. Biol. Chem. 260:10248–10255; Chung et al., 1985, J. Biol. Chem. 260:10256–10262; Epand et al., 1987, J. Biol. Chem. 262:9389–9396; Anantharamaiah et al., 1991, Adv. Exp. Med. Biol. 285:131–140).

Other synthetic peptides sharing no sequence homology with the apolipoproteins which have been proposed with limited success include dimers and trimers of the 18A peptide (Anantharamaiah et al., 1986, Proteins of Biological Fluids 34:63–66), GALA and EALA peptides (Subbarao et al., 1988, PROTEINS: Structure, Function and Genetics 3:187–198) and ID peptides (Labeur et al., 1997, Arteriosclerosis, Thrombosis and Vascular Biology 17:580–588) and the 18AM4 peptide (Brasseur et al., 1993, Biochim. Biophys. Acta 1170:1–7).

A "consensus" peptide containing 22-amino acid residues based on the sequences of the helices of human ApoA-I has also been designed (Anantharamaiah et al., 1990, Arteriosclerosis 10(1):95–105; Venkatachalapathi et al., 1991, Mol. Conformation and Biol. Interactions, Indian Acad. Sci. B:585–596). The sequence was constructed by identifying the most prevalent residue at each position of the hypothesized helices of human ApoA-I. Like the peptides described above, the helix formed by this peptide has positively charged amino acid residues clustered at the hydrophilic-hydrophobic interface, negatively charged amino acid residues clustered at the center of the hydrophilic face and a hydrophobic angle of less than 180°. While a dimer of this peptide is somewhat effective in activating LCAT, the monomer exhibited poor lipid binding properties (Venkatachalapathi et al., 1991, supra).

Based primarily on in vitro studies with the peptides described above, a set of "rules" has emerged for designing peptides which mimic the function of apoA-I. Significantly, it is thought that an amphipathic α-helix having positively charged residues clustered at the hydrophilic-hydrophobic interface and negatively charged amino acid residues clustered at the center of the hydrophilic face is required for lipid affinity and LCAT activation (Venkatachalapathi et al., 1991, supra). Anantharamaiah et al. have also indicated that the negatively charged Glu residue at position 13 of the consensus 22-mer peptide, which is positioned within the hydrophobic face of the α-helix, plays an important role in LCAT activation (Anantharamaiah et al., 1991, supra). Furthermore, Brasseur has indicated that a hydrophobic angle (pho angle) of less than 180° is required for optimal lipid-apolipoprotein complex stability, and also accounts for the formation of discoidal particles having the peptides around the edge of the lipid bilayer (Brasseur, 1991, J. Biol. Chem. 66(24):16120–16127). Rosseneu et al. have also insisted that a hydrophobic angle of less than 180° is required for LCAT activation (WO93/25581).

However, despite these "rules" to date, no one has designed or produced a peptide as active as ApoA-I—the best having less than 40% of the activity of ApoA-I as measured by the LCAT activation assay described herein. None of the peptide "mimetics" described in the literature have been demonstrated to be useful as a drug.

In view of the foregoing, there is a need for the development of a stable ApoA-I agonist that mimics the activity of ApoA-I and which is relatively simple and cost-effective to produce. However, the "rules" for designing efficacious ApoA-I mimetics have not been unraveled and the principles for designing organic molecules with the function of ApoA-I are unknown.

3. SUMMARY OF THE INVENTION

The invention relates to ApoA-I agonists capable of forming amphipathic α-helices that mimic the activity of ApoA-I, with specific activities, i.e., units of activity (activation of LCAT)/unit of mass), approaching or exceeding that of the native molecule. In particular, the ApoA-I agonists of the invention are peptides or peptide analogues that: form amphipathic helices (in the presence of lipids), bind lipids, form pre-β-like or HDL-like complexes, activate LCAT, increase serum levels of HDL fractions, and promote cholesterol efflux.

The invention is based, in part, on the applicants' design and discovery of peptides that mimic the function of ApoA-I. The peptides of the invention were designed based on the supposed helical structure and amphipathic properties of the 22 amino acid consensus sequence which was derived from the helical repeats of ApoA-I. Surprisingly, the peptides of the invention have a specific activity well above that reported for ApoA-I-derived peptides described in the literature. Indeed, some embodiments of the invention approach 100% of the activity of native ApoA-I, whereas superagonists described herein exceed the specific activity of ApoA-I.

One aspect of the invention is also based, in part, on the Applicants' discovery that amino acid residues 14–17 of Segrest's consensus 22-mers could be deleted without loss of LCAT activation. In some cases, the deletion of amino acid residues enhances LCAT activation. In another aspect of the invention, other residues of the consensus sequence can also be deleted with enhanced activity. In addition, in some embodiments, the deletion can be used in conjunction with alteration of amino acid residues. In some preferred embodiments, deletion of 4 residues from Segrest's consensus 22-mer peptide is used in conjunction with changes at residue 5, 9 and 13 to a hydrophobic leucine.

The invention is illustrated by way of working examples that describe the structure, preparation and use of particular amphipathic peptides that form helices (in the presence of lipids), bind lipids, form complexes and increase LCAT activity. Based upon the structure and activity of the exemplified embodiments, the applicants have devised a set of "rules" which can be used to design altered or mutated forms that are also within the scope of the invention.

The invention also relates to pharmaceutical formulations containing such ApoA-I agonists (either as peptides or peptide-lipid complexes) as the active ingredient, as well as methods for preparing such formulations and their use to treat diseases associated with dyslipoproteinemia (e.g., cardiovascular diseases, atherosclerosis, metabolic syndrome), restenosis, or endotoxemia (e.g., septic shock).

3.1. ABBREVIATIONS

As used herein, the abbreviations for the genetically encoded L-enantiomeric amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The abbreviations used for the D-enantiomers of the genetically encoded amino acids are lower-case equivalents of the one-letter symbols. For example, "R" designates L-arginine and "r" designates D-arginine.

3.2. DEFINITIONS

As used herein, the following terms shall have the following meanings:

"Alkyl:" refers to a saturated branched, straight chain or cyclic hydrocarbon radical. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are $(C_1-C_6)$ alkyl.

"Alkenyl:" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is $(C_1-C_6)$ alkenyl.

"Alkynyl:" refers to an unsaturated branched, straight chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is $(C_1-C_6)$ alkynyl.

"Aryl:" refers to an unsaturated cyclic hydrocarbon radical having a conjugated π electron system. Typical aryl groups include, but are not limited to, penta-2,4-diene, phenyl, naphthyl, anthracyl, azulenyl, chrysenyl, coronenyl, fluoranthenyl, indacenyl, idenyl, ovalenyl, perylenyl, phenalenyl, phenanthrenyl, picenyl, pleiadenyl, pyrenyl, pyranthrenyl, rubicenyl, and the like. In preferred embodiments, the aryl group is $(C_5-C_{20})$ aryl, with $(C_5-C_{10})$ being particularly preferred.

"Alkaryl:" refers to a straight-chain alkyl, alkenyl or alkynyl group wherein one of the hydrogen atoms bonded to a terminal carbon is replaced with an aryl moiety. Typical alkaryl groups include, but are not limited to, benzyl, benzylidene, benzylidyne, benzenobenzyl, naphthenobenzyl and the like. In preferred embodiments, the alkaryl group is $(C_6-C_{26})$ alkaryl, i.e., the alkyl, alkenyl or alkynyl moiety of the alkaryl group is $(C_1-C_6)$ and the aryl moiety is $(C_5-C_{20})$. In particularly preferred embodiments, the alkaryl group is $(C_6-C_{13})$ alkaryl, i.e., the alkyl, alkenyl or alkynyl moiety of the alkaryl group is $(C_1-C_3)$ and the aryl moiety is $(C_5-C_{10})$.

"Heteroaryl:" refers to an aryl moiety wherein one or more carbon atoms is replaced with another atom, such as N, P, O, S, As, Se, Si, Te, etc. Typical heteroaryl groups include, but are not limited to, acridarsine, acridine, arsanthridine, arsindole, arsindoline, carbazole, β-carboline, chromene, cinnoline, furan, imidazole, indazole, indole, indolizine, isoarsindole, isoarsinoline, isobenzofuran, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiophene and xanthene. In preferred embodiments, the heteroaryl group is a 5–20 membered heteroaryl, with 5–10 membered aryl being particularly preferred.

"Alkheteroaryl:" refers to a straight-chain alkyl, alkenyl or alkynyl group where one of the hydrogen atoms bonded to a terminal carbon atom is replaced with a heteroaryl moiety. In preferred embodiments, the alkheteroaryl group is 6–26 membered alkheteroaryl, i.e., the alkyl, alkenyl or alkynyl moiety of the alkheteroaryl is $(C_1-C_6)$ and the heteroaryl is a 5–20-membered heteroaryl. In particularly preferred embodiments the alkheteroaryl is 6–13 membered alkheteroaryl, i.e., the alkyl, alkenyl or alkynyl moiety is a 5–10 membered heteroaryl.

"Substituted Alkyl, Alkenyl, Alkynyl, Aryl, Alkaryl, Heteroaryl or Alkheteroaryl:" refers to an alkyl, alkenyl, alkynyl, aryl, alkaryl, heteroaryl or alkheteroaryl group in which one or more hydrogen atoms is replaced with another substituent. Preferred substituents include —OR, —SR, —NRR, —NO₂, —CN, halogen, —C(O)R, —C(O)OR and —C(O)NR, where each R is independently hydrogen, alkyl, alkenyl, alkynyl, aryl, alkaryl, heteroaryl or alkheteroaryl.

4. BRIEF DESCRIPTION OF THE FIGURES

FIG. 2A is a Schiffer-Edmundson helical wheel diagram of the core peptide of structure (I) illustrating the amphipathicity of the helix (open circles represent hydrophilic amino acid residues, shaded circles represent hydrophobic amino acid residues and partially shaded circles represent either hydrophilic or hydrophobic amino acid residues).

FIG. 2B is a helical net diagram of the core peptide of structure (I) illustrating the hydrophobic face of the helix.

FIG. 2C is a helical net diagram of the core peptide of structure (I) illustrating the hydrophilic face of the helix.

Figure 8A:
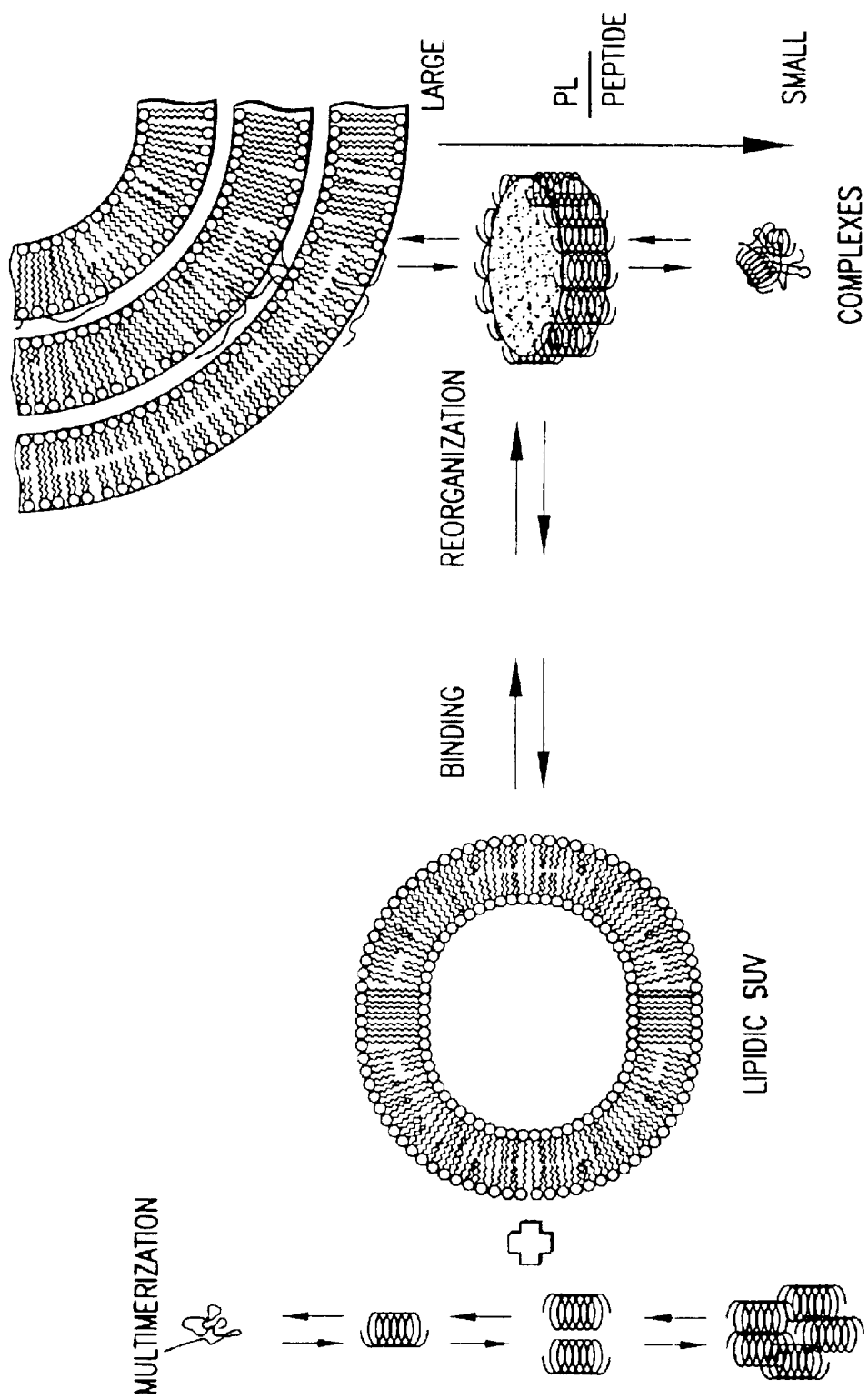

FIG. 8A is a cartoon depicting the various aggregation states and peptide-lipid complexes that can be obtained with the ApoA-I agonists of the invention. Left: Multimerization process of the peptides resulting from the interaction of several peptide helices and leading to the formation of oligomers in conditions of defined peptide concentration, pH and ionic strength. Center: The interaction of the peptides (in any of these states of aggregation) with lipidic entities (such as SUVs) leads to lipid reorganization. Right: By changing the lipid:peptide molar ratio, different types of peptide-lipid complexes can be obtained, from lipid-peptide comicelles at low lipid-peptide ratios, to discoidal particles and finally to large multilamellar complexes at increasingly higher lipid: peptide ratios.

Figure 8B:
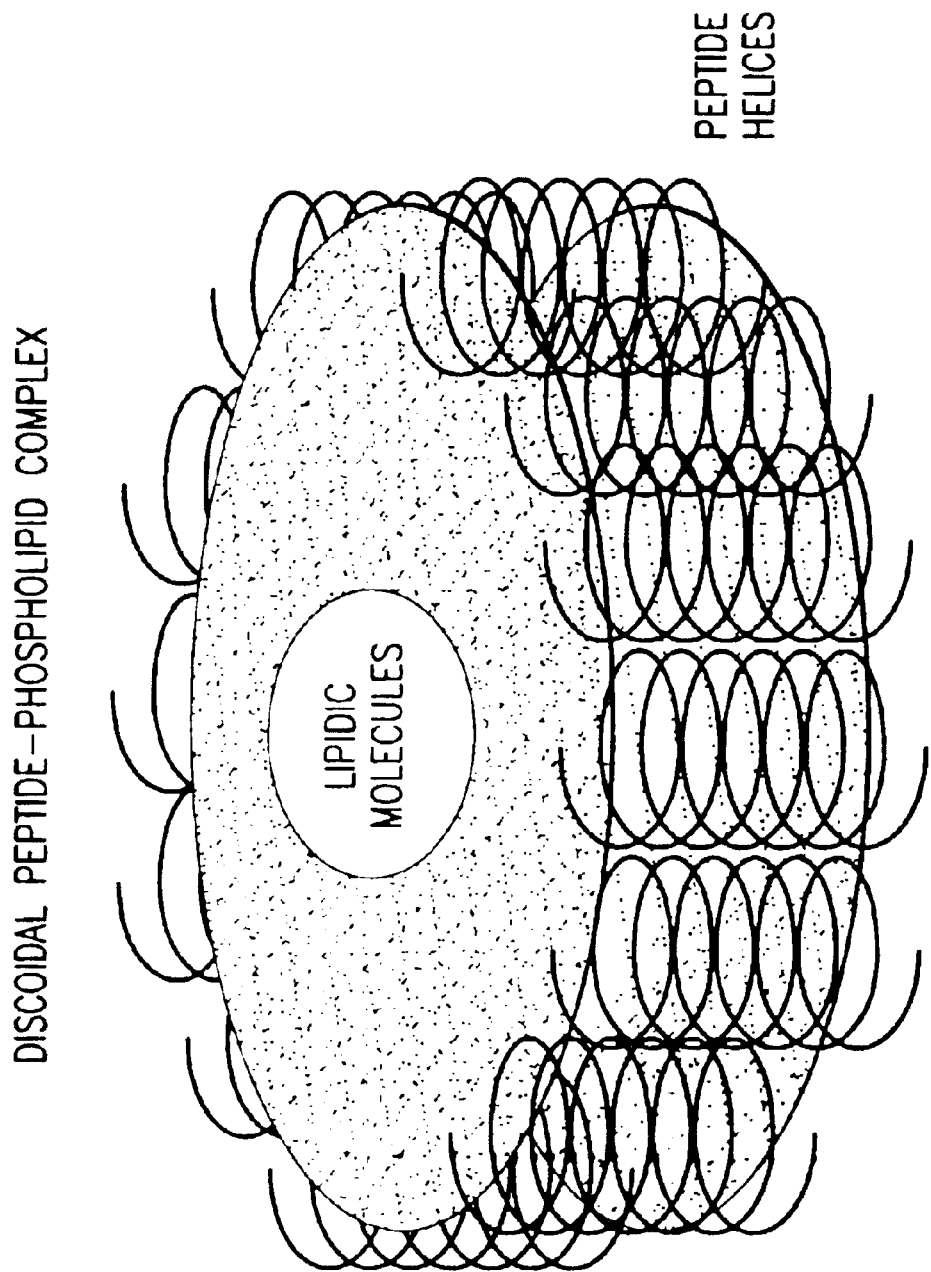

FIG. 8B illustrates the generally-accepted model for discoidal peptide-lipid complexes formed in a defined range of lipid:peptide ratios. Each peptide surrounding the disc edge is in close contact with its two nearest neighbors.

5. DETAILED DESCRIPTION OF THE INVENTION

The ApoA-I agonists of the invention mimic ApoA-I function and activity. They form amphipathic helices (in the presence of lipids), bind lipids, form pre-β-like or HDL-like complexes, activate LCAT, increase serum HDL concentration and promote cholesterol efflux. The biological function of the peptides correlates with their helical structure, or conversion to helical structures in the presence of lipids.

The ApoA-I agonists of the invention can be prepared in stable bulk or unit dosage forms, e.g., lyophilized products, that can be reconstituted before use in vivo or reformulated. The invention includes the pharmaceutical formulations and the use of such preparations in the treatment of hyperlipidemia, hypercholesterolemia, coronary heart disease, atherosclerosis, and other conditions such as endotoxemia causing septic shock.

The invention is illustrated by working examples which demonstrate that the ApoA-I agonists of the invention are extremely efficient at activating LCAT, and thus promote RCT. Use of the ApoA-I agonists of the invention in vivo in animal models results in an increase in serum HDL concentration.

The invention is set forth in more detail in the subsections below, which describe: the composition and structure of the ApoA-I peptide agonists; structural and functional characterization; methods of preparation of bulk and unit dosage formulations; and methods of use.

5.1. PEPTIDE STRUCTURE AND FUNCTION

The ApoA-I agonists of the invention are generally peptides, or analogues thereof, which are capable of forming amphipathic α-helices in the presence of lipids and which mimic the activity of ApoA-I. The agonists have as their main feature a "core" peptide composed of 15 to 22 amino acid residues, preferably 18 amino acid residues, or an analogue thereof wherein at least one amide linkage in the peptide is replaced with a substituted amide, an isostere of an amide or an amide mimetic.

The ApoA-I agonists of the invention are based, in part, on the applicants' surprising discovery that altering and/or deleting certain amino acid residues in the primary sequence of the 22-mer consensus sequence of Venkatachalapathi et al., 1991, Mol. Conformation and Biol. Interactions, Indian Acad. Sci. B:585–596 (PVLDEFREKLNEELEALKQKLK; SEQ ID NO:75; hereinafter "Segrest's consensus 22-mer" or "consensus 22-mer") that were thought to be critical for activity yields synthetic peptides which exhibit activities that approach, or in some embodiments even exceed, the activity of native ApoA-I. In one aspect of the invention, four amino acid residues of the consensus 22-mer, such as residues 14–17, are deleted to form 18-mers capable of LCAT activation. In other additional embodiments, four other residues are deleted. In some embodiments, three charged amino acid residues that were thought to be critical for activity (Glu-5, Lys-9 and Glu-13) are replaced with a hydrophobic residue such as Leu.

While not intending to be bound by any particular theory, it is believed that the helix formed by the ApoA-I agonists of the invention more closely mimics the structural and functional properties of the amphipathic helical regions of native ApoA-I that are important for effecting lipid-binding, cholesterol efflux and LCAT activation than does the α-helix formed by the ApoA-I mimetic peptides described in the literature, thereby resulting in peptides that exhibit significantly higher ApoA-I-like activity than these other peptides. Indeed, whereas many of the ApoA-I agonists of the invention approach, and in some embodiments even exceed, the activity of ApoA-I, to date, the best peptide ApoA-I mimics described in the literature—peptide 18AM4 (EWLEAFYKKVLEKLKELF; SEQ ID NO:246) (Corinjn et al., 1993, Biochim. Biophys. Acta 1170:8–16; Labeur et al., October 1994, Arteriosclerosis: Abstract Nos. 186 and 187) and N-acetylated, C-amidated peptide 18AM4 (SEQ ID NO: 239) (Brasseur, 1993, Biochim. Biophys. Acta 1170:1–7)—exhibit less than 4% and 11%, respectively, of the activity of ApoA-I as measured by the LCAT activation assay described herein.

In one illustrative embodiment of the invention, the core peptides (or analogues thereof) that compose the ApoA-I agonists of the invention have the following structural formula (I):

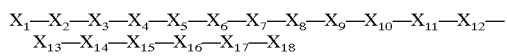

wherein:

X$_1$ is Pro (P), Ala (A), Gly (G), Asn (N), Gln (Q) or D-Pro (p);

X$_2$ is an aliphatic amino acid;

X$_3$ is Leu (L);

X$_4$ is an acidic amino acid;

X$_5$ is Leu (L) or Phe (F);

X$_6$ is Leu (L) or Phe (F);

X$_7$ is a basic amino acid;

X$_8$ is an acidic amino acid;

X$_9$ is Leu (L) or Trp (W);

X$_{10}$ is Leu (L) or Trp (W);

X$_{11}$ is an acidic amino acid or Asn (N);

X$_{12}$ is an acidic amino acid;

X$_{13}$ is Leu (L), Trp (W) or Phe (F);

X$_{14}$ is a basic amino acid or Leu (L);

X$_{15}$ is Gln (Q) or Asn (N);

X$_{16}$ is a basic amino acid;

X$_{17}$ is Leu (L); and

X$_{18}$ is a basic amino acid.

The core peptides of structure (I) are defined, in part, in terms of amino acids of designated classes. The definitions of the various designated classes are provided infra in connection with the description of mutated or altered embodiments of structure (I).

In the core peptides of structure (I), the symbol "—" between amino acid residues X$_n$ generally designates a backbone constitutive linking function. Thus, the symbol "—" usually represents a peptide bond or amide linkage (—C(O)NH—). It is to be understood, however, that the present invention contemplates peptide analogues wherein one or more amide linkages is optionally replaced with a linkage other than amide, preferably a substituted amide or an isostere of amide. Thus, while the various X$_n$ residues within structure (I) are generally described in terms of amino acids, and preferred embodiments of the invention are exemplified by way of peptides, one having skill in the art will recognize that in embodiments having non-amide linkages, the term "amino acid" or "residue" as used herein refers to other bifunctional moieties bearing groups similar in structure to the side chains of the amino acids.

Substituted amides generally include, but are not limited to, groups of the formula —C(O)NR—, where R is (C$_1$–C$_6$) alkyl, substituted (C$_1$–C$_6$) alkyl, (C$_1$–C$_6$) alkenyl, substituted (C$_1$–C$_6$) alkenyl, (C$_1$–C$_6$) alkynyl, substituted (C$_1$–C$_6$) alkynyl, (C$_5$–C$_{20}$) aryl, substituted (C$_5$–C$_{20}$) aryl, (C$_6$–C$_{26}$) alkaryl, substituted (C$_6$–C$_{26}$) alkaryl, 5–20 membered heteroaryl, substituted 5–20 membered heteroaryl or 6–26 membered alkheteroaryl and substituted 6–26 membered alkheteroaryl.

Isosteres of amide generally include, but are not limited to, —CH$_2$NH—, —CH$_2$S—, —CH$_2$CH$_2$—, —CH=CH— (cis and trans), —C(O)CH$_2$—, —CH(OH)CH$_2$— and —CH$_2$SO—. Compounds having such non-amide linkages and methods for preparing such compounds are well-known in the art (see, e.g., Spatola, March 1983, Vega Data Vol. 1, Issue 3; Spatola, 1983, "Peptide Backbone Modifications" In: Chemistry and Biochemistry of Amino Acids Peptides and Proteins, Weinstein, ed., Marcel Dekker, New York, p. 267 (general review); Morley, 1980, Trends Pharm. Sci. 1:463–468; Hudson et al., 1979, Int. J. Prot. Res. 14:177–185 (—CH$_2$NH—, —CH$_2$CH$_2$—); Spatola et al., 1986, Life Sci. 38:1243–1249 (—CH$_2$—S); Hann, 1982, J. Chem. Soc. Perkin Trans. I. 1:307–314 (—CH=CH—, cis and trans); Almquist et al., 1980, J. Med. Chem. 23:1392–1398 (—COCH$_2$—); Jennings-White et al., Tetrahedron. Lett. 23:2533 (—COCH$_2$—); European Patent Application EP 45665 (1982) CA 97:39405 (—CH(OH)CH$_2$—); Holladay et al., 1983, Tetrahedron Lett. 24:4401–4404 (—C(OH)CH$_2$—); and Hruby, 1982, Life Sci. 31:189–199 (—CH$_2$—S—).

Additionally, one or more amide linkages can be replaced with peptidomimetic or amide mimetic moieties which do not significantly interfere with the structure or activity of the peptides. Suitable amide mimetic moieties are described, for example, in Olson et al., 1993, J. Med. Chem. 36:3039–3049.

Figure 1C:
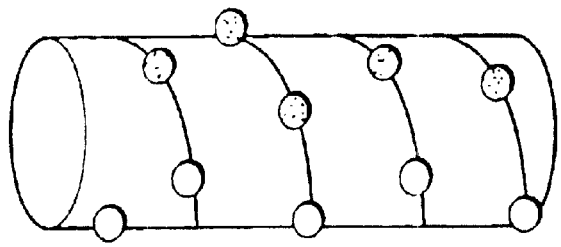
FIG. 1C is a helical cylinder diagram of the idealized amphipathic helix of FIG. 1A.
Figure 1B:
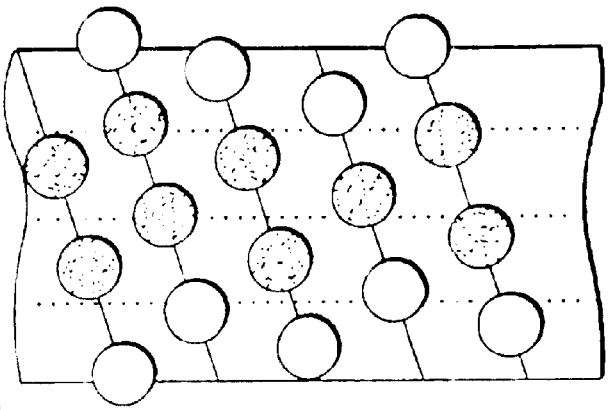
FIG. 1B is a helical net diagram of the idealized amphipathic helix of FIG. 1A.
Figure 1A:
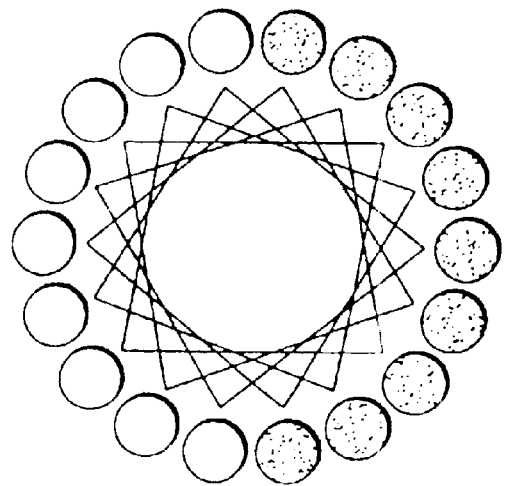
FIG. 1A is a Schiffer-Edmundson helical wheel diagram of an idealized amphipathic α-helix in which open circles represent hydrophilic amino acid residues and shaded circles represent hydrophobic amino acid residues.

A critical feature of the core peptides of structure (I), is their ability to form an amphipathic α-helix in the presence of lipids. By amphipathic is meant that the α-helix has opposing hydrophilic and hydrophobic faces oriented along its long axis, i.e., one face of the helix projects mainly hydrophilic side chains while the opposite face projects mainly hydrophobic side chains. FIGS. 1A and 1B present two illustrative views of the opposing hydrophilic and hydrophobic faces of an exemplary idealized amphipathic α-helix. FIG. 1A is a Schiffer-Edmundson helical wheel diagram (Schiffer and Edmundson, 1967, Biophys. J. 7:121–135). In the wheel, the long axis of the helix is perpendicular to the page. Starting with the N-terminus, successive amino acid residues (represented by circles) are radially distributed about the perimeter of a circle at 100° intervals. Thus, amino acid residue n+1 is positioned 100° from residue n, residue n+2 is positioned 100° from residue n+1, and so forth. The 100° placement accounts for the 3.6 amino acid residues per turn that are typically observed in an idealized α-helix. In FIG. 1A, the opposing hydrophilic and hydrophobic faces of the helix are clearly visible; hydrophilic amino acids are represented as open circles and hydrophobic amino acid residues are represented as shaded circles.

FIG. 1B presents a helical net diagram of the idealized amphipathic helix of FIG. 1A. (Lim, 1978, FEBS Lett. 89:10–14). In a typical helical net diagram, the α-helix is presented as a cylinder that has been cut along the center of its hydrophilic face and flattened. Thus, the center of the hydrophobic face, determined by the hydrophobic moment of the helix (Eisenberg et al., 1982, Nature 299:371–374), lies in the center of the figure and is oriented so as to rise out of the plane of the page. An illustration of the helical cylinder prior to being cut and flattened is depicted in FIG. 1C. By cutting the cylinder along different planes, different views of the same amphipathic helix can be observed, and different information about the properties of the helix obtained.

The amphipathic nature of the α-helix formed by the core peptides of structure (I) in the presence of lipids is illustrated in FIG. 2. FIG. 2A presents a Schiffer-Edmundson helical wheel diagram, FIG. 2B presents a helical net diagram illustrating the hydrophobic face and FIG. 2C presents a helical net diagram illustrating the hydrophilic face. In each of FIGS. 2A, 2B and 2C, hydrophilic residues are represented as open circles, hydrophobic residues as shaded circles, and residues which can be either hydrophilic or hydrophobic as partially shaded circles. As will be discussed more thoroughly below in conjunction with altered or mutated forms of the peptides of structure (I), certain amino acid residues can be replaced with other amino acid residues such that the hydrophilic and hydrophobic faces of the helix formed by the peptides may not be composed entirely of hydrophilic and hydrophobic amino acids, respectively. Thus, it is to be understood that when referring to the amphipathic α-helix formed by the core peptides of the invention, the phrase "hydrophilic face" refers to a face of the helix having overall net hydrophilic character. The phrase "hydrophobic face" refers to a face of the peptide having overall net hydrophobic character.

While not intending to be bound by any particular theory, it is believed that certain structural and/or physical properties of the amphipathic helix formed by the core peptides of structure (I), are important for activity. These properties include the degree of amphipathicity, overall hydrophobicity, mean hydrophobicity, hydrophobic and hydrophilic angles, hydrophobic moment, mean hydrophobic moment, and net charge of the α-helix.

While the helical wheel diagrams of FIG. 2A provide a convenient means of visualizing the amphipathic nature of the core peptides of structure (I), the degree of amphipathicity (degree of asymmetry of hydrophobicity) can be conveniently quantified by calculating the hydrophobic moment ($\mu_H$) of the helix. Methods for calculating $\mu_H$ for a particular peptide sequence are well-known in the art, and are described, for example in Eisenberg, 1984, Ann. Rev. Biochem. 53:595–623. The actual $\mu_H$ obtained for a particular peptide will depend on the total number of amino acid residues composing the peptide. Thus, it is generally not informative to directly compare $\mu_H$ for peptides of different lengths.

The amphipathicities of peptides of different lengths can be directly compared by way of the mean hydrophobic moment ($<\mu_H>$). The mean hydrophobic moment can be obtained by dividing $\mu_H$ by the number of residues in the helix (i.e., $<\mu_H>=\mu_H/N$). Generally, core peptides which exhibit a $<\mu_H>$ in the range of 0.55 to 0.65, as determined using the normalized consensus hydrophobicity scale of Eisenberg (Eisenberg, 1984, J. Mol. Biol. 179:125–142) are considered to be within the scope of the present invention, with a $<\mu_H>$ in the range of 0.58 to 0.62 being preferred.

The overall or total hydrophobicity ($H_o$) of a peptide can be conveniently calculated by taking the algebraic sum of the hydrophobicities of each amino acid residue in the peptide $$\left(\text{i.e., } H_o = \sum_{i=1}^{N} H_i\right),$$

where N is the number of amino acid residues in the peptide and $H_i$ is the hydrophobicity of the ith amino acid residue). The mean hydrophobicity ($<H_o>$) is the hydrophobicity divided by the number of amino acid residues (i.e., $<H_o>= H_o/N$). Generally, core peptides that exhibit a mean hydrophobicity in the range of –0.150 to –0.070, as determined using the normalized consensus hydrophobicity scale of Eisenberg (Eisenberg, 1984, J. Mol. Biol. 179:125–142) are considered to be within the scope of the present invention, with a mean hydrophobicity in the range of –0.130 to –0.050 being preferred.

The total hydrophobicity of the hydrophobic face ($H_o^{pho}$) of an amphipathic helix can be obtained by taking the sum of the hydrophobicities of the hydrophobic amino acid residues which fall into the hydrophobic angle as defined below $$(\text{i.e., } H_o^{pho} = \sum_{i=1}^{N} H_i,$$

where $H_i$ is as previously defined and $N_H$ is the total number of hydrophobic amino acids in the hydrophobic face). The mean hydrophobicity of the hydrophobic face ($<H_o^{pho}>$) is $H_o^{pho}/N_H$ where $N_H$ is as defined above. Generally, core peptides which exhibit a $<H_o^{pho}>$, in the range of 0.90 to 1.20, as determined using the consensus hydrophobicity scale of Eisenberg (Eisenberg, 1984, supra; Eisenberg et al., 1982, supra) are considered to be within the scope of the present invention, with a $<H_o^{pho}>$ in the range of 0.950 to 1.10 being preferred.

Figure 5B:
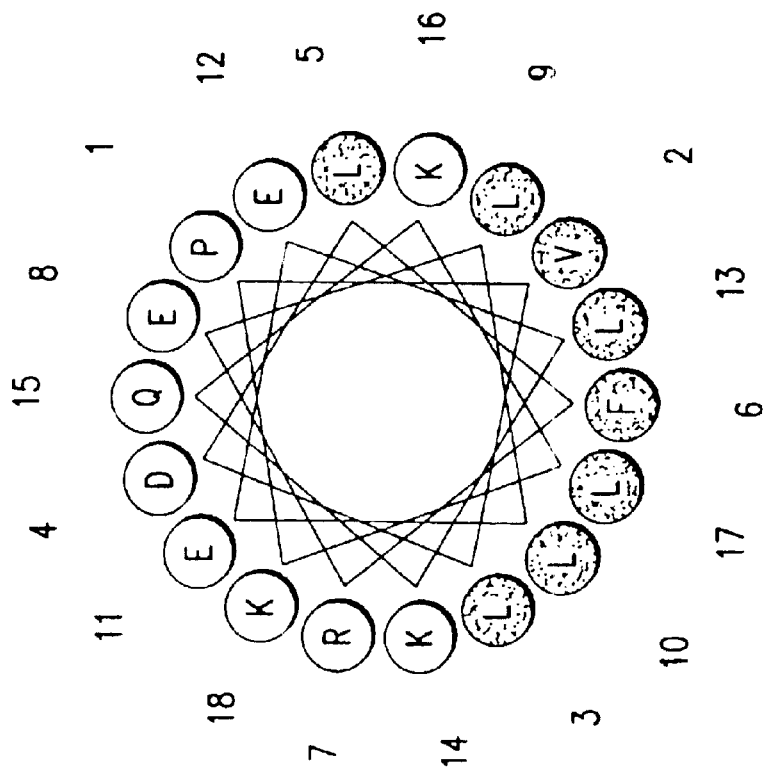
FIG. 5B is a Schiffer-Edmundson helical wheel diagram of exemplary core peptide 210 (SEQ ID NO:210).
Figure 5A:
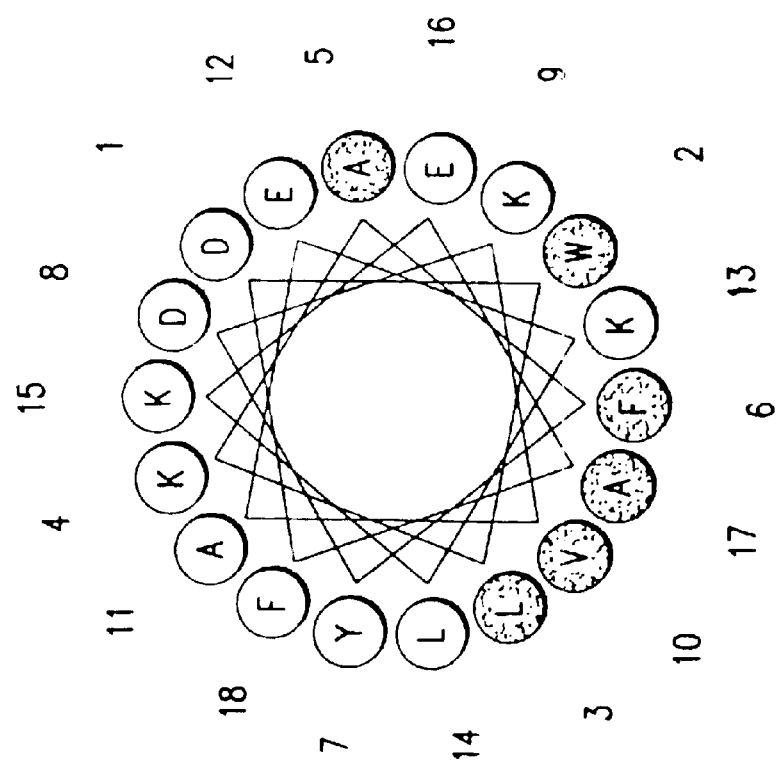
FIG. 5A is a Schiffer-Edmundson helical wheel diagram of Segrest's 18A peptide (SEQ ID NO:244).
Figure 6A:
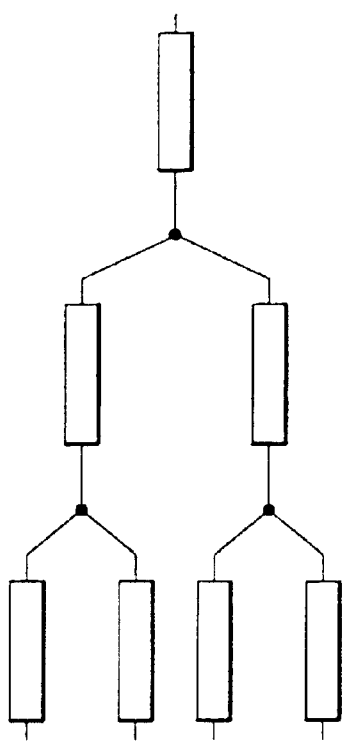
FIG. 6A illustrates a tertiary-order branched network of the invention.
Figure 6B:
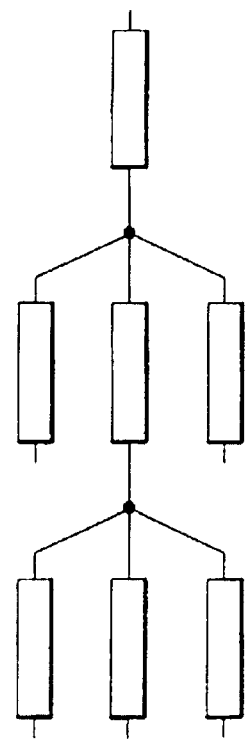
FIG. 6B illustrates a quaternary-order branched network of the invention.
Figure 6C:
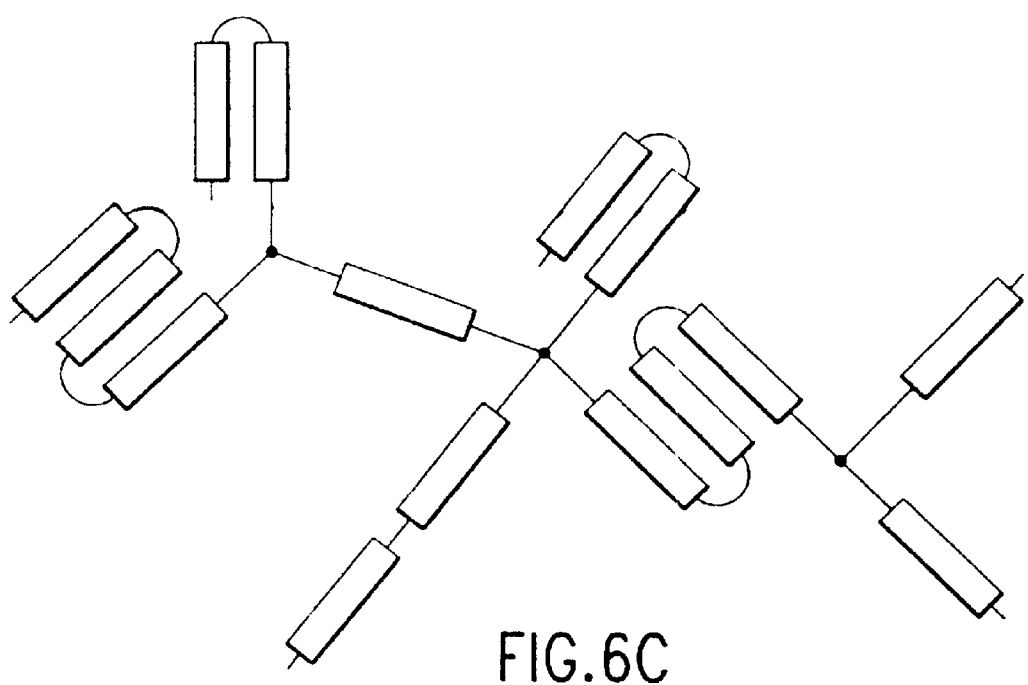
FIG. 6C illustrates a mixed-order branched network of the invention.
Figure 6D:
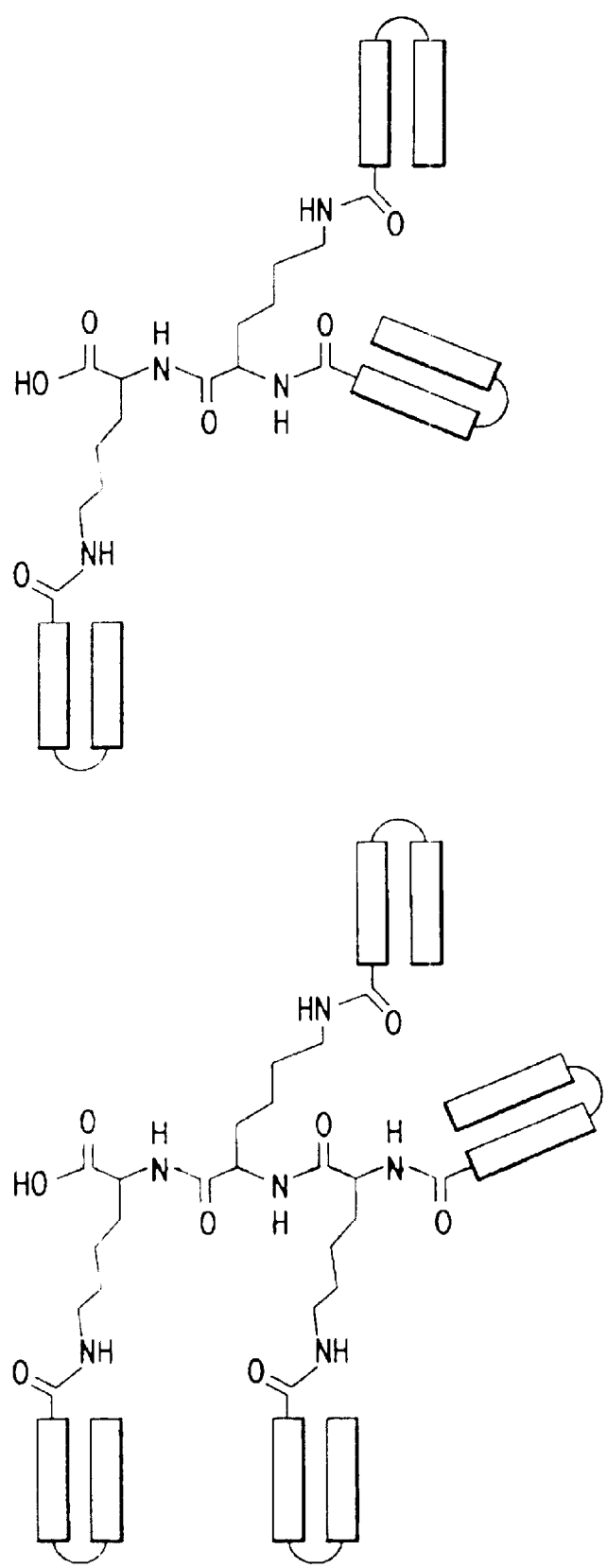
FIG. 6D illustrates exemplary "Lys-tree" branched networks of the invention.

The hydrophobic angle (pho angle) is generally defined as the angle or arc covered by the longest continuous stretch of hydrophobic amino acid residues when the peptide is arranged in the Schiffer-Edmundson helical wheel representation (i.e., the number of contiguous hydrophobic residues on the wheel multiplied by 20°). The hydrophilic angle (phi angle) is the difference between 360° and the pho angle (i.e., 360°-pho angle). Those of skill in the art will recognize that the pho and phi angles will depend, in part, on the number of amino acid residues in the peptide. For example, referring to FIGS. 5A and 5B, it can be seen that only 18 amino acids fit around one rotation of the Schiffer-Edmundson helical wheel. Fewer amino acids leave a gap in the wheel; more amino acids cause certain positions of the wheel to be occupied by more than one amino acid residue.

In the case of peptides containing more than 18 amino acid residues, by "continuous" stretch of hydrophobic amino acid residues is meant that at least one amino acid residue at positions along the wheel occupied by two or more amino acids is a hydrophobic amino acid.

Typically, core peptides composed of 18 or fewer amino acids having a pho angle in the range of 120° to 160° are considered to be within the scope of the invention, with a pho angle in the range of 130° to 150° being preferred. Embodiments containing more than 18 amino acids typically have a pho angle in the range of 160° to 220°, with 180° to 200° being preferred.

Figure 3C:
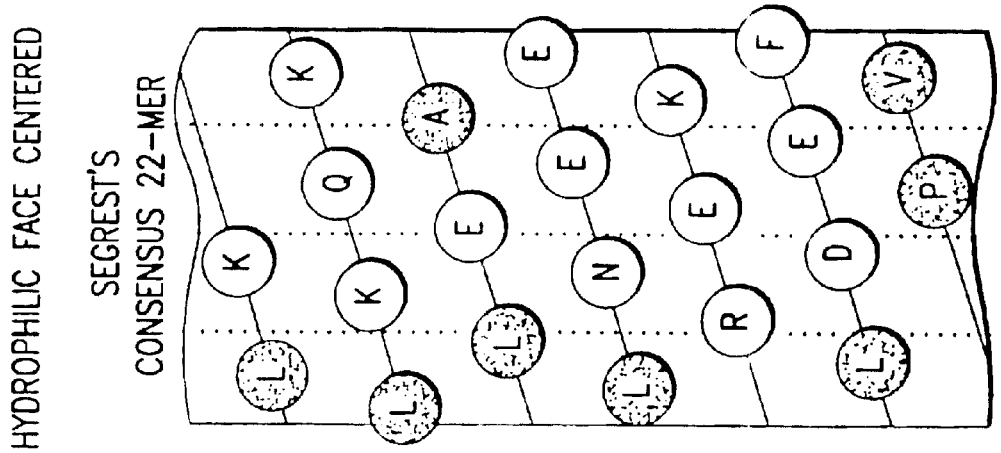
FIG. 3C is a helical net diagram illustrating the hydrophilic face of Segrest's consensus 22-mer peptide (PVLDEFREKLNEELEALKQKLK; SEQ ID NO:75).
Figure 3B:
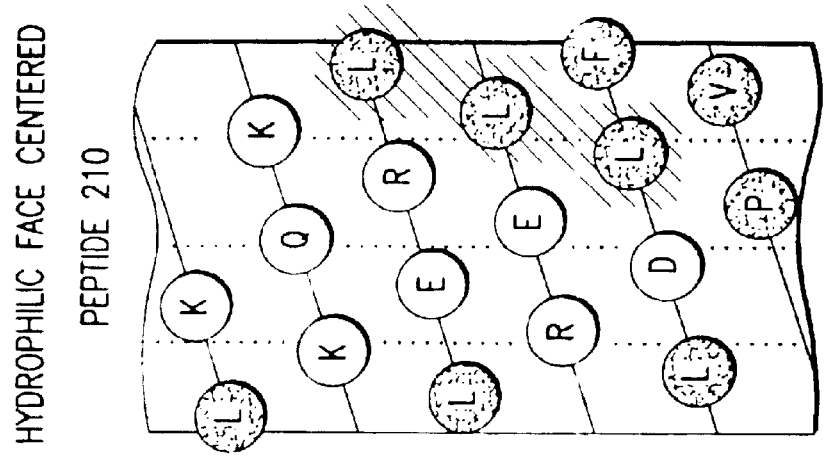
FIG. 3B is a helical net diagram illustrating the hydrophilic face of exemplary core peptide 210 (PVLDLFRELLEELKQKLK; SEQ ID NO:210).
Figure 3A:
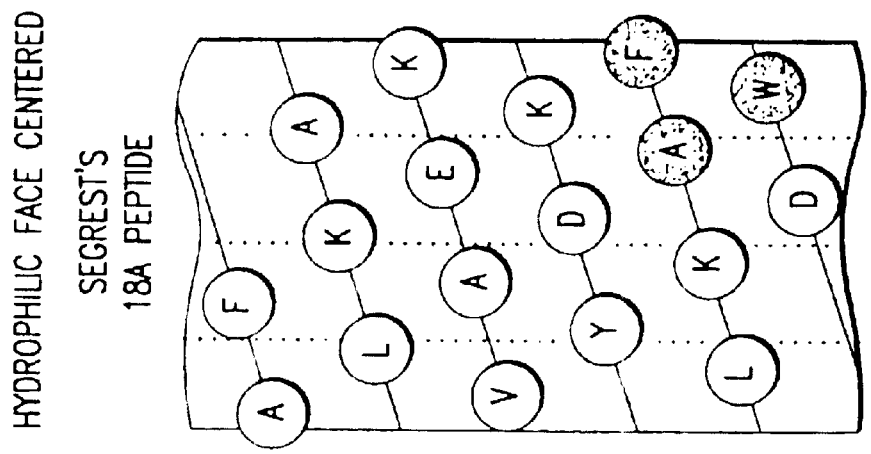
FIG. 3A is a helical net diagram illustrating the hydrophilic face of Segrest's 18A peptide (DWLKAFYDKVAEKLKEAF; SEQ ID NO:244).

Certain structural and/or physical characteristics of the core peptides of structure (I) are illustrated in FIGS. 3 and 4. FIG. 3B presents a helical net diagram of an exemplary core peptide of the invention, peptide 210 (PVLDLFRELLEELKQKLK; SEQ ID NO:210), illustrating the charge distribution along the hydrophilic face of the helix. In FIG. 3B, the helical cylinder has been cut along the center of the hydrophobic face and flattened. The three hydrophobic Leu (L) residues that replace hydrophilic residues in Segrest's consensus 22-mer (residues 5, 9 and 13) (FIG. 3C) are shaded. As can be seen in FIG. 3B, positively-charged amino acid residues are clustered at the last C-terminal turn of the helix (the C-terminus is at the top of the page). While not intending to be bound by any particular theory, it is believed that this cluster of basic residues at the C-terminus (residues 14, 16 and 18) stabilizes the helix through charge ($NH_3^+$)-helix dipole electrostatic interactions. It is also thought that stabilization occurs through hydrophobic interactions between lysine side chains and the helix core (see, Groebke et al., 1996, Proc. Natl. Acad. Sci. U.S.A. 93:4025–4029; Esposito et al., 1997, Biopolymers 41:27–35).

With the exception of the positively-charged C-terminal cluster (residues 14, 16 and 18), negative charges are distributed on the rest of the hydrophilic face, with at least one negatively charged (acidic) amino acid residue per turn, resulting in a continuous stretch of negative charges along the hydrophilic face of the helix.

Figure 4C:
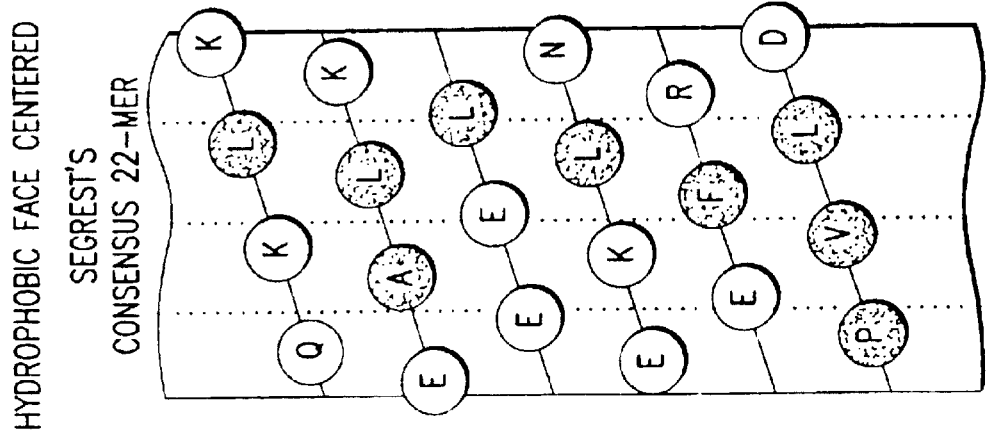
FIG. 4C is a helical net diagram illustrating the hydrophobic face of Segrest's consensus 22-mer peptide (SEQ ID NO:75).
Figure 4B:
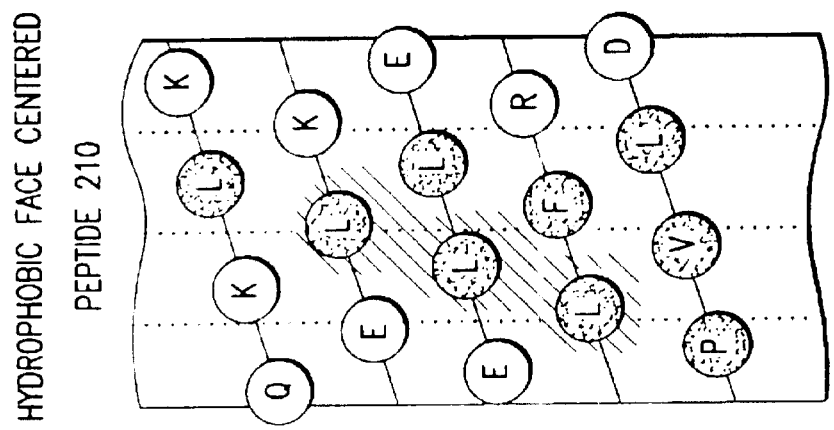
FIG. 4B is a helical net diagram illustrating the hydrophobic face of exemplary core peptide 210 (SEQ ID NO:210).

FIG. 4B presents a helical net diagram illustrating the hydrophobic face of the amphipathic helix formed by exemplary core peptide 210 (SEQ ID NO:210). In FIG. 4B, the helical cylinder is cut along the center of the hydrophilic face and flattened. The hydrophobic face of the core peptide consists of two hydrophobic residues per turn, except for the last C-terminal turn, where basic residues dominate. NMR studies indicate that amino acid residues 3, 6, 9 and 10 of an analogue 22-mer peptide (PVLDLFRELLNE-LLEALKQKLK; SEQ ID NO:4) form a hydrophobic cluster near the N-terminus of the helix. Phe-6 is centered in this cluster and is believed to play an important role in stabilizing the hydrophobic cluster.

While not intending to be bound by any particular theory, it is believed that the hydrophobic cluster formed by residues 3, 6, 9 and 10 is significant in effecting lipid binding and LCAT activation. Amphipathic peptides are expected to bind phospholipids by pointing their hydrophobic faces towards the alkyl chains of the lipid moieties. Thus, it is believed that this highly hydrophobic cluster contributes to the strong lipid affinities observed for the core peptides of the invention. Since lipid binding is a prerequisite for LCAT activation, it is believed that this hydrophobic cluster is also essential for LCAT activation.

Aromatic residues are often found to be important in anchoring peptides and proteins to lipids (De Kruijff, 1990, Biosci. Rep. 10:127–130; O'Neil and De Grado, 1990, Science 250:645–651; Blondelle et al., 1993, Biochim. Biophys. Acta 1202:331–336). Thus, it is further believed that Phe-6, which is positioned at the center of the hydrophobic cluster, may also play a key role in anchoring the core peptides of structure (I) to lipids.

Interactions between the core peptides of the invention and lipids lead to the formation of peptide-lipid complexes. As illustrated in FIG. 8A, the type of complex obtained (comicelles, discs, vesicles or multilayers) depends on the lipid:peptide molar ratio, with comicelles generally being formed at low lipid:peptide molar ratios and discoidal and vesicular or multilayer complexes being formed with increasing lipid:peptide molar ratios. This characteristic has been described for amphipathic peptides (Epand, The Amphipathic Helix, 1993) and for ApoA-I (Jones, 1992, Structure and Function of Apolipoproteins, Chapter 8, pp. 217–250). The lipid:peptide molar ratio also determines the size and composition of the complexes (see, Section 5.3.1, infra).

The long axis of the α-helix formed by the core peptides of structure (I) has an overall curved shape. In typical amphipathic helices, it has been found that the lengths of the hydrogen bonds of the hydrophilic and hydrophobic faces vary such that the hydrophobic side of the helix is concave (Barlow and Thornton, 1988, J. Mol. Biol. 201:601–619; Zhou et al., 1992, J. Am. Chem. Soc. 33:11174–11183; Gesell et al., 1997, J. Biomol. NMR 9:127–135). While not intending to be bound by theory, it is believed that the overall curvature of the hydrophobic face of the helix may be important in binding discoidal complexes—a curved helix permits the peptide to "fit" better around the edges of discoidal particles, thereby increasing the stability of the peptide-disc complex.

In the generally accepted structural model of ApoA-I, the amphipathic α-helices are packed around the edge of the discoidal HDL (see, FIG. 8B). In this model, the helices are assumed to be aligned with their hydrophobic faces pointing towards the lipid acyl chains (Brasseur et al., 1990, Biochim. Biophys. Acta 1043:245–252). The helices are arranged in an antiparallel fashion, and a cooperative effect between the helices is thought to contribute to the stability of the discoidal HDL complex (Brasseur et al., supra). It has been proposed that one factor that contributes to the stability of the HDL discoidal complex is the existence of ionic interactions between acidic and basic residues resulting in the formation of intermolecular salt bridges or hydrogen bonds between residues on adjacent anti-parallel helices. In this model, the peptides are considered not as a single entity, but as in interaction with at least two other neighboring peptide molecules (FIG. 8B).

It is also generally accepted that intramolecular hydrogen bond or salt bridge formation between acidic and basic residues, respectively, at positions i and i+3 of the helix stabilize the helical structure (Marqusee et al., 1985, Proc. Natl. Acad. Sci. USA 84(24):8898–8902). One positive charge is located at residue 7 potentially contributing to helix stability by forming a salt bridge with an acidic residue one turn away.

Thus, additional key features of the core peptides of structure (I) are their ability to form intermolecular hydrogen-bonds with one another when aligned in an antiparallel fashion with their hydrophobic faces pointing in the same direction, such as would be the case when the peptides are bound to lipids and also their ability to form intermolecular hydrogen bonds or salt bridges near the N- and C-termini of the helix. It is believed that the ability of the core peptides of structure (I) to closely pack and ionically interact to form intra- and/or inter-molecular salt bridges and/or hydrogen bonds when bound to lipids in an antiparallel fashion is an important feature of the core peptides of the invention.

The ability of the core peptides to form favorable intermolecular peptide-peptide interactions is also thought to be of relevance in the absence of lipids. The core peptides of the invention self-associate, due in part to their high $<\mu_H>$, $<H_o>$ and hydrophobic angle (see, TABLE I, infra). The self-association phenomenon depends on the conditions of pH, peptide concentration and ionic strength, and can result in several states of association, from monomeric to several multimeric forms (FIG. 10A). The hydrophobic core of peptide aggregates favors hydrophobic interactions with lipids. The ability of the peptides to aggregate even at very low concentrations may favor their binding to lipids. It is thought that in the core of the peptide aggregates peptide-peptide interactions also occur and may compete with lipid-peptide interactions.

In addition to the above-described properties, other parameters are thought to be important for activity as well, including the total number of hydrophobic residues, the total number of charged residues, and the net charge of the peptides.

A summary of the preferred physical and structural properties of the core peptides of structure (I) is provided in TABLE I, below:

TABLE I

PHYSICAL PROPERTIES OF PREFERRED ApoA-I AGONISTS OF STRUCTURE (I)

| PROPERTY | RANGE | PREFERRED RANGE |
|---|---|---|
| % hydrophobic amino acids | 40–70 | 50–60 |
| $<H_o>$ | −0.150 to −0.070 | −0.130 to −0.050 |
| $<H_o^{pho}>$ | 0.90–1.2 | 0.95–1.10 |
| $<\mu_H>$ | 0.55–0.65 | 0.58–0.62 |
| pho angle | 120°–160° | 130°–150° |
| # positively charged amino acids | 3–5 | 4 |
| # negatively charged amino acids | 3–5 | 4 |
| net charge | −1 to +1 | 0 |
| hydrophobic cluster | positions 3, 6, 9, 10 are hydrophobic amino acids | |
| acidic cluster | at least 1 acidic amino acid per turn except for last 5 C-terminal amino acids | |
| basic cluster | at least 2 basic amino acids in last 5 C-terminal amino acids | |

The properties of the amphipathic α-helices formed by the core peptides of the invention differ significantly from the properties of class A amphipathic α-helices, particularly the class A α-helix of Segrest's 18A and consensus 22-mer peptides. These differences are illustrated with exemplary core peptide 210 (SEQ ID NO:210) in FIGS. 3–5.

Figure 4A:
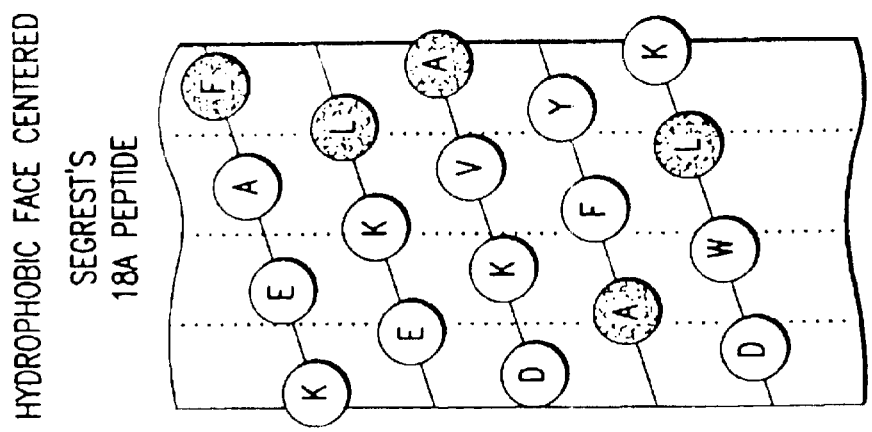
FIG. 4A is a helical net diagram illustrating the hydrophobic face of Segrest's 18A peptide (SEQ ID NO:244).

Referring to FIGS. 4A–4C, it can be seen that the hydrophobic face of peptide 210 has much greater hydrophobic character than the hydrophobic face of Segrest's 18A peptide or consensus 22-mer. In particular, residues 9 and 13 (shaded region of FIG. 4B) are hydrophobic Leu (L) residues in peptide 210 (SEQ ID NO:210) as compared to charged residues in the 18A peptide (SEQ ID NO:244) and the consensus 22-mer (SEQ ID NO:75). The replacement of these two charged residues in Segrest's 18A and consensus 22-mer peptides with hydrophobic Leu (L) residues leads to significant differences in the amphipathicity, hydrophobicity, pho angle and other properties of the helix.

A comparison of the physical and structural properties of peptide 210 (SEQ ID NO:210) and Segrest's 18A peptide (SEQ ID NO:244) and consensus 22-mer peptide (SEQ ID NO:75) is provided in TABLE II, below:

TABLE II

COMPARISON OF PROPERTIES OF EXEMPLARY CORE PEPTIDE 210 (SEQ ID NO:210) WITH SEGREST'S CONSENSUS 22-MER (SEQ ID NO:75) AND 18A PEPTIDE (SEQ ID NO:244)

| PROPERTY | 18A | CONSENSUS 22-MER | PEPTIDE 210 |
|---|---|---|---|
| # amino acids | 18 | 22 | 18 |
| # hydrophilic amino acids | 9 | 13 | 9 |
| # hydrophobic amino acids | 9 | 9 | 9 |
| % hydrophobic amino acids | 50 | 41 | 50 |
| $<H_o>$ | −0.43 | −0.293 | −0.125 |
| $<H_o^{pho}>$ | 0.778 | 0.960 | 1.081 |
| $<\mu_H>$ | 0.485 | 0.425 | 0.597 |
| pho angle | 100° | 100° | 140° |
| # positively charged amino acids | 4 | 5 | 4 |
| # negatively charged amino acids | 4 | 6 | 4 |
| net charge | 0 | −1 | 0 |

These differences in properties lead to significant differences in activity. Whereas Segrest's 18A peptide (SEQ ID NO:244) and consensus 22-mer peptide (SEQ ID NO:75) exhibit only 5% and 10% LCAT activation, respectively, as compared with native ApoA-I in the assays described herein, peptide 210 (SEQ ID NO:210) exhibits 46% activation as compared with native ApoA-I in the same assays. Peptide 193 (SEQ ID NO:193), which is the N-terminal acetylated and C-terminal amidated form of peptide 210, exhibits 96% LCAT activation in the same assay.

Certain amino acid residues in the core peptides of structure (I) can be replaced with other amino acid residues without significantly deleteriously affecting, and in many cases even enhancing, the activity of the peptides. Thus, also contemplated by the present invention are altered or mutated forms of the core peptides of structure (I) wherein at least one defined amino acid residue in the structure is substituted with another amino acid residue. As one of the critical features affecting the activity of the core peptides of the invention is believed to be their ability to form α-helices in the presence of lipids that exhibit the amphipathic and other properties described above, it will be recognized that in preferred embodiments of the invention, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into apolar and aromatic amino acids. The definitions of the various categories of amino acids that define structure (I) are as follows:

"Hydrophilic Amino Acid" refers to an amino acid exhibiting a hydrophobicity of less than zero according to the normalized consensus hydrophobicity scale of Eisenberg et al., 1984, J. Mol. Biol. 179:125–142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125–142. Genetically encoded hydrophobic amino acids include Pro (P), Ile (I), Phe (F), Val (V), Leu (L), Trp (W), Met (M), Ala (A), Gly (G) and Tyr (Y).

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —$NO_2$, —NO, —$NH_2$, —NHR, —NRR, —C(O)R, —C(O)OH, —C(O)OR, —C(O)$NH_2$, —C(O)NHR, —C(O)NRR and the like where each R is independently ($C_1$–$C_6$) alkyl, substituted ($C_1$–$C_6$) alkyl, ($C_1$–$C_6$) alkenyl, substituted ($C_1$–$C_6$) alkenyl, ($C_1$–$C_6$) alkynyl, substituted ($C_1$–$C_6$) alkynyl, ($C_5$–$C_{20}$) aryl, substituted ($C_5$–$C_{20}$) aryl, ($C_6$–$C_{26}$) alkaryl, substituted ($C_6$–$C_{26}$) alkaryl, 5–20 membered heteroaryl, substituted 5–20 membered heteroaryl, 6–26 membered alkheteroaryl or substituted 6–26 membered alkheteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the present invention Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

Certain amino acid residues, called "helix breaking" amino acids, have a propensity to disrupt the structure of α-helices when contained at internal positions within the helix. Amino acid residues exhibiting such helix-breaking properties are well-known in the art (see, e.g., Chou and Fasman, Ann. Rev. Biochem. 47:251–276) and include Pro (P), Gly (G) and potentially all D-amino acids (when contained in an L-peptide; conversely, L-amino acids disrupt helical structure when contained in a D-peptide). While these helix-breaking amino acid residues fall into the categories defined above, these residues should not be used to substitute amino acid residues at internal positions within the helix—they should only be used to substitute 1–3 amino acid residues at the N-terminus and/or C-terminus of the peptide.

While the above-defined categories have been exemplified in terms of the genetically encoded amino acids, the amino acid substitutions need not be, and in certain embodiments preferably are not, restricted to the genetically encoded amino acids. Indeed, many of the preferred peptides of structure (I) contain genetically non-encoded amino acids. Thus, in addition to the naturally occurring genetically encoded amino acids, amino acid residues in the core peptides of structure (I) may be substituted with naturally occurring non-encoded amino acids and synthetic amino acids.

Certain commonly encountered amino acids which provide useful substitutions for the core peptides of structure (I) include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe(p$NH_2$)); N-methyl valine (MeVal); homocysteine (hCys), homophenylalanine (hphe) and homoserine (hSer); hydroxyproline (Hyp), homoproline (hPro), N-methylated amino acids and peptoids (N-substituted glycines).

The classifications of the genetically encoded and common non-encoded amino acids according to the categories defined above are summarized in TABLE III, below. It is to be understood that TABLE III is for illustrative purposes only and does not purport to be an exhaustive list of amino acid residues that can be used to substitute the core peptides described herein. Other amino acid residues not specifically mentioned herein can be readily categorized based on their observed physical and chemical properties in light of the definitions provided herein.

TABLE III

CLASSIFICATIONS OF COMMONLY ENCOUNTERED AMINO ACIDS

| Classification | Genetically Encoded | Non-Genetically Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), hPhe |
| Apolar | L, V, I, M, G, A, P | t-BuA, t-BuG, MeIle, Nle, MeVal, Cha, McGly, Aib |
| Aliphatic | A, V, L, I | b-Ala, Dpr, Aib, Aha, MeGly, t-BuA, t-BuG, MetIe, Cha, Nle, MeVal |
| Hydrophilic | | |
| Acidic | D, E | |
| Basic | H, K, R | Dpr, Orn, hArg, Phe(p-NH2), Dbu, Dab |
| Polar | C, Q, N, S, T | Cit, AcLys, MSO, bAla, hSer |
| Helix-Breaking | P, G | D-Pro and other D-amino acids (in L-peptides) |

While in most instances, the amino acids of the core peptides of structure (I) will be substituted with L-enantiomeric amino acids, the substitutions are not limited to L-enantiomeric amino acids. Thus, also included in the definition of "mutated" or "altered" forms are those situations where at least one L-amino acid is replaced with an identical D-amino acid (e.g., L-Arg→D-Arg) or with a D-amino acid of the same category or subcategory (e.g., L-Arg→D-Lys), and vice versa. Indeed, in certain preferred embodiments that are suitable for oral administration to animal subjects, the peptides may advantageously be composed of at least one D-enantiomeric amino acid. Peptides containing such D-amino acids are thought to be more stable to degradation in the oral cavity, gut or serum than are peptides composed exclusively of L-amino acids.

As noted above, D-amino acids tend to disrupt the structure of α-helices when contained at internal positions of an α-helical L-peptide. As a consequence, D-amino acids should not be used to substitute internal L-amino acids; D-amino acid substitutions should be limited to 1–3 amino acid residues at the N-terminus and/or C-terminus of the peptide. Preferably, only the amino acid at the N- and/or C-terminus is substituted with a D-amino acid.

Using the amino acid residue classifications described above in conjunction with the Schiffer-Edmundson helical wheel and helical net diagram presentations of the core peptides of structure (I), as well as the detailed description of the desired properties provided herein, altered or mutated forms of the core peptides of structure (I) that substantially retain the amphipathic and other properties of the helix, and which are therefore considered to be within the scope of the present invention, can be readily obtained.

In a preferred embodiment of the invention, altered or mutated forms of the core peptides of structure (I) are obtained by fixing the hydrophilic or hydrophobic residues according to structure (I) and substituting at least one non-fixed residue with another amino acid, preferably conservatively, i.e., with another amino acid of the same category or sub-category. The residues composing the basic and/or hydrophobic clusters can also be fixed according to structure (I), and at least one non-fixed residue substituted, preferably conservatively.

In another preferred embodiment, altered or mutated forms of the core peptides of structure (I) are obtained by fixing the hydrophilic amino acid residues positioned within the hydrophilic face of the helix according to structure (I) and substituting at least one non-fixed amino acid residue with another amino acid, preferably with another amino acid residue of the same category or sub-category. Referring to FIG. 2A, it can be seen that residues 1, 4, 7, 8, 11, 12, 14, 15 and 18 are positioned within the hydrophilic face of the amphipathic helix formed by the core peptides of structure (I). Of these residues, all are hydrophilic except for residue 1, which may be either hydrophilic or hydrophobic. Thus, in one preferred embodiment, residues 4, 7, 8, 11, 12, 14, 15 and 18 are fixed according to structure (I) and at least one of residues 1, 2, 3, 5, 6, 9, 10, 13, 16 and 17 is substituted with another amino acid of the same category, preferably with another amino acid of the same sub-category. Alternatively, residue 1 is also fixed according to structure (I) and at least one of residues 2, 3, 5, 6, 9, 10, 13, 16 and 17 is substituted.

In a particularly preferred embodiment, the C-terminal basic cluster (residues 14, 16 and 18) is also fixed according to structure (I), and only residues 2, 3, 5, 6, 9, 10, 13 and/or 17 are substituted.

In another particularly preferred embodiment, the hydrophobic cluster (residues 3, 6, 9 and 10) is also fixed according to structure (I), and only residues 2, 5, 13, 16 and/or 17 are substituted.

In still another particularly preferred embodiment, both the basic and hydrophobic clusters are fixed and only residues 2, 5, 13 and/or 17 are substituted.

In another preferred embodiment of the invention, altered or mutated forms of the core peptides of the invention are obtained by fixing the hydrophobic amino acid residues positioned within the hydrophobic face of the helix and substituting at least one non-fixed amino acid residue with another amino acid residue, preferably with another residue of the same category or sub-category.

Referring to FIG. 2A, it can be seen that residues 2, 3, 5, 6, 9, 10, 13, 16 and 17 are positioned within the hydrophobic face. Of these, all are hydrophobic except for residue 16, which is hydrophilic. Thus, in one preferred embodiment residues 2, 3, 5, 6, 9, 10, 13 and 17 are fixed according to structure (I) and at least one of residues 1, 4, 7, 8, 11, 12, 14, 15, 16 and 18 is substituted with another amino acid residue, preferably with another amino acid of the same category or subcategory.

In a particularly preferred embodiment, the C-terminal basic cluster (residues 14, 16 and 18) is also fixed, and only residues 1, 4, 7, 8, 11, 12 and/or 15 are substituted.

In another embodiment, altered or mutated forms of the peptides of structure (I) are obtained by fixing all of the amino acid residues residing within the hydrophobic or hydrophilic face of the helix and substituting, preferably conservatively, at least one amino acid residue residing in the other face with another amino acid residue. The residues comprising the hydrophobic cluster and/or the basic cluster may also be optionally fixed according to structure (I), as previously discussed.

In another embodiment of the invention, the altered or mutated forms of structure (I) are obtained by substituting at least one amino acid with a non-conservative amino acid. Those of skill in the art will recognize that such substitutions should not substantially alter the ainphipathic and/or structural properties of the helix discussed, supra. Thus, in certain instances it may be desirable to substitute one or more pairs of amino acids so as to preserve the net properties of the helix. Further guidance for selecting appropriate amino acid substitutions is provided by the peptide sequences listed in TABLE IX (see. Section 8.3, infra).

In still another embodiment of the invention, the first one to four amino acid residues at the N-terminus and/or C-terminus of the core peptides of structure (I) are substituted with one or more amino acid residues, or one or more peptide segments, that are known to confer stability to regions of α-helical secondary structure ("end-cap" residues or segments). Such end-cap residues and segments are well-known in the art (see, e.g., Richardson and Richardson, 1988, Science 240:1648–1652; Harper et al., 1993, Biochemistry 32(30):7605–7609; Dasgupta and Bell, 1993, Int. J. Peptide Protein Res. 41:499–511; Seale et al., 1994, Protein Science 3:1741–1745; Doig et al., 1994, Biochemistry 33:3396–3403; Zhou et al., 1994, Proteins 18:1–7; Doig and Baldwin, 1995, Protein Science 4:1325–1336; Odaert et al., 1995, Biochemistry 34:12820–12829; Petrukhov et al., 1996, Biochemistry 35:387–397; Doig et al., 1997, Protein Science 6:147–155). Alternatively, the first one to four N-terminal and/or C-terminal amino acid residues of structure (I) can be replaced with peptidomimetic moieties that mimic the structure and/or properties of end-cap residues or segments. Suitable end-cap mimetics are well-known in the art, and are described, for example, in Richardson and Richardson, 1988, Science 240:1648–1652; Harper et al., 1993, Biochemistry 32(30):7605–7609; Dasgupta and Bell, 1993, Int. J. Peptide Protein Res. 41:499–511; Seale et al., 1994, Protein Science 3:1741–1745; Doig et al., 1994, Biochemistry 33:3396–3403; Zhou et al., 1994, Proteins 18:1–7; Doig and Baldwin, 1995, Protein Science 4:1325–1336; Odaert et al., 1995, Biochemistry 34:12820–12829; Petrukhov et al., 1996, Biochemistry 35:387–397; Doig et al., 1997, Protein Science 6:147–155).

While structure (I) contains 18 specified amino acid residue positions, it is to be understood that the core peptides of the invention can contain fewer than 18 amino acid residues. Indeed, truncated or internally deleted forms of structure (I) containing as few as 14–15 amino acid residues that substantially retain the overall characteristics and properties of the amphipathic helix formed by the core peptides of structure (I) are considered to be within the scope of the present invention.

Truncated forms of the peptides of structure (I) are obtained by deleting one or more amino acids from the N- and/or C-terminus of structure (I). Internally deleted forms of structure (I) are obtained by deleting one or more amino acids from internal positions within the peptide of structure (I). The internal amino acid residues deleted may or may not be consecutive residues.

Those of skill in the art will recognize that deleting an internal amino acid residue from a core peptide of structure (I) will cause the plane of the hydrophilic-hydrophobic interface of the helix to rotate by 100° at the point of the deletion. As such rotations can significantly alter the amphipathic properties of the resultant helix, in a preferred embodiment of the invention amino acid residues are deleted so as to substantially retain the alignment of the plane of the hydrophilic-hydrophobic interface along the entire long axis of the helix.

This can be conveniently achieved by deleting a sufficient number of consecutive or non-consecutive amino acid residues such that one complete helical turn is deleted. An idealized α-helix contains 3.6 residues per turn. Thus, in a preferred embodiment, groups of 3–4 consecutive or non-consecutive amino acid residues are deleted. Whether 3 amino acids or 4 amino acids are deleted will depend upon the position within the helix of the first residue to be deleted. Determining the appropriate number of consecutive or non-consecutive amino acid residues that constitute one complete helical turn from any particular starting point within an amphipathic helix is well within the capabilities of those of skill in the art.

Due to the surmised importance of the basic cluster at the C-terminus of the core peptides of structure (I) in stabilizing the helix and the importance of the hydrophobic cluster in effecting lipid binding and LCAT activation, in preferred embodiments of the invention, residues comprising the basic and hydrophobic clusters are not deleted. Thus, in preferred embodiments, residues 14, 16 and 18 (basic cluster) and residues 3, 6, 9 and 10 (hydrophobic cluster) are not deleted.

The core peptides of structure (I) can also be extended at one or both termini or internally with additional amino acid residues that do not substantially interfere with, and in some embodiments even enhance, the structural and/or functional properties of the peptides. Indeed, extended core peptides containing as many as 19, 20, 21, 22 or even more amino acid residues are considered to be within the scope of the present invention. Preferably, such extended peptides will substantially retain the net amphipathicity and other properties of the peptides of structure (I). Of course, it will be recognized that adding amino acids internally will rotate the plane of the hydrophobic-hydrophilic interface at the point of the insertion in a manner similar to that described above for internal deletions. Thus, the considerations discussed above in connection with internal deletions apply to internal additions, as well.

In one embodiment, the core peptides are extended at the N- and/or C-terminus by least one helical turn. Preferably, such extensions will stabilize the helical secondary structure in the presence of lipids, such as the end-cap amino acids and segments previously described.

In a particularly preferred embodiment, the core peptide of structure (I) is extended at the C-terminus by a single basic amino acid residue, preferably Lys (K).

Also included within the scope of the present invention are "blocked" forms of the ApoA-I agonist, i.e., forms of the ApoA-I agonists in which the N- and/or C-terminus is blocked with a moiety capable of reacting with the N-terminal —NH$_2$ or C-terminal —C(O)OH. It has been discovered that removing the N- and/or C-terminal charges of the ApoA-I agonists of the invention containing 18 or fewer amino acid residues (by synthesizing N-acylated peptide amides/ester/hydrazides/alcohols and substitutions thereof) results in agonists which approach, and in some embodiments even exceed, the activity of the unblocked form of the agonist. For example, while peptide 210 (SEQ ID NO:210) exhibits 46% LCAT activation as compared with native ApoA-I, an N- and C-terminal blocked form of this peptide, peptide 193 (SEQ ID NO:193), exhibits 96% LCAT activation in the same assay. In some embodiments containing 22 amino acids, blocking the N- or C-terminus results in ApoA-I agonists which exhibit lower activity than the unblocked forms. However, blocking both the N- and C-termini of ApoA-I agonists composed of 22 amino acids is expected to restore activity. Thus, in a preferred embodiment of the invention, either the N- and/or C-terminus (preferably both termini) of core peptides containing 18 or fewer amino acids are blocked, whereas the N- and C-termini of peptides containing more than 18 amino acids are either both blocked or both unblocked. Typical N-terminal blocking groups include RC(O)—, where R is —H, ($C_1$–$C_6$) alkyl, ($C_1$–$C_6$) alkenyl, ($C_1$–$C_6$) alkynyl, ($C_5$–$C_{20}$) aryl, ($C_6$–$C_{26}$) alkaryl, 5–20 membered heteroaryl or 6–26 membered alkheteroaryl. Preferred N-terminal blocking groups include acetyl, formyl and dansyl. Typical C-terminal blocking groups include —C(O)NRR and —C(O)OR, where each R is independently defined as above. Preferred C-terminal blocking groups include those where each R is independently methyl. While not intending to be bound by any particular theory, it is believed that such terminal blocking groups stabilize the α-helix in the presence of lipids (see, e.g., Venkatachelapathi et al., 1993, PROTEINS: Structure, Function and Genetics 15:349–359).

The native structure of ApoA-I contains eight helical units that are thought to act in concert to bind lipids (Nakagawa et al., 1985, J. Am. Chem. Soc. 107:7087–7092; Ananthara-maiah et al., 1985, J. Biol. Chem. 260:10248–10262; Vanloo et al., 1991, J. Lipid Res. 32:1253–1264; Mendez et al., 1994, J. Clin. Invest. 94:1698–1705; Palgunari et al., 1996, Arterioscler. Thromb. Vasc. Biol. 16:328–338; Demoor et al., 1996, Eur. J. Biochem. 239:74–84). Thus, also included in the present invention are ApoA-I agonists comprised of dimers, trimers, tetramers and even higher order polymers ("multimers") of the core peptides described herein. Such multimers may be in the form of tandem repeats, branched networks or combinations thereof. The core peptides may be directly attached to one another or separated by one or more linkers.

The core peptides that comprise the multimers may be the peptides of structure (I), analogues of structure (I), mutated forms of structure (I), truncated or internally deleted forms of structure (I), extended forms of structure (I) and/or combinations thereof. The core peptides can be connected in a head-to-tail fashion (i.e., N-terminus to C-terminus), a head-to-head fashion, (i.e., N-terminus to N-terminus), a tail-to-tail fashion (i.e., C-terminus to C-terminus), or combinations thereof.

In one embodiment of the invention, the multimers are tandem repeats of two, three, four and up to about ten core peptides. Preferably, the multimers are tandem repeats of from 2 to 8 core peptides. Thus, in one embodiment, the ApoA-I agonists of the invention comprise multimers having the following structural formula:

 (II)

wherein:

each m is independently an integer from 0 to 1, preferably 1;

n is an integer from 0 to 10, preferably 0 to 8;

each "HH" independently represents a core peptide or peptide analogue of structure (I) or a mutated, truncated, internally deleted or extended form thereof as described herein;

each "LL" independently represents a linker; and each "—" independently designates a covalent linkage.

In structure (II), the linker LL can be any bifunctional molecule capable of covalently linking two peptides to one another. Thus, suitable linkers are bifunctional molecules in which the functional groups are capable of being covalently attached to the N- and/or C-terminus of a peptide. Functional groups suitable for attachment to the N- or C-terminus of peptides are well known in the art, as are suitable chemistries for effecting such covalent bond formation.

The linker may be flexible, rigid or semi-rigid, depending on the desired properties of the multimer. Suitable linkers include, for example, amino acid residues such as Pro or Gly or peptide segments containing from about 2 to about 5, 10, 15 or 20 or even more amino acids, bifunctional organic compounds such as $H_2N(CH_2)_nCOOH$ where n is an integer from 1 to 12, and the like. Examples of such linkers, as well as methods of making such linkers and peptides incorporating such linkers are well-known in the art (see, e.g., Hünig et al., 1974, Chem. Ber. 100:3039–3044; Basak et al., 1994, Bioconjug. Chem. 5(4):301–305).

In a preferred embodiment of the invention, the tandem repeats are internally punctuated by a single proline residue. To this end, in those instances where the core peptides are terminated at their N- or C-terminus with proline, such as, e.g., where $X_1$ in structure (I) is Pro (P) or D-Pro (p), m in structure (II) is preferably 0. In those instances where the core peptides do not contain an N- or C-terminal proline, LL is preferably Pro (P) or D-Pro (p) and m is preferably 1.

In certain embodiments of the invention, it may be desirable to employ cleavable linkers that permit the release of one or more helical segments (HH) under certain conditions. Suitable cleavable linkers include peptides having amino acid sequences that are recognized by proteases, oligonucleotides that are cleaved by endonucleases and organic compounds that can be cleaved via chemical means, such as under acidic, basic or other conditions. Preferably, the cleavage conditions will be relatively mild so as not to denature or otherwise degrade the helical segments and/or non-cleaved linkers composing the multimeric ApoA-I agonists.

Peptide and oligonucleotide linkers that can be selectively cleaved, as well as means for cleaving the linkers are well known and will be readily apparent to those of skill in the art. Suitable organic compound linkers that can be selectively cleaved will be apparent to those of skill in the art, and include those described, for example, in WO 94/08051, as well as the references cited therein.

In a preferred embodiment, the linkers employed are peptides that are substrates for endogenous circulatory enzymes, thereby permitting the multimeric ApoA-I agonists to be selectively cleaved in vivo. Endogenous enzymes suitable for cleaving the linkers include, for example, proapolipoprotein A-I propeptidase. Appropriate enzymes, as well as peptide segments that act as substrates for such enzymes, are well-known in the art (see, e.g., Edelstein et al., 1983, J. Biol. Chem. 258:11430–11433; Zanis, 1983, Proc. Natl. Acad. Sci. USA 80:2574–2578).

As discussed above, a key feature of the core peptides of the invention is their ability to form intermolecular hydrogen-bonds or salt bridges when arranged in an anti-parallel fashion. Thus, in a preferred embodiment of the invention, linkers of sufficient length and flexibility are used so as to permit the helical segments (HH) of structure (II) to align in an antiparallel fashion and form intermolecular hydrogen-bonds or salt bridges in the presence of lipids.

Linkers of sufficient length and flexibility include, but are not limited to, Pro (P), Gly (G), Cys-Cys, $H_2N—(CH_2)_n—C(O)OH$ where n is 1 to 12, preferably 4 to 6; $H_2N$-aryl-C(O)OH and carbohydrates.

Alternatively, as the native apolipoproteins permit cooperative binding between antiparallel helical segments, peptide linkers which correspond in primary sequence to the peptide segments connecting adjacent helices of the native apolipoproteins, including, for example, ApoA-I, ApoA-II, ApoA-IV, ApoC-I, ApoC-II, ApoC-III, ApoD, ApoE and ApoJ can be conveniently used to link the core peptides. These sequences are well known in the art (see, e.g., Rosseneu et al., "Analysis of the Primary and of the Secondary Structure of the Apolipoproteins," In: Structure and Function of Lipoproteins, Ch. 6, 159–183, CRC Press, Inc., 1992).

Other linkers which permit the formation of intermolecular hydrogen bonds or salt bridges between tandem repeats of antiparallel helical segments include peptide reverse turns such as β-turns and γ-turns, as well as organic molecules that mimic the structures of peptide β-turns and/or γ-turns. Generally, reverse turns are segments of peptide that reverse the direction of the polypeptide chain so as to allow a single polypeptide chain to adopt regions of antiparallel β-sheet or antiparallel α-helical structure. β-turns generally are composed of four amino acid residues and γ-turns are generally composed of three amino acid residues.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, Adv. Protein Chem. 34:167–339; Rose et al., 1985, Adv. Protein Chem. 37:1–109; Wilmot et al., 1988, J. Mol. Biol. 203:221–232; Sibanda et al., 1989, J. Mol. Biol. 206:759–777; Tramontano et al., 1989, Proteins: Struct. Funct. Genet. 6:382–394).

The specific conformations of short peptide turns such as β-turns depend primarily on the positions of certain amino acid residues in the turn (usually Gly, Asn or Pro). Generally, the type-I β-turn is compatible with any amino acid residue at positions 1 through 4 of the turn, except that Pro cannot occur at position 3. Gly predominates at position 4 and Pro predominates at position 2 of both type-I and type-II turns. Asp, Asn, Ser and Cys residues frequently occur at position 1, where their side chains often hydrogen-bond to the NH of residue 3.

In type-II turns, Gly and Asn occur most frequently at position 3, as they adopt the required backbone angles most easily. Ideally, type-I' turns have Gly at positions 2 and 3, and type-II' turns have Gly at position 2. Type-III turns generally can have most amino acid residues, but type-III' turns usually require Gly at positions 2 and 3. Type-VIa and VIb turns generally have a cis peptide bond and Pro as an internal residue. For a review of the different types and sequences of β-turns in proteins and peptides the reader is referred to Wilmot et al., 1988, J. Mol. Biol. 203:221–232.

The conformation and sequences of many peptide γ-turns have also been well-described in the art (see, e.g., Rose et al., 1985, Adv. Protein Chem. 37:1–109; Wilmer-White et al., 1987, Trends Biochem. Sci. 12:189–192; Wilmot et al., 1988, J. Mol. Biol. 203:221–232; Sibanda et al., 1989, J. Mol. Biol. 206:759–777; Tramontano et al., 1989, Proteins: Struct. Funct. Genet. 6:382–394). All of these types of β-turns and γ-turn structures and their corresponding sequences, as well as later discovered peptide β-turns and γ-turn structures and sequences, are specifically contemplated by the invention.

Alternatively, the linker (LL) may comprise an organic molecule or moiety that mimics the structure of a peptide β-turn or γ-turn. Such β-turn and/or γ-turn mimetic moieties, as well as methods for synthesizing peptides containing such moieties, are well known in the art, and include, among others, those described in Giannis and Kolter, 1993 Angew. Chem. Intl. Ed. Eng. 32:1244–1267; Kahn et al., 1988, J. Molecular Recognition 1:75–79; and Kahn et al., 1987, Tetrahedron Lett. 28:1623–1626.

In still another embodiment of the invention, the multimers are in the form of branched networks (see, e.g., FIG. 7). Such networks are conveniently obtained through the use of multifunction linking moieties that permit more than two helical units to be attached to a simple linking moiety. Thus, branched networks employ molecules having three, four or even more functional groups that are capable of covalently attaching to the N- and/or C-terminus of a peptide. Suitable linking moieties include, for example, amino acid residues having side chains bearing hydroxyl, sulfanyl, amino, carboxyl, amide and/or ester functionalities, such as, for example, Ser (S), Thr (T), Cys (C), Tyr (Y), Asn (N), Gln (Q), Lys (K), Arg (R), Orn, Asp (D) and Glu (E); or other organic molecules containing such functional groups.

The helical segments attached to a single linking moiety need not be attached via like termini. Indeed, in some embodiments the helical segments are attached to a single linking moiety so as to be arranged in an antiparallel fashion, i.e., some of the helices are attached via their N-termini, others via their C-termini.

The helical segments can be attached directly to the linking moiety, or may be spaced from the linking moiety by way of one or more bifunctional linkers (LL), as previously described.

Figure 7A:
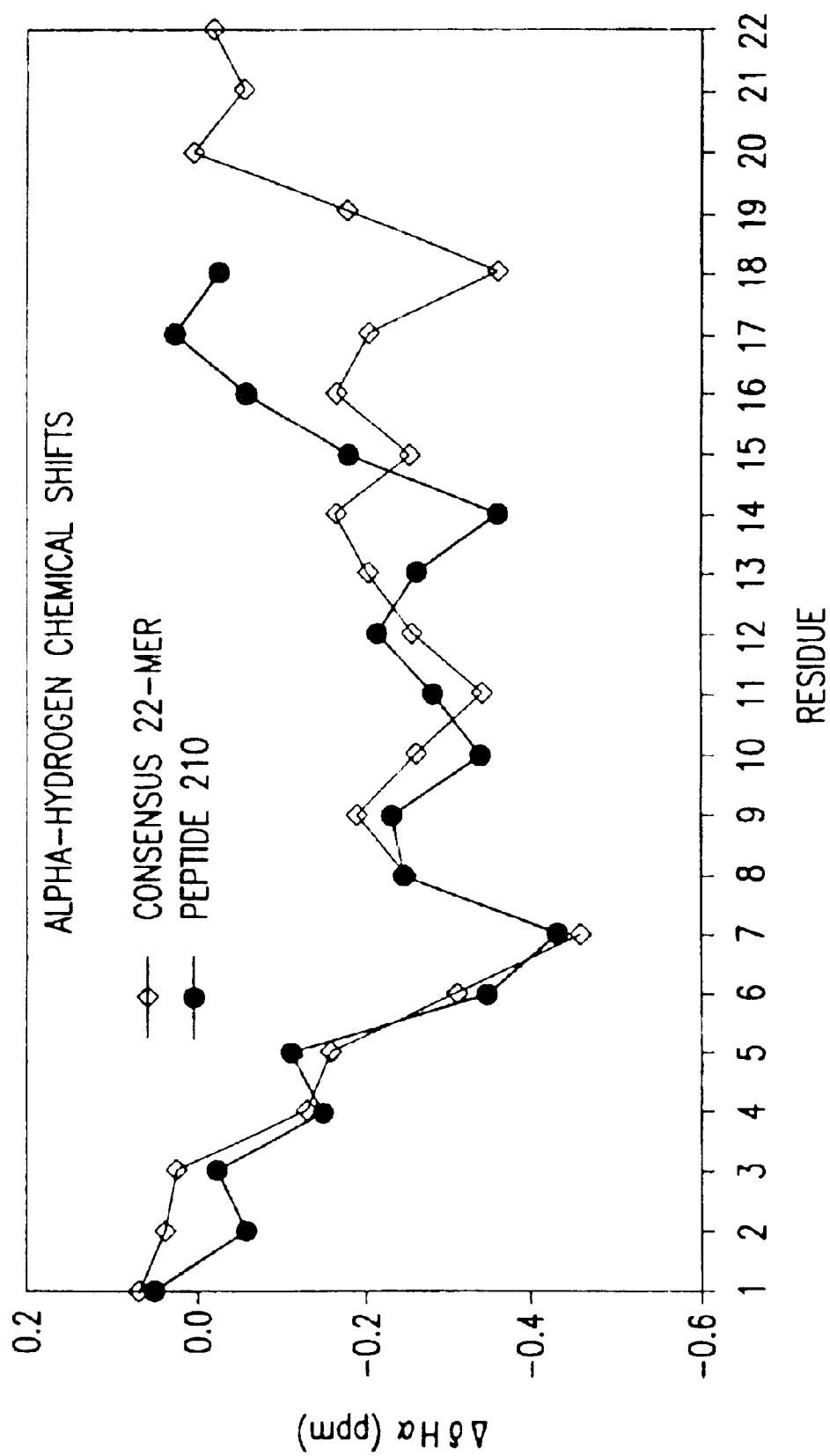
FIG. 7A is a graph illustrating the differences between the observed Hα chemical shifts and the tabulated random coil Hα chemical shifts for peptide 210 (SEQ ID NO:210) and Segrest's consensus 22-mer peptide (SEQ ID NO:75).
Figure 7B:
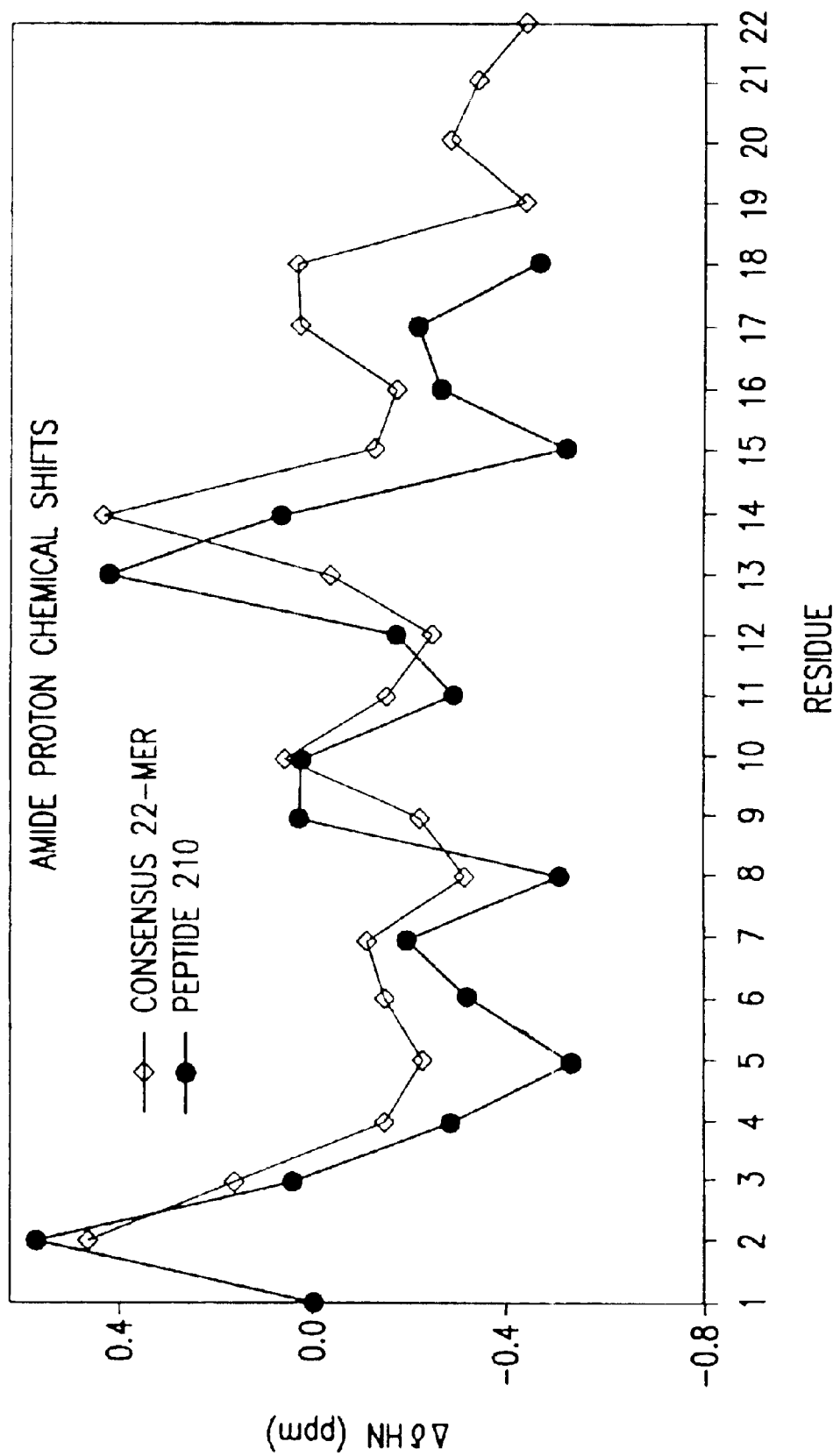
FIG. 7B is a graph illustrating the differences between the observed amide proton chemical shifts and the tabulated random coil amide proton chemical shifts for peptide 210 (SEQ ID NO:210) and Segrest's consensus 22-mer peptide (SEQ ID NO:75).

Referring to FIGS. 7A and 7B, it can be seen that a branched network can be described in terms of the number of "nodes" comprising the network, where each multifunctional linking moiety constitutes a node. In FIGS. 7A and 7B, helical segments (i.e., core peptides of the invention) are illustrated as cylinders, and multifunctional linking moieties (or nodes) as circles (●), where the number of lines emanating from the circle indicates the "order" (or number of functional groups) of the multifunctional linking moiety.

The number of nodes in the network will generally depend on the total desired number of helical segments, and will typically be from about 1 to 2. Of course, it will be appreciated that for a given number of desired helical segments, networks having higher order linking moieties will have fewer nodes. For example, referring to FIGS. 7A and 7B, a tertiary-order network (i.e., a network having trifunctional linking moieties) of seven helical units has three nodes (FIG. 7A), whereas a quaternary order network (i.e., a network having tetrafunctional linking moieties) of seven helical units has only two nodes (FIG. 7B).

The networks may be of uniform order, i.e., networks in which all nodes are, for example, trifunctional or tetrafunctional linking moieties, or may be of mixed order, e.g., networks in which the nodes are mixtures of, for example, trifunctional and tetrafunctional linking moieties. Of course, it is to be understood that even in uniform order networks the linking moieties need not be identical. A tertiary order network may employ, for example, two, three, four or even more different trifunctional linking moieties.

Like the linear multimers, the helical segments comprising the branched network may be, but need not be, identical.

An example of such a mixed order branched network is illustrated in FIG. 7C. In FIG. 7C, helical segments (i.e., core peptides of the invention) are illustrated as cylinders and multifunctional linking moieties as circles (●), where the number of lines emanating from the circle indicates the "order" (or number of functional groups) of the multifunctional linking moiety. Lines connecting helical segments represent bifunctional linkers LL, as previously described. Helical segments which comprise the branched networks may be tandem repeats of core peptides, as previously described.

In one illustrative embodiment, the branched networks of the invention are described by the formula:

(III)

wherein:

each X is independently HH-$(LL_m$—HH-$)_n LL_m$—HH;

each HH is independently a core peptide of structure (I) or an analogue or mutated, truncated, internally deleted or extended form thereof as described herein;

each LL is independently a bifunctional linker;

each m is independently an integer from 0 to 1;

each n is independently an integer from 0 to 8;

$N_{ya}$ and $N_{yb}$ are each independently a multifunctional linking moiety where $y_a$ and $y_b$ represent the number of functional groups on $N_{ya}$ and $N_{yb}$, respectively;

each $y_a$ or $y_b$ is independently an integer from 3 to 8;

p is an integer from 0 to 7; and each "—" independently designates a covalent bond.

In a preferred embodiment, the branched network comprises a "Lys-tree," i.e., a network wherein the multifunctional linking moiety is one or more Lys (K) residues (see, e.g., FIG. 7D).

In one illustrative embodiment, the "Lys tree" branched networks of the invention are described by the formulae:

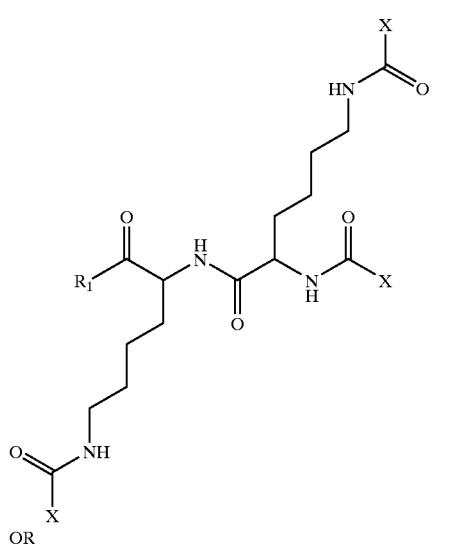

(IV)

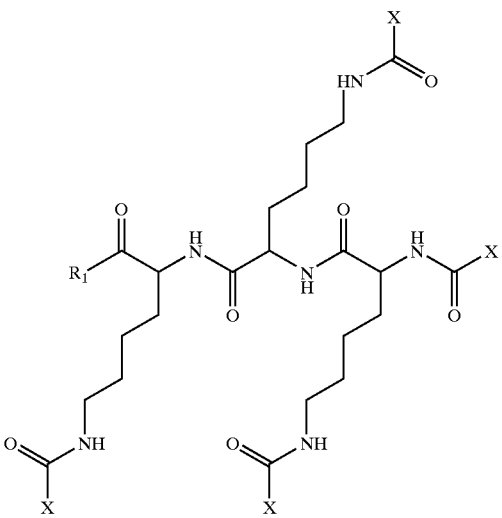

(V)

wherein:

each X is independently HH-$(LL_m$—HH-$)_n LL_m$—HH;

each HH is independently a core peptide or peptide analogue of structure (I) or a mutated, truncated, internally deleted or extended form thereof as described herein;

each LL is independently a bifunctional linker;

each n is independently an integer from 0 to 8;

each m is independently an integer from 0 to 1;

$R_1$ is —OR or —NRR; and each R is independently —H, $(C_1-C_6)$ alkyl, $(C_1-C_6)$ alkenyl, $(C_1-C_6)$ alkynyl; $(C_5-C_{20})$ aryl $(C_6-C_{26})$ alkaryl, 5–20 membered heteroaryl or 6–26 membered alkheteroaryl.

5.1.1. ANALYSIS OF STRUCTURE AND FUNCTION

The structure and function of the core peptides or peptide analogues of the invention, as well as ApoA-I agonists composed of such core peptides, including the multimeric forms described above, can be assayed in order to select active agonists or mimetics of ApoA-I. For example, the core peptides or peptide analogues can be assayed for their ability to form α-helices in the presence of lipids, to bind lipids, to form complexes with lipids, to activate LCAT, to promote cholesterol efflux, etc.

Methods and assays for analyzing the structure and/or function of the peptides are well-known in the art. Preferred methods are provided in the working examples, infra. For example, the circular dichroism (CD) and nuclear magnetic resonance (NMR) assays described in Section 7, infra, can be used to analyze the structure of the peptides or peptide analogues—particularly the degree of helicity in the presence of lipids. The ability to bind lipids can be determined using the fluorescence spectroscopy assay described in Section 7, infra. The ability of the peptides and/or peptide analogues to activate LCAT can be readily determined using the LCAT activation described in Section 8, infra. The in vitro and in vivo assays described in Section 9, 10 and 11, infra, can be used to evaluate the half-life, distribution, cholesterol efflux and effects on RCT.

Generally, core peptides and/or peptide analogues according to the invention which exhibit the properties listed in TABLE IV, infra, are considered to be active.

TABLE IV

PROPERTIES OF ACTIVE PEPTIDES

| PROPERTY | RANGE | PREFERRED RANGE |
|---|---|---|
| % Helicity in the presence of lipids (Ri = 30) (unblocked 22-amino acid residue peptides) | ≧60% | ≧80% |
| % Helicity in the presence of lipids (Ri = 30) (unblocked 18-amino acid residue peptides) | ≧40% | ≧60% |
| % Helicity in the presence of lipids (Ri = 30) (blocked 18-amino acid residue peptides and shorter peptides) | ≧60% | ≧80% |
| Lipid Binding (in the presence of SUVs) | 0.5–10 µM peptide $R_i$ = 1–50 | |
| LCAT activation | ≧38% | ≧80% |

$R_i$ is lipid:peptide molar ratio.

As illustrated in the working examples, infra, core peptides which exhibit a high degree of LCAT activation (≧38%) generally possess significant α-helical structure in the presence of lipidic small unilamellar vesicles (SUVs) (≧60% helical structure in the case of unblocked peptides containing 22 or more amino acid residues and blocked peptides containing 18 or fewer amino acid residues; ≧40% helical structure in the case of unblocked peptides containing 18 or fewer amino acids), and those peptides which exhibit little or no LCAT activation possess little α-helical structure. However, in certain instances, peptides which exhibit significant helical structure in the presence of lipids do not effect significant LCAT.

Similarly, while core peptides that exhibit significant LCAT activation typically bind lipids, in certain instances peptides which exhibit lipid binding do not effect significant LCAT activation.

As a consequence, it will be recognized by those of skill in the art that while the ability of the core peptides described herein to form α-helices (in the presence of lipids) and to bind lipids is critical for activity, in many instances these properties may not be sufficient. Thus, in a preferred embodiment core peptides of the invention are subjected to a series of screens to select for core peptides exhibiting significant pharmacological activity.

In a first step, a core peptide is screened for its ability to form an α-helix in the presence of lipids using the CD assay described in Section 7, infra. Those peptides which are at least 40% helical (unblocked peptides containing 18 or fewer amino acids) or 60% helical (blocked peptides containing 18 or fewer amino acids; unblocked peptides containing 22 or more amino acids) in the presence of lipids (at a conc. of about 5 µM and a lipid:peptide molar ratio of about 30) are then screened for their ability to bind lipids using the fluorescence assay described in Section 7, infra. Of course, only those core peptides which contain a fluorescent Trp (w) or Nal residue are screened for lipid binding via fluorescence. However, for peptides which do not contain fluorescent residues, binding to lipids is obvious when helicity increases in the presence of lipids.

Core peptides which exhibit lipid binding in the presence of SUVs (0.5–10 µM peptide; lipid:peptide molar ratio in the range of 1 to 50) are then screened for pharmacological activity. Of course, the pharmacological activity screened for will depend upon the desired use of the ApoA-I agonists. In a preferred embodiment, the core peptides are screened for their ability to activate LCAT, as peptides which activate LCAT are particularly useful in the methods described herein. Core peptides which exhibit at least about 38% LCAT activation as compared with native human ApoA-I (as determined using the LCAT activation assay described in Section 8, infra), are preferred, with core peptides exhibiting 50%, 60%, 70%, 80% or even 90% or more being particularly preferred.

5.1.2. PREFERRED EMBODIMENTS

The ApoA-I agonists of the invention can be further defined by way of preferred embodiments.

In one preferred embodiment, the ApoA-I agonists are 18 amino acid residue peptides according to structure (I), or the N-terminal acylated and/or C-terminal amidated or esterified forms thereof.

In another preferred embodiment, the ApoA-I agonists are 18 amino acid residue peptides according to structure (I), or the N-terminal acylated and/or C-terminal amidated or esterified forms thereof, in which:

$X_2$ is Ala (A), Val (V) or Leu (L);

$X_4$ is Asp (D) or Glu (E);

$X_7$ is Arg (R), Lys (K) or Orn;

$X_8$ is Asp (D) or Glu (E);

$X_{11}$ is Glu (E) or Asn (N);

$X_{12}$ is Glu (E);

$X_{14}$ is Arg (R), Lys (K), Orn or Leu (L);

$X_{16}$ is Arg (R), Lys (K) or orn; and/or $X_{18}$ is Arg (R), Lys (K) or Orn, and $X_1$, $X_3$, $X_5$, $X_6$, $X_9$, $X_{10}$, $X_{13}$, $X_{15}$ and $X_{17}$ are as previously defined for structure (I).

In another preferred embodiment, the ApoA-I agonists are 18 amino acid residue peptides according to structure (I), or the N-terminal acylated and/or C-terminal amidated or esterified forms thereof, in which when $X_{11}$ is Asn (N), $X_{14}$ is Leu (L) and when $X_{11}$ is other than Asn (N), $X_{14}$ is other than Leu (L). Particularly preferred embodiments according to this aspect of the invention are those peptides, or the N-terminal acylated and/or C-terminal amidated or esterified forms thereof, in which the various $X_n$ in structure (I) are defined as in the preceding paragraph. An exemplary particularly preferred embodiment according to this aspect of the invention is the peptide 209 (PVLDLFRELLNELLQKLK; SEQ ID NO:209), and the N-terminal acylated and/or C-terminal amidated or esterified forms thereof.

In still another preferred embodiment, the ApoA-I agonists are altered or mutated forms of the peptides according to structure (I), or the N-terminal acylated and/or C-terminal amidated or esterified forms thereof, in which $X_1$ is other than Asp (D);

$X_9$ is other than Gly (G);

$X_{10}$ is other than Gly (G)

$X_{12}$ is other than Leu (L); and $X_{13}$ is other than Gly (G).

In still another preferred embodiment, the ApoA-I agonists are selected from the group of peptides set forth below:

| | | |
|---|---|---|
| peptide 191 | PVLDLLRELLEELKQKLK* | (SEQ ID NO:191); |
| peptide 192 | PVLDLFKELLEELKQKLK* | (SEQ ID NO:192); |
| peptide 193 | PVLDLFRELLEELKQKLK* | (SEQ ID NO:193); |
| peptide 194 | PVLELFRELLEELKQKLK* | (SEQ ID NO:194); |
| peptide 195 | PVLELFKELLEELKQKLK* | (SEQ ID NO:195); |
| peptide 196 | PVLDLFRELLEELKNKLK* | (SEQ ID NO:196); |
| peptide 197 | PLLDLFRELLEELKQKLK* | (SEQ ID NO:197); |
| peptide 198 | GVLDLFRELLEELKQKLK* | (SEQ ID NO:198); |
| peptide 199 | PVLDLFRELWEELKQKLK* | (SEQ ID NO:199); |
| peptide 200 | NVLDLFRELLEELKQKLK* | (SEQ ID NO:200); |
| peptide 201 | PLLDLFKELLEELKQKLK* | (SEQ ID NO:201); |
| peptide 202 | PALELFKDLLEELRQKLR* | (SEQ ID NO:202); |
| peptide 203 | AVLDLFRELLEELKQKLK* | (SEQ ID NO:203); |
| peptide 204 | PVLDFFRELLEELKQKLK* | (SEQ ID NO:204); |
| peptide 205 | PVLDLFREWLEELKQKLK* | (SEQ ID NO:205); |
| peptide 206 | PLLELLKELLEELKQKLK* | (SEQ ID NO:206); |
| peptide 207 | PVLELLKELLEELKQKLK* | (SEQ ID NO:207); |
| peptide 208 | PALELFKDLLEELRQRLK* | (SEQ ID NO:208); |
| peptide 209 | PVLDLFRELLEELLQKLK | (SEQ ID NO:209); |
| peptide 210 | PVLDLFRELLEELKQKLK | (SEQ ID NO:210); |
| peptide 211 | PVLDLFRELLEELOQOLO* | (SEQ ID NO:211); |
| peptide 212 | PVLDLFOELLEELOQOLK* | (SEQ ID NO:212); |
| peptide 213 | PALELFKDLLEEFRQRLK* | (SEQ ID NO:213); |
| peptide 214 | pVLDLFRELLEELKQKLK* | (SEQ ID NO:214); |
| peptide 215 | PVLDLFRELLEEWKQKLK* | (SEQ ID NO:215); |
| peptide 230 | PVLELFERLLEDLQKKLK | (SEQ ID NO:230); |
| peptide 231 | PVLDLFRELLEKLEQKLK | (SEQ ID NO:231); |
| peptide 232 | PLLELFKELLEELKQKLK* | (SEQ ID NO:232); | in either the N- and/or C-terminal blocked or unblocked forms.

In still another preferred embodiment, the ApoA-I agonists are selected from the group of peptides set forth below:

| | | |
|---|---|---|
| peptide 191 | PVLDLLRELLEELKQKLK* | (SEQ ID NO:191); |
| peptide 192 | PVLDLFKELLEELKQKLK* | (SEQ ID NO:192); |
| peptide 193 | PVLDLFRELLEELKQKLK* | (SEQ ID NO:193); |
| peptide 194 | PVLELFRELLEELKQKLK* | (SEQ ID NO:194); |
| peptide 195 | PVLELFKELLEELKQKLK* | (SEQ ID NO:195); |
| peptide 196 | PVLDLFRELLEELKNKLK* | (SEQ ID NO:196); |
| peptide 197 | PLLDLFRELLEELKQKLK* | (SEQ ID NO:197); |
| peptide 198 | GVLDLFRELLEELKQKLK* | (SEQ ID NO:198); |
| peptide 199 | PVLDLFRELWEELKQKLK* | (SEQ ID NO:199); |
| peptide 200 | NVLDLFRELLEELKQKLK* | (SEQ ID NO:200); |
| peptide 201 | PLLDLFKELLEELKQKLK* | (SEQ ID NO:201); |
| peptide 202 | PALELFKDLLEELRQKLR* | (SEQ ID NO:202); |
| peptide 203 | AVLDLFRELLEELKQKLK* | (SEQ ID NO:203); |
| peptide 204 | PVLDFFRELLEELKQKLK* | (SEQ ID NO:204); |
| peptide 205 | PVLDLFREWLEELKQKLK* | (SEQ ID NO:205); |
| peptide 206 | PLLELLKELLEELKQKLK* | (SEQ ID NO:206); |
| peptide 207 | PVLELLKELLEELKQKLK* | (SEQ ID NO:207); |
| peptide 208 | PALELFKDLLEELRQRLK* | (SEQ ID NO:208); |
| peptide 209 | PVLDLFRELLNELLQKLK | (SEQ ID NO:209); |
| peptide 210 | PVLDLFRELLEELKQKLK | (SEQ ID NO:210); |
| peptide 211 | PVLDLFRELLEELOQOLO* | (SEQ ID NO:211); |
| peptide 212 | PVLDLFOELLEELOQOLK* | (SEQ ID NO:212); |
| peptide 213 | PALELFKDLLEEFRQRLK* | (SEQ ID NO:213); |
| peptide 214 | pVLDLFRELLEELKQKLK* | (SEQ ID NO:214); |
| peptide 215 | PVLDLFRELLEEWKQKLK* | (SEQ ID NO:215); | in either the N- and/or C-terminal blocked or unblocked forms.

In yet another preferred embodiment, the ApoA-I agonists are multimeric forms according to structures II, III and/or IV in which each HH is independently a peptide according to structure (I) or an N-terminal acylated and/or C-terminal amidated or esterified form thereof, or any of the preferred peptides according to structure (I) described herein.

In yet another preferred embodiment, the core peptides that compose the ApoA-I agonists are not any of the following peptides:

| | | |
|---|---|---|
| peptide 75: | PVLDEFREKLNEELEALKQKLK | (SEQ ID NO:75); |
| peptide 94: | PVLDEFREKLNEALEALKQKLK | (SEQ ID NO:94); |
| peptide 109: | PVLDEFREKLNERLEALKQKLK | (SEQ ID NO:109); |
| peptide 237: | LDDLELQKWAEAFNQLLKK | (SEQ ID NO:237); |
| peptide 238: | EWLKAFYEKVLEKLKELF* | (SEQ ID NO:238); |
| peptide 241: | DWFKAFYDKVFEKFKEFF | (SEQ ID NO:241); |
| peptide 242: | GIKKFLGSIWKFIKAFVG | (SEQ ID NO:242); |
| peptide 243: | DWFKAFYDKVAEKFKEAF | (SEQ ID NO:243); |
| peptide 244: | DWLKAFYDKVAEKLKEAF | (SEQ ID NO:244); |
| peptide 245: | DWLKAFYDKVFEKFKEFF | (SEQ ID NO:245); |
| peptide 246: | EWLEAFYKKVLEKLKELF | (SEQ ID NO:246); |
| peptide 247: | DWFKAFYDKFFEKFKEFF | (SEQ ID NO:247); |
| peptide 248: | EWLKAFYEKVLEKLKELF | (SEQ ID NO:248); |
| peptide 249: | EWLKAEYEKVEEKLKELF* | (SEQ ID NO:249); |
| peptide 250: | EWLKAEYEKVLEKLKELF* | (SEQ ID NO:250); and |
| peptide 251: | EWLKAFYKKVLEKLKELF* | (SEQ ID NO:251). |

In a final preferred embodiment, the ApoA-I agonists are not any of the peptides listed in TABLE IX (Section 8.3, infra) which exhibit an LCAT activation activity of less than 38% as compared with native human ApoA-I.

5.2 SYNTHESIS AND PURIFICATION OF THE ApoA-I PEPTIDE AGONSITS

The core peptides of the invention may be prepared using virtually any art-known technique for the preparation of peptides. For example, the peptides may be prepared using conventional step-wise solution or solid phase peptide syntheses, or recombinant DNA techniques.

5.2.1 CHEMICAL SYNTHESIS

Core peptides may be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides of the invention may be prepared by way of segment condensation, as described, for example, in Liu et al., 1996, Tetrahedron Lett. 37(7): 933–936; Baca, et al., 1995, J. Am. Chem. Soc. 117:1881–1887; Tam et al., 1995, Int. J. Peptide Protein Res. 45:209–216; Schnölzer and Kent, 1992, Science 256:221–225; Liu and Tam, 1994, J. Am. Chem. Soc. 116(10):4149–4153; Liu and Tam, 1994, Proc. Natl. Acad. Sci. USA 91:6584–6588; Yamashiro and Li, 1988, Int. J. Peptide Protein Res. 31:322–334). Segment condensation is a particularly useful method for synthesizing embodiments containing internal glycine residues. Other methods useful for synthesizing the peptides of the invention are described in Nakagawa et al., 1985, J. Am. Chem. Soc. 107:7087–7092.

ApoA-I agonists containing N- and/or C-terminal blocking groups can be prepared using standard techniques of organic chemistry. For example, methods for acylating the N-terminus of a peptide or amidating or esterifying the C-terminus of a peptide are well-known in the art. Modes of carrying other modifications at the N- and/or C-terminus will be apparent to those of skill in the art, as will modes of protecting any side-chain functionalities as may be necessary to attach terminal blocking groups.

Pharmaceutically acceptable salts (counter ions) can be conveniently prepared by ion-exchange chromatography or other methods as are well known in the art.

Compounds of the invention which are in the form of tandem multimers can be conveniently synthesized by adding the linker(s) to the peptide chain at the appropriate step in the synthesis. Alternatively, the helical segments can be synthesized and each segment reacted with the linker. Of course, the actual method of synthesis will depend on the composition of the linker. Suitable protecting schemes and chemistries are well known, and will be apparent to those of skill in the art.

Compounds of the invention which are in the form of branched networks can be conveniently synthesized using the trimeric and tetrameric resins and chemistries described in Tam, 1988, Proc. Natl. Acad. Sci. USA 85:5409–5413 and Demoor et al., 1996, Eur. J. Biochem. 239:74–84. Modifying the synthetic resins and strategies to synthesize branched networks of higher or lower order, or which contain combinations of different core peptide helical segments, is well within the capabilities of those of skill in the art of peptide chemistry and/or organic chemistry.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam et al., 1979, Synthesis 955–957; Stewart et al., 1984, Solid Phase Peptide Synthesis, 2d Ed., Pierce Chemical Company Rockford, Ill.; Ahmed et al., 1975, J. Biol. Chem. 250:8477–8482; and Pennington et al., 1991 Peptides 1990 164–166, Giralt and Andreu, Eds., ESCOM Leiden, The Netherlands. An additional alternative is described by Kamber et al., 1980, Helv. Chim. Acta 63:899–915. A method conducted on solid supports is described by Albericio, 1985, Int. J. Peptide Protein Res. 26:92–97. Any of these methods may be used to form disulfide linkages in the peptides of the invention.

5.2.2 RECOMBINANT SYNTHESIS

If the peptide is composed entirely of gene-encoded amino acids, or a portion of it is so composed, the peptide or the relevant portion may also be synthesized using conventional recombinant genetic engineering techniques.

For recombinant production, a polynucleotide sequence encoding the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

To increase efficiency of production, the polynucleotide can be designed to encode multiple units of the peptide separated by enzymatic cleavage sites—either homopolymers (repeating peptide units) or heteropolymers (different peptides strung together) can be engineered in this way. The resulting polypeptide can be cleaved (e.g., by treatment with the appropriate enzyme) in order to recover the peptide units. This can increase the yield of peptides driven by a single promoter. In a preferred embodiment, a polycistronic polynucleotide can be designed so that a single mRNA is transcribed which encodes multiple peptides (i.e., homopolymers or heteropolymers) each coding region operatively linked to a cap-independent translation control sequence; e.g., an internal ribosome entry site (IRES). When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843) or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

In one insect expression system that may be used to produce the peptides of the invention, *Autographa californica*, nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., see Smith et al., 1983, J. Virol. 46:584; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. (USA) 81:3655–3659). Alternatively, the vaccinia 7.5 K promoter may be used, (see, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Other expression systems for producing the peptides of the invention will be apparent to those having skill in the art.

5.2.3 PURIFICATION OF PEPTIDES

The peptides of the invention can be purified by art-known techniques such as reverse phase chromatography high performance liquid chromatography, ion exchange chromatography, gel electrophoresis, affinity chromatography and the like. The actual conditions used to purify a particular peptide will depend, in part, on synthesis strategy and on factors such as net charge, hydrophobicity, hydrophilicity, etc., and will be apparent to those having skill in the art. Multimeric branched peptides can be purified, e.g., by ion exchange or size exclusion chromatography.

For affinity chromatography purification, any antibody which specifically binds the peptide may be used. For the production of antibodies, various host animals, including but not limited to rabbits, mice, rats, etc., may be immunized by injection with a peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Kohler and Milstein, 1975, Nature 256:495–497, or Kaprowski, U.S. Pat. No. 4,376,110 which is incorporated by reference herein; the human B-cell hybridoma technique) Kosbor et al., 1983, Immunology Today 4:72; Cote et al., 1983, Proc. Natl. Acad. Sci. U.S.A. 80:2026–2030); and the EBV-hybridoma technique (Cole et al., 1985, Monoclonal Antibodies and Cancer Therapy, Alan R. Liss, Inc., pp. 77–96 (1985)). In addition, techniques developed for the production of "chimeric antibodies" Morrison et al., 1984, Proc. Natl. Acad. Sci. U.S.A. 81:6851–6855; Neuberger et al., 1984, Nature 312:604–608; Takeda et al., 1985, Nature 314:452–454, Boss, U.S. Pat.

No. 4,816,397; Cabilly, U.S. Pat. No. 4,816,567; which are incorporated by reference herein) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089 which is incorporated by reference herein). Alternatively, techniques described for the production of single chain antibodies (U.S. Pat. No. 4,946,778) can be adapted to produce peptide-specific single chain antibodies.

Antibody fragments which contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., 1989, Science 246:1275–1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, Protein Purification: Principles and Practice, Springer-Verlag New York, Inc., NY, Livingstone, 1974, Methods In Enzymology: Immunoaffinity Chromatography of Proteins 34:723–731.

5.3 PHARMACEUTICAL FORMULATIONS AND METHODS OF TREATMENT

The ApoA-I agonists of the invention can be used to treat any disorder in animals, especially mammals including humans, for which increasing serum HDL concentration, activating LCAT, and promoting cholesterol efflux and RCT is beneficial. Such conditions include, but are not limited to hyperlipidemia, and especially hypercholesterolemia, and cardiovascular disease such as atherosclerosis (including treatment and prevention of atherosclerosis); restenosis (e.g., preventing or treating atherosclerotic plaques which develop as a consequence of medical procedures such as balloon angioplasty); and other disorders, such as endotoxemia, which often results in septic shock.

The ApoA-I agonists can be used alone or in combination therapy with other drugs used to treat the foregoing conditions. Such therapies include, but are not limited to simultaneous or sequential administration of the drugs involved.

For example, in the treatment of hypercholesterolemia or atherosclerosis, the ApoA-I agonist formulations can be administered with any one or more of the cholesterol lowering therapies currently in use; e.g., bile-acid resins, niacin, and/or statins. Such a combined regimen may produce particularly beneficial therapeutic effects since each drug acts on a different target in cholesterol synthesis and transport; i.e., bile-acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the ApoA-I agonists affect RCT, increase HDL, increase LCAT activity and promote cholesterol efflux.

In another embodiment, the ApoA-I agonists may be used in conjunction with fibrates to treat hyperlipidemia, hypercholesterolemia and/or cardiovascular disease such as atherosclerosis.

In yet another embodiment, the ApoA-I agonists of the invention can be used in combination with the antimicrobials and anti-inflammatory agents currently used to treat septic shock induced by endotoxin.

The ApoA-I agonists of the invention can be formulated as peptides or as peptide-lipid complexes which can be administered to subjects in a variety of ways to deliver the ApoA-1 agonist to the circulation. Exemplary formulations and treatment regimens are described below.

5.3.1 ApoA-I AGONISTS AND PEPTIDE/LIPID COMPLEX AS THE ACTIVE INGREDIENT

The ApoA-I agonist peptides can be synthesized or manufactured using any technique described in Section 5.2 and its subsections. Stable preparations which have a long shelf life may be made by lyophilizing the peptides—either to prepare bulk for reformulation, or to prepare individual aliquots or dosage units which can be reconstituted by rehydration with sterile water or an appropriate sterile buffered solution prior to administration to a subject.

In certain embodiments, it may be preferred to formulate and administer the ApoA-I agonist in a peptide-lipid complex. This approach has several advantages since the complex should have an increased half-life in the circulation, particularly when the complex has a similar size and density to HDL, and especially the pre-β-1 or pre-β-2 HDL populations. The peptide-lipid complexes can conveniently be prepared by any of a number of methods described below. Stable preparations having a long shelf life may be made by lyophilization—the co-lyophilization procedure described below being the preferred approach. The lyophilized peptide-lipid complexes can be used to prepare bulk for pharmaceutical reformulation, or to prepare individual aliquots or dosage units which can be reconstituted by rehydration with sterile water or an appropriate buffered solution prior to administration to a subject.

A variety of methods well known to those skilled in the art can be used to prepare the peptide-lipid vesicles or complexes. To this end, a number of available techniques for preparing liposomes or proteoliposomes may be used. For example, the peptide can be cosonicated (using a bath or probe sonicator) with appropriate lipids to form complexes. Alternatively the peptide can be combined with preformed lipid vesicles resulting in the spontaneous formation of peptide-lipid complexes. In yet another alternative, the peptide-lipid complexes can be formed by a detergent dialysis method; e.g., a mixture of the peptide, lipid and detergent is dialyzed to remove the detergent and reconstitute or form peptide-lipid complexes (e.g., see Jonas et al., 1986, Methods in Enzymol. 128:553–582).

While the foregoing approaches are feasible, each method presents its own peculiar production problems in terms of cost, yield, reproducibility and safety. The applicants have developed a simple method for preparing peptide or protein-phospholipid complexes which have characteristics similar to HDL. This method can be used to prepare the ApoA-I peptide-lipid complexes, and has the following advantages: (1) Most or all of the included ingredients are used to form the designed complexes, thus avoiding waste of starting material which is common to the other methods. (2) Lyophilized compounds are formed which are very stable during storage. The resulting complexes may be reconstituted immediately before use. (3) The resulting complexes usually need not be further purified after formation and before use. (4) Toxic compounds, including detergents such as cholate, are avoided. Moreover, the production method can be easily scaled up and is suitable for GMP manufacture (i.e., in an endotoxin-free environment).

In accordance with the preferred method, the peptide and lipid are combined in a solvent system which co-solubilizes each ingredient and can be completely removed by lyophilization. To this end, solvent pairs must be carefully selected to ensure co-solubility of both the amphipathic peptide and the lipid. In one embodiment, the protein(s) or peptide(s) to be incorporated into the particles can be dissolved in an aqueous or organic solvent or mixture of solvents (solvent 1). The (phospho)lipid component is dissolved in an aqueous or organic solvent or mixture of solvents (solvent 2) which is miscible with solvent 1, and the two solutions are mixed. Alternatively, the peptide and lipid can be incorporated into a co-solvent system; i.e., a mixture of the miscible solvents. A suitable proportion of peptide (protein) to lipids is first determined empirically so that the resulting complexes possess the appropriate physical and chemical properties; i.e., usually (but not necessarily) similar in size to HDL. The resulting mixture is frozen and lyophilized to dryness. Sometimes an additional solvent must be added to the mixture to facilitate lyophilization. This lyophilized product can be stored for long periods and will remain stable.

In the working examples describe infra, the peptide 210 (SEQ ID NO:210) and phospholipids were dissolved separately in methanol, combined, then mixed with xylene before lyophilization. The peptide and lipid can both be added to a mixture of the two solvents. Alternatively, a solution of the peptide dissolved in methanol can be mixed with a solution of lipid dissolved in xylene. Care should be taken to eliminate salt from the solvent system in order to avoid salting out the peptide. The resulting solution containing the peptide and lipid cosolubilized in methanol/xylene is lyophilized to form a powder.

The lyophilized product can be reconstituted in order to obtain a solution or suspension of the peptide-lipid complex. To this end, the lyophilized powder is rehydrated with an aqueous solution to a suitable volume (often 5 mgs peptide/ml which is convenient for intravenous injection). In a preferred embodiment the lyophilized powder is rehydrated with phosphate buffered saline or a physiological saline solution. The mixture may have to be agitated or vortexed to facilitate rehydration, and in most cases, the reconstitution step should be conducted at a temperature equal to or greater than the phase transition temperature of the lipid component of the complexes. Within minutes, a clear preparation of reconstituted lipid-protein complexes results.

An aliquot of the resulting reconstituted preparation can be characterized to confirm that the complexes in the preparation have the desired size distribution; e.g., the size distribution of HDL. Gel filtration chromatography can be used to this end. In the working examples described infra, a Pharmacia Superose 6 FPLC gel filtration chromatography system was used. The buffer used contains 150 mM NaCl in 50 mM phosphate buffer, pH 7.4. A typical sample volume is 20 to 200 microliters of complexes containing 5 mgs peptide/ml. The column flow rate is 0.5 mls/min. A series of proteins of known molecular weight and Stokes' diameter as well as human HDL are used as standards to calibrate the column. The proteins and lipoprotein complexes are monitored by absorbance or scattering of light of wavelength 254 or 280 nm.

The ApoA-I agonists of the invention can be complexed with a variety of lipids, including saturated, unsaturated, natural and synthetic lipids and/or phospholipids. Suitable lipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, sphingomyelin, sphingolipids, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3) diglyceride, aminophenylglycoside, 3-cholesteryl-6'-(glycosylthio)hexyl ether glycolipids, and cholesterol and its derivatives.

The Applicants have discovered that when the ApoA-I agonists of the invention are complexed with sphingomyelin, all of the HDL of the pre-β-like particles is removed. Accordingly, in a preferred embodiment of the invention, the ApoA-I agonists are administered as a complex with sphingomyelin.

5.3.2 METHODS OF THE TREATMENT

The ApoA-I peptide agonists or peptide-lipid complexes of the invention may be administered by any suitable route that ensures bioavailability in the circulation. This can best be achieved by parenteral routes of administration, including intravenous (IV), intramuscular (IM), intradermal, subcutaneous (SC) and intraperitoneal (IP) injections. However, other routes of administration may be used. For example, absorption through the gastrointestinal tract can be accomplished by oral routes of administration (including but not limited to ingestion, buccal and sublingual routes) provided appropriate formulations (e.g., enteric coatings) are used to avoid or minimize degradation of the active ingredient, e.g., in the harsh environments of the oral mucosa, stomach and/or small intestine. Alternatively, administration via mucosal tissue such as vaginal and rectal modes of administration may be utilized to avoid or minimize degradation in the gastrointestinal tract. In yet another alternative, the formulations of the invention can be administered transcutaneously (e.g., transdermally), or by inhalation. It will be appreciated that the preferred route may vary with the condition, age and compliance of the recipient.

The actual dose of ApoA-I agonists or peptide-lipid complex used will vary with the route of administration, and should be adjusted to achieve circulating plasma concentrations of 100 mg/l to 2 g/l. Data obtained in animal model systems described herein show that the ApoA-I agonists of the invention associate with the HDL component, and have a projected half-life in humans of about five days. Thus, in one embodiment, the ApoA-I agonists can be administered by injection at a dose between 0.5 mg/kg to 100 mg/kg once a week. In another embodiment, desirable serum levels may be maintained by continuous infusion or by intermittent infusion providing about 0.5 mg/kg/hr to 100 mg/kg/hr.

Toxicity and therapeutic efficacy of the various ApoA-I agonists can be determined using standard pharmaceutical procedures in cell culture or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. ApoA-I peptide agonists which exhibit large therapeutic indices are preferred.

5.3.3 PHARMACEUTICAL FORMULATIONS

The pharmaceutical formulation of the invention contain the ApoA-I peptide agonist or the peptide-lipid complex as the active ingredient in a pharmaceutically acceptable carrier suitable for administration and delivery in vivo. As the peptides may contain acidic and/or basic termini and/or side chains, the peptides can be included in the formulations in either the form of free acids or bases, or in the form of pharmaceutically acceptable salts.

Injectable preparations include sterile suspensions, solutions or emulsions of the active ingredient in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the ApoA-I agonist may be lyophilized, or the co-lyophilized peptide-lipid complex may be prepared. The stored preparations can be supplied in unit dosage forms and reconstituted prior to use in vivo.

For prolonged delivery, the active ingredient can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt form of the ApoA-I agonist.

Alternatively, transdermal delivery systems manufactured as an adhesive disc or patch which slowly releases the active ingredient for percutaneous absorption may be used. To this end, permeation enhancers may be used to facilitate transdermal penetration of the active ingredient. A particular benefit may be achieved by incorporating the ApoA-I agonists of the invention or the peptide-lipid complex into a nitroglycerin patch for use in patients with ischemic heart disease and hypercholesterolemia.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner. For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.4 OTHER USES

The ApoA-I agonists of the invention can be used in assays in vitro to measure serum HDL, e.g., for diagnostic purposes. Because the ApoA-I agonists associate with the HDL component of serum, the agonists can be used as "markers" for the HDL population. Moreover, the agonists can be used as markers for the subpopulation of HDL that are effective in RCT. To this end, the agonist can be added to or mixed with a patient serum sample; after an appropriate incubation time, the HDL component can be assayed by detecting the incorporated ApoA-I agonist. This can be accomplished using labeled agonists (e., radiolabels, fluorescent labels, enzyme labels, dyes, etc.), or by immunoassays using antibodies (or antibody fragments) specific for the agonist.

Alternatively, labeled agonist can be used in imaging procedures (e.g., CAT scans, MRI scans) to visualize the circulatory system, or to monitor RCT, or to visualize accumulation of HDL at fatty streaks, atherosclerotic lesions, etc. (where the HDL should be active in cholesterol efflux).

6. EXAMPLE

Synthesis of Peptide Agonists of ApoA-I

The peptides described in TABLE IX (Section 8.3, infra) were synthesized and characterized as described in the subsections below. The peptides were also analyzed structurally and functionally as described in Sections 7 and 8, infra.

6.1 SYNTHESIS OF CORE PEPTIDES

Peptides were synthesized on solid phase according to the Merrifield technique (Merrifield, 1969, J. Am. Chem. Soc.

85:2149–2154) using 0.25 mmol p-alkoxybenzylalcohol resin (HMP resin) (Wang, 1973, J. Am. Chem. Soc. 95:1328–1333) and Fmoc chemistry. All syntheses were carried out on an Applied Biosystems ABI model 430A automated peptide synthesizer (Perkin-Elmer, Foster City, Calif.). The salvation and activation times used for each coupling cycle are shown in TABLE V below:

TABLE V

SINGLE COUPLE ACTIVATOR CYCLES

| CYCLE NAME | DESIGNATED AMINO ACIDS | DISSOLVING SOLVENT | TIME | ACTIVATION TIME | TRANSFER TIMES* |
|---|---|---|---|---|---|
| afmc 31 | Asn(trt), His(trt), Lys(Boc),Trp | ~0.4 ml DCM ~1.2 ml NMP ~1.0 ml HOBt/NMP | ~7 min. | ~51. min. | 1 = 50 sec. 2 = 36 sec. |
| afmc 32 | Arg(Pmc), Gln(trt),Aib | ~0.8 ml DCM ~1.2 ml NMP ~1.0 ml HOBt/NMP | ~32 min. | ~51 min. | 1 = 60 sec. 2 = 40 sec. |
| afmc 33 | Ala,Asp(OtBu), Glu(OtBu),Gly, Ile,Leu, Met, Phe, Pro | ~0.4 ml DCM ~0.8 ml NMP ~0.1 ml HOBt/NMP | ~4 min. | ~36.5 min. | 1 = 38 sec. 2 = 27 sec. |
| afmc 34 | Val | ~0.4 ml DCM ~0.8 ml NMP ~0.1 ml HOBt/NMP | ~4 min. | ~61.5 min. | 1 = 38 sec. 2 = 27 sec. |

*1 = Transfer from Cartridge to Activator.
 2 = Transfer from Activator to Cartridge.
DCC is dicyclohexylcarbodiimide
BOC is t-butyloxycarbonyl
HOBt is 1-hydroxybenzotriazole
Pmc is pentamethylchroman-6-sulfonyl
NMP is N-methylpyrrolidone
OtBu is t-butyl ester
trt is trityl The resins were washed with NMP between each coupling step. The protocol for one synthesis cycle is shown below in TABLE VI:

TABLE VI

COUPLING PROTOCOL FOR ONE SYNTHESIS CYCLE

| | OPERATION | TIME (min.) |
|---|---|---|
| 1. | Deprotection (10% piperdine in NMP) | 20 |
| 2. | Wash (NMP) | 5 |
| 3. | Couple (4 equiv. Fmoc-amino acid-HOBT ester in NMP, preactivated 50 min.) | 61 |
| 4. | Wash | 3 |
| 5. | Resin Sample (optional) | 3 |
| | TOTAL | 92 |

All amino acids except Fmoc-β-(1-naphthyl)alanine were coupled in this manner. Fmoc-β-(1-naphthyl)alanine was coupled manually. For manual coupling, 1 mmol Fmoc-β-(1-naphthyl)alanine and 1 mmol 2-(1H-benzotriazole-1-yl)-1,1,3,3-tetramethyluronium tetrafluoroborate (TBTU) were dissolved in 5 ml NMP and mixed with the peptide-resin. Thereafter, 2 mmol of N-ethyldiisopropylamine were added, the mixture shaken for 2 hours and the peptide-resin washed 6 times with 10 ml NMP. The coupling efficiency was monitored using the Kaiser Test (Kaiser, 1970, Anal. Biochem. 34:59577), and the coupling repeated if necessary. After coupling of naphthylalanine, the remainder of the synthesis was performed automatically as described above.

6.2 SYNTHESIS OF PEPTIDE AMIDES

Where indicated in TABLE IX (Section 8.3, infra), peptide amides were synthesized using a Rink amide resin containing the Fmoc-Rink amide handle 4-(2',4'-dimethylphenyl)-Fmoc-phenoxymethyl (Rink, 1987, Tetrahedron Lett. 28: 3787–3790) and the synthesis protocols described in section 6.1, supra.

6.3 SYNTHESIS OF N-TERMINAL ACYLATED PEPTIDES

Where indicated in TABLE IX (section 8.3, infra), N-terminal acylated forms of the peptides were prepared by exposing the resin-bound peptide prepared as described in section 6.1 or 6.2, supra, to an appropriate acylating agent.

For N-terminal acetylated peptides, 15 ml of acetic anhydride solution (10% v/v in NMP) was added to each 1 g of resin-bound peptide, the mixture shaken for 5 min. and the resin recovered by filtration. The recovered resin was washed three times with NMP (15 ml) and three times with ethanol (15 ml).

6.4 CLEAVAGE AND DEPROTECTION

Following synthesis, the peptides described in Sections 6.1, 6.2 and 6.3, supra, were cleaved from the resin and deprotected with a cleavage solution containing 92.5% trifluroacetic acid (TFA)/3.75% anisole/3.75% dodecanthiol (v/v/v). To effect cleavage, 10 ml of cleavage solution was added to 0.25 mmol peptide resin and stirred for 1.5 hours at room temperature. The resin was removed via filtration and the cleaved/deprotected peptide precipitated with diethyl ether, washed with ether and dried in vacuo.

The cleavage cocktail for peptides containing Trp (W), as well as for peptide amides, was composed of 86.5% TFA, 4.5% $H_2O$, 4.5% 1,2-ethanedithiol, 4.5% anisole and 3% phenol.

6.5 PURIFICATION

The crude, cleaved peptides of Section 6.4 were purified by reverse phase HPLC. The purity of each peptide was confirmed by different analytical techniques (analytical HPLC, capillary electrophoresis). Capillary electrophoreses were carried out on fused silica capillaries of 70 cm length and an internal diameter of 75 μm (Thermo Separation Products). The separations were performed at 25° C., 15 kV, run time 35 min., in two different buffer systems: Buffer 1 (20 mM $Na_2B_4O_7$, pH 9.2) and Buffer 2 (10 mM $Na_2HPO_4$, pH 2.5). HPLC separations were carried out on Nucleosil 7C18 or Nucleosil 7C4 columns (Macherey and Nagel, Germany), 250×21 mm, at a flow rate of 8 ml/min. The gradient elution was performed using a mixture of 0.1% TFA in water (Solvent A) and 0.1% TFA in acetonitrile (Solvent B). The gradients used were adjusted to meet the needs of each peptide.

6.6 CHARACTERIZATION

The mass and amino acid analysis of the purified peptides described in Section 6.5 were confirmed via mass spectrometry and amino acid analysis, respectively, as described below. Edman degradation was used for sequencing.

6.6.1 LC-MS

A standard commercially available triple stage quadruple mass spectrometer (model TSQ 700; Finnigan MAT, San Jose Calif., USA) was used for mass determination. A pneumatically assisted electrospray (ESI) interface was used for sample introduction to the atmospheric pressure ionization source of the mass spectrometer. The interface sprayer was operated at a positive potential of 4.5 kV. The temperature of the steel capillary was held at 200° C. whereas the manifold was at 70° C. Positive ions generated by this ion evaporation process entered the analyzer of the mass spectrometer. The multiplier was adjusted to 1000 V. The analyzer compartment of the mass spectrometer was at 4E-6. All acquisitions were performed at resolution <1u.

Peptides were analyzed by direct infusion of the purified peptides using an ABI (Applied Biosystems) microbore system consisting of a syringe pump (model 140B), an UV detector (model 785A) and an oven/injector (model 112A). The solvent system consisted of water (solvent A) and acetonitrile (solvent B), each containing 0.1% TFA. Peptides were infused using either a gradient or isocratic conditions and eluted from an Aquapore $C_{18}$ column. The flow rate was typically 300 μl/min. Concentration of each peptide was about 0.03 mg/ml, 20 μl of which was injected (e.g., 30 pmol).

Full scan MS experiments were obtained by scanning quadruple 1 from m/z 500–1500 in 4s. Data were acquired using an Alpha DEC station and were processed using the software package provided by Finnigan MAT (BIOWORKS).

6.6.2 AMINO ACID ANALYSIS

Amino acid analysis was performed on an ABI (Applied Biosystems) 420 Amino Acid Analyzer. This system consists of three modules: a hydrolysis and derivatisation instrument, a reverse-phase HPLC and a data system. Peptide sample were applied (3 times in triplicate) on porous glass slides and subsequently hydrolyzed under gas phase conditions (155° C., 90 min.). After removal of the HCL, the resulting amino acids were converted to PTC-AA (Phenylthiocarbamoyl-amino acids) using PITC (Phenylisothiocyanate). After transfer to the HPC sample loop the resulting mixtures were fractionated on an Aquapore C18 column using the gradient mode (Solvent A: 50 mmol ammonium acetate ($NH_4Ac$), pH 5.4, in water; Solvent B: 32 mmol of sodium acetate (NaOAc) in aqueous acetonitrile) under conditions of temperature control. The HPLC data were processed by the software package provided by Applied Biosystems. Quantification was performed relative to a peptide standard delivered by Applied Biosystems.

6.7 SYNTHESIS OF BRANCHED NETWORKS

Tetrameric-core peptidyl resin and trimeric-core peptidyl resin are synthesized as described in Demoor et al., 1996, Eur. J. Biochem. 239:74–84. The tetrameric and trimeric core matrix still linked to the 4-methyl benzhydrylamine resin is then used as initial peptidyl-resin for automated synthesis of core peptides as previously described.

Branched networks containing helical segments of different amino acid compositions can be synthesized using orthogonal synthesis and protecting strategies well known in the art.

7. EXAMPLE

Structural and Lipid Binding Analysis of ApoA-I Peptides

The structural and lipid binding characteristics of the purified peptides synthesized as described in Section 6, supra, were determined by circular dichroism (CD), fluorescence spectroscopy and nuclear magnetic resonance (NMR).

7.1 CIRCULAR DICHROISM

This Example describes a preferred method for determining the degree of helicity of the core peptides of the invention both free in buffer and in the presence of lipids.

7.1.1 EXPERIMENTAL METHOD

Far UV circular dichroism spectra were recorded between 190 and 260 nm (in 0.5 nm or 0.2 nm increments) with a AVIV62DS spectrometer (AVIV Associates, Lakewood, N.J., USA) equipped with a thermoelectric cell holder and sample changer. The instrument was calibrated with (+)-10-camphoric acid. Between one and three scans were collected for each sample, using 10 cm, 5 cm, 1 cm and 0.1 cm path length quartz Suprasil cells, respectively, for peptide concentrations of $10^{-7}$ M to $10^{-4}$ M. The bandwidth was fixed at 1.5 nm and the scan speed to 1s per wavelength step. The reported data are the mean of at least 2 or 3 independent measurements.

After background subtraction, spectra were converted to molar ellipticity (θ) per residue in deg. $cm^{-2}$ $dmol^{-1}$. The peptide concentration was determined by amino acid analysis and also by absorption spectrometry on a Perkin Elmer Lambda 17 UV/Visible spectrophotometer when the peptide contained a chromophore (tryptophan, dansyl, naphthylalanine).

CD spectra were obtained with free, unbound peptide (5 μM in 5 mM phosphate buffer, pH 7.4); with peptide-SUV complexes (20:1 EPC:Chol., Ri=50); with peptide-micelle complexes (1-myristoyl-2-hydroxy-sn-glycero-3-phosphatidyl choline, Ri=100); and with free, unbound peptide in the presence of 2,2,2-trifluoroethanol (TFE) (5 μM peptide, 90% vol TFE).

The SUVs were obtained by dispersing the lipids (10 mM, 20:1 EPC:Chol., Avanti Polar Lipids, AL) in phosphate buffer (5 mM, pH 7.4) with bubbling $N_2$ for 5 min., followed by sonication (1.5 hr.) in a bath sonicator. The homogeneity of the preparation was checked by FPLC.

The micelles were obtained by dispersing the lipid (6 mM 1-myristoyl-2-hydroxy-sn-glycero-3-phosphatidyl choline, Avanti Polar Lipids, AL) in phosphate buffer (5 mM, pH 7.4) with bubbling $N_2$ for 5 min., followed by vortexing.

To obtain the peptide-SUV complexes, SUVs were added to the peptide (5 μM in 5 mM phosphate buffer, pH 7.4) at a phospholipid-peptide molar ratio (Ri) of 100.

To obtain the peptide-micelle complexes, micelles were added to the peptide (5 μM in 5 mM phosphate buffer, pH 7.4) at a Ri of 100.

All spectra were recorded at 37° C. The stability of peptide 210 (SEQ ID NO:210) as a function of temperature (both free in buffer and in micelles) was determined by recording spectra at a series of different temperatures.

The degree of helicity of peptide 210 (SEQ ID NO:210) as a function of concentration was also determined.

7.1.2 HELICITY DETERMINATION

The degree of helicity of the peptides in the various conditions was determined from the mean residue ellipticity at 222 nm (Chen et al., 1974, Biochemistry 13:3350–3359) or by comparing the CD spectra obtained to reference spectra available on databases (16 helical reference spectra from Provencher & Glockner, 1981, Biochemistry 20:33–37; denatured protein reference spectra from Venyaminov et al., 1993, Anal. Biochem. 214:17–24) using the CONTIN curve-fitting algorithm version 2DP, CD-1 pack (August 1982) (Provencher, 1982, Comput. Phys. Commun. 27:213–227, 229–242). Acceptable fit was determined using the statistical analysis methodology provided by the CONTIN algorithm. The error of all methods was ±5% helicity.

7.1.3 RESULTS

The degree of helicity (%) of the free, unbound peptides (free), the peptide-SUV complexes (SUVs), the peptide-micelle complexes (mics) and the peptide-TFE solution (TFE) are reported in TABLE IX, section 8.3, infra.

Peptide 210 (SEQ ID NO:210) contains significant α-helical structure (63% helicity) in micelles. Moreover, the α-helical structure is completely stable over a temperature range of 5°–45° C. (data not shown). The helicity of peptide 210 (SEQ ID NO:210) also increases in the presence of TFE, which is a solvent that, due to having a signficantly lower dielectric constant ($\in=26.7$) than water ($\in=78.4$), stabilizes α-helices and intrapeptide hydrogen bonds at concentrations between 5–90% (v/v).

Referring to TABLE IX, section 8.3, infra, it can be seen that those peptides which exhibit a high degree of LCAT activation ($\geq 38\%$) generally possess significant α-helical structure in the presence of lipids ($\geq 60\%$ helical structure in the case of unblocked peptides containing 22 or more amino acids or blocked peptides containing 18 or fewer amino acids $\geq 40\%$ helical structure in the case of unblocked peptides containing 18 or fewer amino acids), whereas peptides which exhibit little or no LCAT activation possess little α-helical structure. However, in some instances, peptides which contain significant α-helical structure in the presence of lipids do not exhibit significant LCAT activation. As a consequence, the ability of the core peptides of the invention to adopt an α-helical structure in the presence of lipids is considered a critical feature of the core peptides of the invention, as the ability to form an a-helix in the presence of lipids appears to be a prerequisite for LCAT activation.

7.2 FLUORESCENCE SPECTROSCOPY

The lipid binding properties of the peptides synthesized in Section 6, supra, were tested by fluorescence measurements with labeled peptides, in the present case tryptophan (Trp or W) or naphthylalanine (Nal). The fluorescence spectra were recorded on a Fluoromax from Spex (Jobin-Yvon) equipped with a Xenon lamp of 150 W, two monochromators (excitation and emission), a photomultiplier R-928 for detection sensitive in the red up to 850 nm and a thermoelectric magnetic stirred cell holder. Quartz Suprasil cuvettes were used for measurements in the micromolar concentration range. A device of variable slits (from 0.4 to 5 nm) allows modulation of the incident and emitted intensities according to the concentration of peptide used. The reported values are in general the average of between 2 to 4 spectra. The peptide concentration is determined by absorption spectrometry on a Philips PU 8800 using the absorption band of the Trp ($\in_{280\ nm}=5{,}550$ $M^{-1}$ $cm^{-1}$ in Tris buffer) or the Nal ($\in_{224\ nm}=92{,}770$ $M^{-1}$ $cm^{-1}$ in methanol).

Fluorescence spectra of the peptides were recorded between 290 nm and 450 nm in Tris-HCl buffer (20 mM, pH=7.5), in the presence and absence of lipidic vesicles. The small unilamellar vesicles were formed after rehydration in buffer of the lyophilized phospholipids, dispersion and tip sonification under a $N_2$ stream. The lipids used were either Egg PC/Chol. (20:1) or POPC/Chol. (20:1). The spectra were recorded at a peptide concentration of 2 μM and at a temperature of 37° C. The fluorescence reference standard in the case of Trp was N-acetyltryptophanylamide (NATA).

Lipid binding studies were done through progressive lipidic vesicle addition to the peptide in solution at 2 μM (slits:5 nm in excitation and 1.5 nm in emission). Dilution effects were taken into account for the fluorescence intensity determination. The lipid concentrations were varied from 10 to 600 μM and the molar ratio of lipid to peptide (Ri) was varied from 5 to 300. The wavelength of excitation was set at 280 nm for both Trp and Nal.

7.2.1 FLUORESCENCE SPECTRAL ANALYSIS

The data were directly recorded and treated by an IBM-PC linked to the spectrofluorimeter through the DM3000F software from Spex. The spectra were corrected by substraction of the solvent contribution and by application of a coefficient given by the constructor taking into account the variation of the photomultiplier response versus the wavelength.

The fluorescence spectra of the peptides were characterized by the wavelength at their maximum of fluorescence emission and by their quantum yield compared to NATA in the case of peptides labeled with a tryptophan. The process of binding to lipids was analyzed by calculating the shift of the wavelength at the maximum of fluorescence emission, ($\lambda_{max}$), and the variation of the relative fluorescence intensity of emission versus the lipid concentration. The relative fluorescence intensity is defined as the following ratio: $(I-I_0)_{\lambda max}/I_{0\lambda max}$. I and $I_0$ are both measured at the ($\lambda_{max}$) corresponding to the initial free state of the peptide i.e., without lipids. I is the intensity at a defined lipid to peptide ratio and $I_0$ is the same parameter measured in absence of lipids. The absence of these variations is relevant to the absence of interactions of the peptides with the lipids.

7.2.2 RESULTS AND DISCUSSION

The lipid binding properties of peptide 199 (SEQ ID NO:199), which is similar in primary sequence to peptide 210 (SEQ ID NO:210) except that it contains a W (Trp) residue at position 10, are presented in TABLE VII.

TABLE VII

BINDING PROPERTIES OF PEPTIDE 199 (SEQ ID NO:199)
TO LIPIDIC VESICLES AS MEASURED BY FLUORESCENCE

| Lipid:Peptide Molar Ratio (Ri) | $I/I_o$ | $\lambda_{max}$ (nm) |
|---|---|---|
| 0 | 0 | 348 |
| 5 | 8 | 344 |
| 10 | 8 | 339 |
| 30 | 18 | 328 |
| 60 | 22 | |
| 100 | 27 | 326 |
| 200 | 41 | 325 |

In buffer at a concentration of 2 µm, the maximum of the tryptophan fluorescence emission ($\lambda_{max}$) of peptide 199 (SEQ ID NO:199) is 348 nm. This corresponds to a tryptophan which is relatively exposed to the aqueous environment when compared to NATA ($\lambda_{max}$=350 nm). Peptide 199 (SEQ ID NO:199) binds very effectively to EPC/Chol (20:1) small unilamellar vesicles as demonstrated by the burying of the tryptophan (the wavelength for the tryptophan maximum fluorescence emission shifts from 348 nm to 325 nm) and the high fluorescence intensity exaltation (See Table VII). The burying of the tryptophan residue is maximal for a lipid to peptide molar ratio of about 100.

Other peptides which exhibited a high degree of helicity in the presence of lipids ($\geq$60% for unblocked peptides of $\geq$22 amino acids, or blocked peptides of $\leq$18 amino acids; $\geq$40% for unblocked peptides of $\leq$18 amino acids) as measured by circular dichroism as disclosed in Section 7.1, supra, also demonstrated good lipid binding. Of course, among all the peptides selected by the circular dichroism screening, only the ones that could be followed by fluorescence were tested for their lipid binding properties.

7.3 NUCLEAR MAGNETIC RESONANCE (NMR)

This Example describes an NMR method for analyzing the structure of the core peptides of the invention.

7.3.1 NMR SAMPLE PREPARATION

Samples were prepared by dissolving 5 mg of peptide in 90% $H_2O$/10% $D_2O$ containing trace amounts of 2,2-Dimethyl-2-sila-5-pentane sulfonate (DSS) as an internal chemical shift reference. Some of the samples contained trifluoroethanol (TFE) (expressed as % vol). The total sample volume was 500 µl and the concentration of peptide was approximately 5 mM.

7.3.2 NMR SPECTROSCOPY $^1$H NMR spectra were acquired at 500 MHz using a Bruker DRX500 spectrometer equipped with a B-VT2000 temperature control unit. One and two-dimensional experiments were recorded using standard pulse sequences. (Two Dimensional NMR Spectroscopy, Eds. W. R. Croasmun and RMK Carlson, 1994, VCH Publishers, New York, USA). Water suppression was achieved with low power presaturation for 2 sec. Two-dimensional experiments were carried out in the phase sensitive mode using time proportional phase incrementation (TPPI) and a spectral width of 6000 Hz in both dimensions. Typically, 40 scans were co-added for 400 $t_1$ increments with 2048 data points. Data were processed using FELIX95 software (Molecular Simulations) on an INDIGO2 workstation (Silicon Graphics). Data were zero-filled to give a 2K×2K data matrix and apodized by a 45° shifted squared sine-bell function.

7.3.3 NMR ASSIGNMENT

Complete proton resonance assignments were obtained by applying the sequential assignment technique using DQFCOSY, TOCSY and NOESY spectra as described in the literature (Wuthrich, NMR of Proteins and Nucleic Acids, 1986, John Wiley & Sons, New York, USA). Secondary chemical shifts were calculated for HN and Hα protons by subtracting the tabulated random coil chemical shifts (Wishart and Sykes, 1994, Method. Enz. 239:363–392) from the corresponding experimental values.

7.3.4 RESULTS AND DISCUSSION

General Consideration. Amphipathic helical peptides tend to aggregate in aqueous solutions at the high concentrations necessary for NMR spectroscopy, making it difficult to obtain high resolution spectra. TFE is known to solubilize peptides, and in addition stabilizes helical conformations of peptides having helical propensity. The findings from NMR spectroscopy are demonstrated for peptide 210 (SEQ ID NO:210) as a representative example. The consensus 22-mer of Segrest (SEQ ID NO:75) was studied in comparison.

Secondary chemical shifts. Proton chemical shifts of amino acids depend both on the type of residue and on the local secondary structure within a peptide or protein (Szlagyi, 1995, Progress in Nuclear Magnetic Resonance Spectroscopy 27:325–443). Therefore, identification of regular secondary structure is possible by comparing experimental shifts with tabulated values for random coil conformation.

Formation of an α-helix typically results in an up-field (negative) shift for the Hα resonance. Observation of an upfield Hα shift for several sequential residues is generally taken as evidence of a helical structure. The Hα secondary shifts for peptide 210 (SEQ ID NO:210) in 25% TFE at 295 K show a significant negative shift for residues 4 through 15 (FIG. 7A), demonstrating a highly helical conformation. Small differences are observed in the Hα chemical shifts of the consensus 22-mer (SEQ ID NO:75) compared to peptide 210 (SEQ ID NO:210).

The chemical shifts of amide hydrogens of amino acid residues residing in regions of α-helix are also shifted upfield with respect to the chemical shifts observed for random coil. In addition, a periodicity of the HN shifts can be observed, and it reflects the period of the helical turns. The amplitude of the shift variation along the sequence is related to the amphipathicity of a helical peptide. A higher hydrophobic moment leads to a more pronounced oscillation (Zhou et al., 1992, J. Am. Chem. Soc. 114:4320–4326). The HN secondary shifts for peptide 210 (SEQ ID NO:210) in 25% TFE at 295 K show an oscillatory behavior in agreement with the amphipathic nature of the helix (FIG. 7B).

The amino acid replacements lead to a more pronounced periodicity along the entire sequence (FIG. 7B). The pattern clearly reflects the stronger amphipathic nature of peptide 210 (SEQ ID NO:210) as compared to Segrest's consensus 22-mer (SEQ ID NO:75). The existence of 4–5 helical turns can be discerned.

The secondary shift of an amide proton is influenced by the length of the hydrogen bond to the carbonyl oxygen one turn away from the helix. Therefore, the periodicity of observed chemical shift values reflects different hydrogen bond lengths. This difference is associated with an overall curved helical shape of the helix backbone. The hydrophobic residues are situated on the concave side. The secondary shifts of peptide 210 (SEQ ID NO:210) indicate a curved α-helical conformation.

8. EXAMPLE

LCAT Activation Assay

The peptides synthesized as described in Section 6, supra, were analyzed in vitro for their ability to activate LCAT. In the LCAT assay, substrate vesicles (small unilamellar vesicles or "SUVs") composed of egg phophatidylcholine (EPC) or 1-Palmitoyl-2-oleyl-phosphatidylcholine (POPC) and radiolabelled cholesterol are preincubated with equivalent masses either of peptide or ApoA-I (isolated from human plasma). The reaction is initiated by addition of LCAT (purified from human plasma). Native ApoA-I, which was used as positive control, represents 100% activation activity. "Specific activity" (i.e., units of activity (LCAT activation)/unit of mass) of the peptides can be calculated as the concentration of peptide that achieves maximum LCAT activation. For example, a series of concentrations of the peptide (e.g., a limiting dilution) can be assayed to determine the "specific activity" for the peptide—the concentration which achieves maximal LCAT activation (i.e., percentage conversion of cholesterol to cholesterol ester) at a specific timepoint in the assay (e.g., 1 hr.). When plotting percentage conversion of cholesterol at, e.c., 1 hr., against the concentration of peptide used, the "specific activity" can be identified as the concentration of peptide that achieves a plateau on the plotted curve.

8.1 PREPARATION OF SUBSTRATE VESICLES

The vesicles used in the LCAT assay are SUVs composed of egg phosphatidylcholine (EPC) or 1-palmitoyl-2-oleyl-phosphatidylcholine (POPC) and cholesterol with a molar ratio of 20:1. To prepare a vesicle stock solution sufficient for 40 assays, 7.7 mg EPC (or 7.6 mg POPC; 10 μmol), 78 μg (0.2 μmol) 4-$^{14}$C-cholesterol, 116 μg cholesterol (0.3 μmol) are dissolved in 5 ml xylene and lyophilized. Thereafter 4 ml of assay buffer is added to the dry powder and sonicated under nitrogen atmosphere at 4° C. Sonication conditions: Branson 250 sonicator, 10 mm tip, 6×5 minutes; Assay buffer: 10 mM Tris, 0.14 M NaCl, 1 mM EDTA, pH 7.4). The sonicated mixture is centrifuged 6 times for 5 minutes each time at 14,000 rpm (16,000×g) to remove titanium particles. The resulting clear solution is used for the enzyme assay.

8.2 PURIFICATION OF LCAT

For the LCAT purification, dextran sulfate/Mg$^{2+}$ treatment of human plasma is used to obtain lipoprotein deficient serum (LPDS). which is sequentially chromatographed on Phenylsepharose. A ffigelblue, ConcanavalinA sepharose and auti-ApoA-I affinity chromatography, as summarized for a representative purification TABLE VIII, below:

TABLE VIII

| Fraction | Total Volume (ml) | Total Protein (mg) | Total Activity (nmol CE/mg*hr) | Yield (%) | Purification (fold) |
|---|---|---|---|---|---|
| Plasma | 550 | 44550 | 63706 | | |
| LPDS | 500 | 31000 | 62620 | 98 | 1.4 |

TABLE VIII-continued

LCAT PURIFICATION

| Fraction | Total Volume (ml) | Total Protein (mg) | Total Activity (nmol CE/mg*hr) | Yield (%) | Purification (fold) |
|---|---|---|---|---|---|
| Phenyl sepharose | 210 | 363 | 51909 | 82 | 100 |
| Affigel blue | 95 | 153 | 25092 | 39 | 115 |
| ConA sepharose | 43 | 36 | 11245 | 18 | 220 |
| Anti-A-I Affinity | 120 | 3.5 | 5500 | 9 | 1109 |

8.2.1 PREPARATION OF LPDS

To prepare LPDS, 500 ml plasma is added to 50 ml dextran sulfate (MW=500000) solution. Stir 20 minutes. Centrifuge for 30 minutes at 3000 rpm (16,000×g) at 4° C. Use supernatant (LPDS) for further purification (ca. 500 ml).

8.2.2 PHENYLSEPHAROSE CHROMATOGRAPHY

The following materials and conditions were used for the phenylsepharose chromatography.

| | |
|---|---|
| solid phase: | Phenylsepharose fast flow, high subst. grade, Pharmacia |
| column: | XK26/40, gel bed height: 33 cm, V = ca. 175 ml |
| flow rates: | 200 ml/hr (sample) |
| wash: | 200 ml/hr (buffer) |
| elution: | 80 ml/hr (distilled water) |
| buffer: | 10 mM Tris, 140 mM NaCl, 1 mM EDTA pH 7.4, 0.01% sodium azide. |

Equilibrate the column in Tris-buffer, add 29 g NaCl to 500 ml LPDS and apply to the column. Wash with several volumes of Tris buffer until the absorption at 280 nm wavelength is approximately at the baseline, then start the elution with distilled water. The fractions containing protein are pooled (pool size: 180 ml) and used for Affigelblue chromatography.

8.2.3 AFFIGELBLUE CHROMATOGRAPHY

The Phenylsepharose pool is dialyzed overnight at 4° C. against 20 mM Tris-HCl, pH 7.4, 0.01% sodium azide. The pool volume is reduced by ultrafiltration (Amicon YM30) to 50–60 ml and loaded on an Affigelblue column.

| | |
|---|---|
| solid phase: | Affigelblue, Biorad, 153–7301 column, XK26/20, gel bed height: ca. 13 cm; column volume: approx. 70 ml. |
| flow rates: | loading: 15 ml/h<br>wash: 50 ml/h |

Equilibrate column in Tris-buffer. Apply Phenylsepharose pool to column. Start in parallel to collect fractions. Wash with Tris-buffer. The pooled fractions (170 ml) were used for ConA chromatography.

8.2.4 ConA CHROMATOGRAPHY

The Affigelblue pool was reduced via Amicon (YM30) to 30–40 ml and dialyzed against ConA starting buffer (1 mM Tris HCl pH7.4; 1 mM MgCl$_2$, 1 mM MnCl$_2$, 1 mM CaCl$_2$, 0.01% Na-azide) overnight at 4° C.

| | |
|---|---|
| solid phase: | ConA sepharose (Pharmacia) |
| column: | XK26/20, gel bed height: 14 cm (75 ml) |
| flow rates: | loading 40 ml/h |
| | washing (with starting buffer): 90 ml/h |
| | elution: 50 ml/h, 0.2 M Methyl-α-D-mannoside in 1 mM Tris, pH 7.4. |

The protein fractions of the mannoside elutions were collected (110 ml), and the volume was reduced by ultrafiltration (YM30) to 44 ml. The ConA pool was divided in 2 ml aliquots, which are stored at −20° C.

8.2.5 ANTI-ApoA-I AFFINITY CHROMATOGRAPHY

Anti-ApoA-I affinity chromatography was performed on Affigel-Hz material (Biorad), to which the anti-ApoA-I abs have been coupled covalently.

| | |
|---|---|
| column: | XK16/20, V = 16 ml. The column was equilibrated with PBS pH 7.4. Two ml of the ConA pool was dialyzed for 2 hours against PBS before loading onto the column. |
| flow rates: | loading: 15 ml/hour washing (PBS) 40 ml/hour. |

The pooled protein fractions (V=14 ml) are used for LCAT assays.

The column is regenerated with 0.1 M. Citrate buffer (pH 4.5) to elute bound A-I (100 ml), and immediately after this procedure reequilibrated with PBS.

8.3 RESULTS

The results of the LCAT activation assay are presented in TABLE IX, infra.

TABLE IX

LCAT ACTIVATION EXHIBITED BY EXEMPLARY CORE PEPTIDES

| PEPTIDE | | AMINO ACID SEQUENCE | ACTIVITY (%) LCAT | He (%) free | He (%) mics | He (%) SUVs | He (%) TFE |
|---|---|---|---|---|---|---|---|
| 1 | (SEQ ID NO:1) | PVLDLFRELLNELLEZLKQKLK | 120% | 77 | 85 | 81 | 69 |
| 2 | (SEQ ID NO:2) | GVLDLFRELLNELLEALKQKLKK | 105% | | | | |
| 3 | (SEQ ID NO:3) | PVLDLFRELLNELLEWLKQKLK | 98% | 70 | 95 | 80 | 95 |
| 4 | (SEQ ID NO:4) | PVLDLFRELLNELLEALKQKLK | 93% | 80 | 95 | 97 | 94 |
| 5 | (SEQ ID NO:5) | PVLDLFRELLNELLEALKQKLKK | 90% | | | | |
| 6 | (SEQ ID NO:6) | PVLDLFRELLNEXLEALKQKLK | 80% | 57 | 93 | 70 | 99 |
| 7 | (SEQ ID NO:7) | PVLDLFKELLNELLEALKQKLK | 83% | 77 | 89 | 85 | 73 |
| 8 | (SEQ ID NO:8) | PVLDLFRELLNEGLEALKQKLK | 83% | 20 | 90 | 61 | 93 |
| 9 | (SEQ ID NO:9) | PVLDLFRELGNELLEALKQKLK | 83% | | | | |
| 10 | (SEQ ID NO:10) | PVLDLFRELLNELLEAZKQKLK | 79% | 60 | 87 | 70 | 71 |
| 11 | (SEQ ID NO:11) | PVLDLFKELLQELLEALKQKLK | 72% | | | | |
| 12 | (SEQ ID NO:12) | PVLDLFRELLNELLEAGKQKLK | 70% | | | | |
| 13 | (SEQ ID NO:13) | GVLDLFRELLNEGLEALKQKLK | 67% | | | | |
| 14 | (SEQ ID NO:14) | PVLDLFRELLNELLEALOQOLO | 61% | 70 | 96 | 80 | |
| 15 | (SEQ ID NO:15) | PVLDLFRELWNELLEALKQKLK | 60% | 55 | 60 | 64 | 68 |
| 16 | (SEQ ID NO:16) | PVLDLLRELLNELLEALKQKLK | 59% | | | | |
| 17 | (SEQ ID NO:17) | PVLELFKELLQELLEALKQKLK | 59% | | | | |
| 18 | (SEQ ID NO:18) | GVLDLFRELLNELLEALKQKLK | 58% | | | | |
| 19 | (SEQ ID NO:19) | pVLDLFRELLNEGLEALKQKLK | 58% | | | | |
| 20 | (SEQ ID NO:20) | PVLDLFREGLNELLEALKQKLK | 57% | | | | |
| 21 | (SEQ ID NO:21) | pVLDLFRELLNELLEALKQKLK | 57% | | | | |
| 22 | (SEQ ID NO:22) | PVLDLFRELLNELLEGLKQKLK | 54% | | | | |
| 23 | (SEQ ID NO:23) | PLLELFKELLQELLEALKQKLK | 54% | | | | |
| 24 | (SEQ ID NO:24) | PVLDLFRELLNELLEALQKKLK | 53% | | | | |
| 25 | (SEQ ID NO:25) | PVLDFFRELLNEXLEALKQKLK | 51% | 46 | 82 | | 93 |
| 26 | (SEQ ID NO:26) | PVLDLFRELLNELLELLKQKLK | 47% | | | | |
| 27 | (SEQ ID NO:27) | PVLDLFRELLNELZEALKQKLK | 44% | 72 | 92 | 82 | 81 |
| 28 | (SEQ ID NO:28) | PVLDLFRELLNELWEALKQKLK | 40% | 82 | 98 | 90 | 81 |
| 29 | (SEQ ID NO:29) | AVLDLFRELLNELLEALKQKLK | 39% | | | | |
| 30 | (SEQ ID NO:30) | PVLDLFRELLNELLEALKQKLK | 38% | 85 | 90 | 98 | 90 |
| 31 | (SEQ ID NO:31) | PVLDLFLELLNEXLEALKQKLK | 34% | 49 | 98 | | 90 |
| 32 | (SEQ ID NO:32) | XVLDLFRELLNELLEALKQKLK | 33% | | | | |
| 33 | (SEQ ID NO:33) | PVLDLFREKLNELLEALKQKLK | 33% | | | | |
| 34 | (SEQ ID NO:34) | PVLDZFRELLNELLEALKQKLK | 32% | 58 | 67 | 68 | 62 |
| 35 | (SEQ ID NO:35) | PVLDWFRELLNELLEALKQKLK | 31% | 49(sp) | 59 | 61 | |
| 36 | (SEQ ID NO:36) | PLLELLKELLQELLEALKQKLK | 31% | 95 | 100 | | 95 |
| 37 | (SEQ ID NO:37) | PVLDLFREWLNELLEALKQKLK | 29% | 65 | 75 | 76 | 73 |
| 38 | (SEQ ID NO:38) | PVLDLFRELLNEXLEAWKQKLK | 29% | 25 | 49 | 21 | 49 |
| 39 | (SEQ ID NO:39) | PVLDLFRELLEELLKALKKKLK | 25% | 66 | 69 | 68 | 72 |
| 40 | (SEQ ID NO:40) | PVLDLFNELLRELLEALQKKLK | 25% | 66 | 84 | 79 | 77 |
| 41 | (SEQ ID NO:41) | PVLDLWRELLNEXLEALKQKLK | 25% | 53 | 73 | 85 | 69 |
| 42 | (SEQ ID NO:42) | PVLDEFREKLNEXWEALKQKLK | 25% | 15 | 74 | 27 | 76 |
| 43 | (SEQ ID NO:43) | PVLDEFREKLWEXLEALKQKLK | 25% | | | | |
| 44 | (SEQ ID NO:44) | pvldefreklneXlealkqklk | 25% | 20 | 86 | | |

TABLE IX-continued

LCAT ACTIVATION EXHIBITED BY EXEMPLARY CORE PEPTIDES

| PEPTIDE | | AMINO ACID SEQUENCE | ACTIVITY (%) LCAT | He (%) free | He (%) mics | He (%) SUVs | He (%) TFE |
|---|---|---|---|---|---|---|---|
| 45 | (SEQ ID NO:45) | PVLDEFREKLNEXLEALKQKLK | 24% | 24 | 84 | 25 | 86 |
| 46 | (SEQ ID NO:46) | PVLDLFREKLNEXLEALKQKLK | 23% | 30 | 86 | 58 | 85 |
| 47 | (SEQ ID NO:47) | ~VLDLFRELLNEGLEALKQKLK | 23% | | | | |
| 48 | (SEQ ID NO:48) | pvLDLFRELLNELLEALKQKLK | 22% | | | | |
| 49 | (SEQ ID NO:49) | PVLDLFRNLLEKLLEALEQKLK | 22% | 57 | 65 | 52 | 57 |
| 50 | (SEQ ID NO:50) | PVLDLFRELLWEXLEALKQKLK | 21% | 68 | 84 | 89 | 76 |
| 51 | (SEQ ID NO:51) | PVLDLFWELLNEXLEALKQKLK | 20% | 63 | 82 | 81 | 73 |
| 52 | (SEQ ID NO:52) | PVWDEFREKLNEXLEALKQKLK | 20% | sp | sp | sp | |
| 53 | (SEQ ID NO:53) | VVLDLFRELLNELLEALKQKLK | 19% | | | | |
| 54 | (SEQ ID NO:54) | PVLDLFRELLNEWLEALKQKLK | 19% | 76 | 71 | 84 | 78 |
| 55 | (SEQ ID NO:55) | P~~~LFRELLNELLEALKQKLK | 19% | 38 | 72 | 78 | 75 |
| 56 | (SEQ ID NO:56) | PVLDLFRELLNELLEALKQKKK | 18% | | | | |
| 57 | (SEQ ID NO:57) | PVLDLFRNLLEELLKALEQKLK | 18% | | | | |
| 58 | (SEQ ID NO:58) | PVLDEFREKLNEXLEALKQKL~ | 18% | | | | |
| 59 | (SEQ ID NO:59) | LVLDLFRELLNELLEALKQKLK | 17% | | | | |
| 60 | (SEQ ID NO:60) | PVLDLFRELLNELLEALKQ~~~ | 16% | 39 | 83 | 66 | 84 |
| 61 | (SEQ ID NO:61) | PVLDFRWKLNEXLEALKQKLK | 16% | | | | |
| 62 | (SEQ ID NO:62) | PVLDEWREKLNEXLEALKQKLK | 16% | 15 | 85 | 43 | |
| 63 | (SEQ ID NO:63) | PVLDFFREKLNEXLEALKQKLK | 16% | | | | |
| 64 | (SEQ ID NO:64) | PWLDEFREKLNEXLEALKQKLK | 15% | | | | |
| 65 | (SEQ ID NO:65) | ~VLDEFREKLNEXLEALKQKLK | 15% | | | | |
| 66 | (SEQ ID NO:66) | PVLDLFRNLLEELLEALQKKLK | 15% | 64 | 82 | 66 | 70 |
| 67 | (SEQ ID NO:67) | ~VLDLFRELLNELLEALKQKLK | 14% | 81 | 90 | 84 | 94 |
| 68 | (SEQ ID NO:68) | PVLDEFRELLKEXLEALKQKLK | 14% | | | | |
| 69 | (SEQ ID NO:69) | PVLDEFRKKLNEXLEALKQKLK | 13% | | | | |
| 70 | (SEQ ID NO:70) | PVLDEFRELLYEXLEALKQKLK | 12% | 27 | 78 | 33 | 66 |
| 71 | (SEQ ID NO:71) | PVLDEFREKLNELXEALKQKLK | 11% | | | | |
| 72 | (SEQ ID NO:72) | PVLDLFRELLNEXWALKQKLK | 11% | sp | sp | sp | |
| 73 | (SEQ ID NO:73) | PVLDEFWEKLNEXLEALKQKLK | 10% | | | | |
| 74 | (SEQ ID NO:74) | PVLDKFREKLNEXLEALKQKLK | 10% | | | | |
| 75[1/] | (SEQ ID NO:75) | PVLDEFREKLNEELEALKQKLK | 10% | 18 | 28 | 23 | 55 |
| 76 | (SEQ ID NO:76) | PVLDEFRELLFEXLEALKQKLK | 9% | 41 | 88 | | 66 |
| 77 | (SEQ ID NO:77) | PVLDEFREKLNKXLEALKQKLK | 9% | | | | |
| 78 | (SEQ ID NO:78) | PVLDEFRDKLNEXLEALKQKLK | 9% | | | | |
| 79 | (SEQ ID NO:79) | PVLDEFRELLNELLEALKQKLK | 9% | | | | |
| 80 | (SEQ ID NO:80) | PVLDLFERLLNELLEALQKKLK | 9% | | | | |
| 81 | (SEQ ID NO:81) | PVLDEFREKLNWXLEALKQKLK | | | | | |
| 82 | (SEQ ID NO:82) | ~~LDEFREKLNEXLEALKQKLK | 8% | | | | |
| 83 | (SEQ ID NO:83) | PVLDEFREKLNEXLEALWQKLK | | | | | |
| 84 | (SEQ ID NO:84) | PVLDEFREKLNELLEALKQKLK | 7% | | | | |
| 85 | (SEQ ID NO:85) | P~LDLFRELLNELLEALKQKLK | 7% | 58 | 61 | 64 | 69 |
| 86 | (SEQ ID NO:86) | PVLELFERLLDELLNALQKKLK | 7% | | | | |
| 87 | (SEQ ID NO:87) | pllellkellqellealkqklk | 7% | 100 | 100 | | 100 |
| 88 | (SEQ ID NO:88) | PVLDKFRELLNEXLEALKQKLK | 7% | | | | |
| 89 | (SEQ ID NO:89) | PVLDEFREKLNWXLEALKQKLK | 6% | | | | |
| 90 | (SEQ ID NO:90) | ~~~DEFREKLNEXLEALKQKLK | 6% | | | | |
| 91 | (SEQ ID NO:91) | PVLDEFRELLNEXLEALKQKLK | 6% | 43 | 100 | | 100 |
| 92 | (SEQ ID NO:92) | PVLDEFRELYNEXLEALKQKLK | 5% | | | | |
| 93 | (SEQ ID NO:93) | PVLDEFREKLNEXLKALKQKLK | 5% | | | | |
| 94[2/] | (SEQ ID NO:94) | PVLDEFREKLNEALEALKQKLK | 5% | 18 | 70 | 27 | 63 |
| 95 | (SEQ ID NO:95) | PVLDLFRELLNLXLEALKQKLK | 5% | | sp | sp | |
| 96 | (SEQ ID NO:96) | pvldlfrellneXlealkqklk | 5% | 52 | 85 | 63 | 81 |
| 97 | (SEQ ID NO:97) | PVLDLFRELLNELLE~~~~~~ | 4% | | | | |
| 98 | (SEQ ID NO:98) | PVLDLFRELLNELLEALKQKLK | 2% | | | | |
| 99 | (SEQ ID NO:99) | KLKQKLAELLENLLERFLDLVP | 2% | 72 | 88 | 80 | 80 |
| 100 | (SEQ ID NO:100) | pvldlfrellnellealkqklk | 2% | 83 | 92 | | 98 |
| 101 | (SEQ ID NO:101) | PVLDLFRELLNWXLEALKQKLK | 2% | | sp | sp | |
| 102 | (SEQ ID NO:102) | PVLDLFRELLNLXLEALKEKLK | 2% | sp | | | |
| 103 | (SEQ ID NO:103) | PVLDEFRELLNEELEALKQKLK | 1% | | | | |
| 104 | (SEQ ID NO:104) | P~~~~~~LLNELLEALKQKLK | 1% | 21 | 49 | 29 | 55 |
| 105 | (SEQ ID NO:105) | PAADAFREAANEAAEAAKQKAK | 1% | 29 | 28 | 32 | 65 |
| 106 | (SEQ ID NO:106) | PVLDLFREKLNEELEALKQKLK | 0% | | | | |
| 107 | (SEQ ID NO:107) | .klkgklaellenllerfldlvp | 0% | sp | sp | | 77 |
| 108 | (SEQ ID NO:108) | PVLDLFRWLLNEXLEALKQKLK | 0% | 28 | 55 | 54 | |
| 109[3/] | (SEQ ID NO:109) | PVLDEFREKLNERLEALKQKLK | 0% | 19 | 45 | 23 | 58 |
| 110 | (SEQ ID NO:110) | PVLDEFREKLNEXXEALKQKLK | 0% | | | | |
| 111 | (SEQ ID NO:111) | PVLDEFREKLWEXWEALKQKLK | 0% | | | | |
| 112 | (SEQ ID NO:112) | PVLDEFREKLNEXSEALKQKLK | 0% | | | | |
| 113 | (SEQ ID NO:113) | PVLDEFREKLNEPLEALKQKLK | 0% | 6 | 22 | | |
| 114 | (SEQ ID NO:114) | PVLDEFREKLNEXMEALKQKLK | 0% | | | | |
| 115 | (SEQ ID NO:115) | PKLDEFREKLNEXLEALKQKLK | 0% | | | | |
| 116 | (SEQ ID NO:116) | PHLDEFREKLNEXLEALKQKLK | 0% | | | | |

TABLE IX-continued

LCAT ACTIVATION EXHIBITED BY EXEMPLARY CORE PEPTIDES

| PEPTIDE | AMINO ACID SEQUENCE | ACTIVITY LCAT (%) | He (%) free | He (%) mics | He (%) SUVs | He (%) TFE |
|---|---|---|---|---|---|---|
| 117 | (SEQ ID NO:117)PELDEFREKLNEXLEALKQKLK | 0% | | | | |
| 118 | (SEQ ID NO:118)PVLDEFREKLNEXLEALEQKLK | 0% | | | | |
| 119 | (SEQ ID NO:119)PVLDEFREKLNEELEAXKQKLK | 0% | | | | |
| 120 | (SEQ ID NO:120)PVLDEFREKLNEELEXLKQKLK | 0% | | | | |
| 121 | (SEQ ID NO:121)PVLDEFREKLNEELEALWQKLK | 0% | | | | |
| 122 | (SEQ ID NO:122)PVLDEFREKLNEELEWLKQKLK | 0% | | | | |
| 123 | (SEQ ID NO:123)QVLDLFRELLNELLEALKQKLK | | | | | |
| 124 | (SEQ ID NO:124)PVLDLFOELLNELLEALOQOLO | | | | | |
| 125 | (SEQ ID NO:125)NVLDLFRELLNELLEALKQKLK | | | | | |
| 126 | (SEQ ID NO:126)PVLDLFRELLNELGEALKQKLK | | | | | |
| 127 | (SEQ ID NO:127)PVLDLFRELLNELLELLKQKLK | 47% | | | | |
| 128 | (SEQ ID NO:128)PVLDLFRELLNELLEFLKQKLK | | | | | |
| 129 | (SEQ ID NO:129)PVLELFNDLLRELLEALQKKLK | | | | | |
| 130 | (SEQ ID NO:130)PVLELFNDLLRELLEALKQKLK | | | | | |
| 131 | (SEQ ID NO:131)PVLELFKELLNELLDALRQKLK | | | | | |
| 132 | (SEQ ID NO:132)PVLDLFRELLNLLEALQKKLK | | | | | |
| 133 | (SEQ ID NO:133)PVLELFERLLEDLLQALNKKLK | | | | | |
| 134 | (SEQ ID NQ:134)PVLELFERLLEDLLKALNQKLK | | | | | |
| 135 | (SEQ ID NO:135)DVLDLFRELLNELLEALKQKLK | | | | | |
| 136 | (SEQ ID NO:136)PALELFKDLLQELLEALKQKLK | | | | | |
| 137 | (SEQ ID NO:137)PVLDLFRELLNEGLEAZKQKLK | | | | | |
| 138 | (SEQ ID NO:138)PVLDLFRELLNEGLEWLKQKLK | | | | | |
| 139 | (SEQ ID NO:139)PVLDLFRELWNEGLEALKQKLK | | | | | |
| 140 | (SEQ ID NO:140)PVLDLFRELLNEGLEALOQOLO | | | | | |
| 141 | (SEQ ID NO:141)pVLDFFRELLNEGLEALKQKLK | | | | | |
| 142 | (SEQ ID NO:142)pVLELFRELLNEGLEALKQKLK | | | | | |
| 143 | (SEQ ID NO:143)pVLDLFRELLNEGLEALKQKLK* | | | | | |
| 144 | (SEQ ID NO:144)pVLELFENLLERLLDALQKKLK | 111% | 89 | 88 | | 95 |
| 145 | (SEQ ID NO:145)GVLELFENLLERLLDALQKKLK | 100% | 55 | 51 | | 58 |
| 146 | (SEQ ID NO:146)PVLELFENLLERLLDALQKKLK | 86% | 97 | 100 | 100 | 95 |
| 147 | (SEQ ID NO:147)PVLELFENLLERLFDALQKKLK | 76% | | | | |
| 148 | (SEQ ID NO:148)PVLELFENLLERLGDALQKKLK | 75% | 10 | 76 | 23 | 80 |
| 149 | (SEQ ID NO:149)PVLELFENLWERLLDALQKKLK | 63% | 28 | 54 | | 47 |
| 150 | (SEQ ID NO:150)PLLELFENLLERLLDALQKKLK | 57% | | | | |
| 151 | (SEQ ID NO:151)PVLELFENLGERLLDALQKKLK | 55% | | | | |
| 152 | (SEQ ID NO:152)PVFELFENLLERLLDALQKKLK | 50% | | | | |
| 153 | (SEQ ID NO:153)AVLELFENLLERLLDALQKKLK | 49% | | | | |
| 154 | (SEQ ID NO:154)PVLELFENLLERGLDALQKKLK | 39% | 13 | 76 | 25 | 80 |
| 155 | (SEQ ID NO:155)PVLELFLNLWERLLDALQKKLK | 38% | | | | |
| 156 | (SEQ ID NO:156)PVLELFLNLLERLLDALQKKLK | 35% | | | | |
| 157 | (SEQ ID NO:157)PVLEFFENLLERLLDALQKKLK | 30% | | | | |
| 158 | (SEQ ID NO:158)PVLELFLNLLERLLDWLQKKLK | 30% | | | | |
| 159 | (SEQ ID NO:159)PVLDLFENLLERLLDALQKKLK | 28% | | | | |
| 160 | (SEQ ID NO:160)PVLELFENLLERLLDWLQKKLK | 28% | 65 | 73 | 75 | 61 |
| 161 | (SEQ ID NO:161)PVLELFENLLERLLEALQKKLK | 27% | | | | |
| 162 | (SEQ ID NO:162)PVLELFENWLERLLDALQKKLK | 27% | 68 | 83 | 81 | |
| 163 | (SEQ ID NO:163)PVLELFENLLERLWDALQKKLK | 26% | 27 | 53 | | 55 |
| 164 | (SEQ ID NO:164)PVLELFENLLERLLDAWQKKLK | 24% | 37 | 66 | 51 | 61 |
| 165 | (SEQ ID NO:165)PVLELFENLLERLLDLLQKKLK | 23% | | | | |
| 166 | (SEQ ID NO:166)PVLELFLNLLEKLLDALQKKLK | 22% | | | | |
| 167 | (SEQ ID NO:167)PVLELFENGLERLLDALQKKLK | 18% | | | | |
| 168 | (SEQ ID NO:168)PVLELFEQLLEKLLDALQKKLK | 17% | | | | |
| 169 | (SEQ ID NO:169)PVLELFENLLEKLLDALQKKLK | 17% | | | | |
| 170 | (SEQ ID NO:170)PVLELFENLLEOLLDALQOOLO | 17% | | | | |
| 171 | (SEQ ID NO:171)PVLELFENLLEKLLDLLQKKLK | 16% | | | | |
| 172 | (SEQ ID NO:172)PVLELFLNLLERLGDALQKKLK | 16% | | | | |
| 173 | (SEQ ID NO:173)PVLDLFDNLLDRLLDLLNKKLK | 15% | | | | |
| 174 | (SEQ ID NO:174)pvlelfenllerlldalqkklk | 13% | | | | |
| 175 | (SEQ ID NO:175)PVLELFENLLERLLELLNKKLK | 13% | | | | |
| 176 | (SEQ ID NO:176)PVLELWENLLERLLDALQKKLK | 11% | | | | |
| 177 | (SEQ ID NO:177)GVLELFLNLLERLLDALQKKLK | 10% | | | | |
| 178 | (SEQ ID NO:178)PVLELFDNLLEKLLEALQKKLR | 9% | | | | |
| 179 | (SEQ ID NO:179)PVLELFDNLLERLLDALQKKLK | 8% | | | | |
| 180 | (SEQ ID NO:180)PVLELFDNLLDKLLDALQKKLR | 8% | | | | |
| 181 | (SEQ ID NO:181)PVLELFENLLERWLDALQKKLK | 8% | | | | |
| 182 | (SEQ ID NO:182)PVLELFENLLEKLLEALQKKLK | 7% | | | | |
| 183 | (SEQ ID NO:183)PLLELFENLLEKLLDALQKKLK | 6% | | | | |
| 184 | (SEQ ID NO:184)PVLELFLNLLERLLDAWQKKLK | 4% | | | | |
| 185 | (SEQ ID NO:185)PVLELFENLLERLLDALQOOLO | 3% | | | | |
| 186 | (SEQ ID NO:186)PVLELFEQLLERLLDALQKKLK | | | | | |
| 187 | (SEQ ID NO:187)PVLELFENLLRLLDALNKKLK | | | | | |
| 188 | (SEQ ID NO:188)PVLELFENLLDRLLDALQKKLK | | | | | |

TABLE IX-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 189 | (SEQ ID NO:189)DVLELFENLLERLLDALQKKLK | | | | | |
| 190 | (SEQ ID NO:190)PVLEFWDNLLDKLLDALQKKLR | | | | | |
| 191 | (SEQ ID NO:191)PVLDLLRELLEELKQKLK* | 100% | | | | |
| 192 | (SEQ ID NO:192)PVLDLFKELLEELKQKLK* | 100% | 36 | | | 56 |
| 193 | (SEQ ID NO:193)PVLDLFRELLEELKQKLK* | 96% | 34 | 88 | 87 | 87 |
| 194 | (SEQ ID NO:194)PVLELFRELLEELKQKLK* | 88% | 38 | 93 | | 93 |
| 195 | (SEQ ID NO:195)PVLELFKELLEELKQKLK* | 87% | | | | |
| 196 | (SEQ ID NO:196)PVLDLFRELLEELKNKLK* | 81% | | | | |
| 197 | (SEQ ID NO:197)PLLDLFRELLEELKQKLK* | 81% | 43 | 70 | | 69 |
| 198 | (SEQ ID NO:198)GVLDLFRELLEELKQKLK* | 80% | | | | |
| 199 | (SEQ ID NO:199)PVLDLFRELWEELKQKLK* | 76% | 35 | 77 | 80 | 79 |
| 200 | (SEQ ID NO:200)NVLDLFRELLEELKQKLK* | 75% | | | | |
| 201 | (SEQ ID NO:201)PLLDLFKELLEELKQKLK* | 74% | | | | |
| 202 | (SEQ ID NO:202)PALELFKDLLEELRQKLR* | 70% | | | | |
| 203 | (SEQ ID NO:203)AVLDLFRELLEELKQKLK* | 66% | | | | |
| 204 | (SEQ ID NO:204)PVLDFFRELLEELKQKLK* | 63% | | | | |
| 205 | (SEQ ID NO:205)PVLDLFREWLEELKQKLK* | 60% | | | | |
| 206 | (SEQ ID NO:206)PLLELLKELLEELKQKLK* | 57% | | | | |
| 207 | (SEQ ID NO:207)PVLELLKELLEELKQKLK* | 50% | | | | |
| 208 | (SEQ ID NO:208)PALELFKDLLEELRQRLK* | 48% | | | | |
| 209 | (SEQ ID NO:209)PVLDLFRELLNELLQKLK | 47% | 54 | 71 | 67 | 62 |
| 210 | (SEQ ID NO:210)PVLDLFRELLEELKQKLK | 46% | 20 | 63 | 37 | 53 |
| 211 | (SEQ ID NO:211)PVLDLFRELLEELQQLQ* | 45% | | | | |
| 212 | (SEQ ID NO:212)PVLDLFOELLEELQQLK* | 43% | | | | |
| 213 | (SEQ ID NO:213)PALELFKDLLEEFRQRLK* | 42% | | | | |
| 214 | (SEQ ID NO:214)PVLDLFRELLEELKQKLK* | 39% | | | | |
| 215 | (SEQ ID NO:215)PVLDLFRELLEEWKQKLK* | 38% | 28 | 63 | 53 | 68 |
| 216 | (SEQ ID NO:216)PVLELFKELLEELKQKLK | 35% | | | | |
| 217 | (SEQ ID NO:217)PVLDLFRELLELLKQKLK | 30% | 52 | 78 | 76 | 70 |
| 218 | (SEQ ID NO:218)PVLDLFRELLNELLQKLK* | 29% | | | | |
| 219 | (SEQ ID NO:219)PVLDLFRELLNELWQKLK | 24% | | | | |
| 220 | (SEQ ID NO:220)PVLDLFRELLEELQKKLK | 22% | 27 | 64 | 54 | 64 |
| 221 | (SEQ ID NO:221)DVLDLFRELLEELKQKLK* | 12% | | | | |
| 222 | (SEQ ID NO:222)PVLDAFRELLEALLQLKK | 8% | | | | |
| 223 | (SEQ ID NO:223)PVLDAFRELLEALAQLKK | 8% | 21 | 56 | 23 | 51 |
| 224 | (SEQ ID NO:224)PVLDLFREGWEELKQKLK | 8% | | | | |
| 225 | (SEQ ID NO:225)PVLDAFRELAEALAQLKK | 1% | | | | |
| 226 | (SEQ ID NO:226)PVLDAFRELGEALLQLKK | 1% | | | | |
| 227 | (SEQ ID NO:227)PVLDLFRELGEELKQKLK* | | | | | |
| 228 | (SEQ ID NO:228)PVLDLFREGLEELKQKLK* | 0% | | | | |
| 229 | (SEQ ID NO:229)PVLDLFRELLEEGKQKLK* | 0% | | | | |
| 230 | (SEQ ID NO:230)PVLELFERLLEDLQKKLK | | | | | |
| 231 | (SEQ ID NO:231)PVLDLFRELLEKLEQKLK | | | | | |
| 232 | (SEQ ID NO:232)PLLELFKELLEELKQKLK* | | | | | |
| 237[4/] | (SEQ ID NO:237)LDDLLQKWAEAFNQLLKK | 11% | 30 | 66 | 45 | — |
| 238[5/] | (SEQ ID NO:238)EWLKAFYEKVLEKLKELF* | 19% | 49 | 72 | 60 | 58 |
| 239[6/] | (SEQ ID NO:239)EWLEAFYKKVLEKLKELF* | 11% | 44 | 49 | | sp |
| 240 | (SEQ ID NO:240)DWLKAFYDKVAEKLKEAF* | 10% | 16 | 68 | 59 | 57 |
| 241 | (SEQ ID NO:241)DWFKAFYDKVFEKFKEFF | 8% | | | | |
| 242[7/] | (SEQ ID NO:242)GIKKFLGSIWKFIKAFVG | 7% | | | | |
| 243 | (SEQ ID NO:243)DWFKAFYDKVAEKFKEAF | 5% | 10 | 64 | 50 | |
| 244[8/] | (SEQ ID NO:244)DWLKAFYDKVAEKLKEAF | 5% | 9 | 40 | 13 | 48 |
| 245 | (SEQ ID NO:245)DWLKAFYDKVFEKFKEFF | 4% | 38 | 77 | 70 | sp |
| 246[9/] | (SEQ ID NO:246)EWLEAFYKKVLEKLKELF | 4% | 18 | 44 | 47 | |
| 247 | (SEQ ID NO:247)DWFKAFYDKFFEKFKEFF | 3% | | | | |
| 248[10/] | (SEQ ID NO:248)EWLKAFYEKVLEKLKELF | 3% | 18 | 45 | 13 | |
| 249[11/] | (SEQ ID NO:249)EWLKAEYEKVEEKLKELF* | | | | | |
| 250[12/] | (SEQ ID NO:250)EWLKAEYEKVLEKLKELF* | | | | | |
| 251[13/] | (SEQ ID NO:251)EWLKAFYKKVLEKLKELF* | | | | | |
| 252 | (SEQ ID NO:252)PVLDLFRELLEQKLK* | | | | | |
| 253 | (SEQ ID NO:253)PVLDLFRELLEELKQK* | | | | | |
| 254 | (SEQ ID NO:254)PVLDLFRELLEKLKQK* | | | | | |
| 255 | (SEQ ID NO:255)PVLDLFRELLEKLQK* | | | | | |
| 256 | (SEQ ID NO:256)PVLDLFRELLEALKQK* | | | | | |

TABLE IX-continued

LCAT ACTIVATION EXHIBITED BY EXEMPLARY CORE PEPTIDES

| PEPTIDE | | ACTIVITY AMINO ACID SEQUENCE LCAT | He (%) free | He (%) mics | He (%) SUVs | He (%) TFE |
|---|---|---|---|---|---|---|
| 257 | (SEQ ID NO:257) | PVLDLFENLLERLKQK* | | | | |
| 258 | (SEQ ID NO:258) | PVLDLFRELLNELKQK* | | | | |

[1] Segrest's Consensus 22-mer peptide (Anantharamaiah et al., 1990, Arteriosclerosis 10(1):95–105).
[2] $[A^{13}]$-Consensus 22-mer peptide (Anantharamaiah et al., 1990, Arteriosclerosis 10(1):95–105).
[3] $[R^{13}]$-Consensus 22-mer peptide (Anantharamaiah et al., 1990, Arteriosclerosis 10(1):95–105).
[4] ID-3 peptide (Labeur et al., 1997, Arteriosclerosis, Thrombosis and Vascular Biology 17 (3):580–588).
[5] Ac-18AMOD-C(O)$NH_2$ peptide (Epand et al., 1987, J. Biol. Chem. 262 (19):9389–9396).
[6] Ac-18AM4-C(O)$NH_2$ peptide (Brasseur, 1993, Biochim. Biophys. Acta 1170:1–7).
[7] 18L peptide (Segrest et al., 1990, Proteins: Structure, Function and Genetics 8:103–117).
[8] 18A peptide (Anantharamaiah et al., 1985, J. Biol. Chem. 260(18):10248–10255).
[9] 18AM4 peptide (Rosseneu et al., WO93/25581; Corijn et al., 1993, Biochim. Biophys. Acta 1170:8–16).
[10] $(Glu^{1,8}; Leu^{5,11,17})$18A peptide (Epand et al., 1987, J. Biol. Chem. 262(19):9389–9396).
[11] Ac-18AM3-C(O)$NH_2$ (Rosseneu et al., WO93/25581).
[12] Ac-18AM2-C(O)$NH_2$ (Rosseneu et al., WO93/25581).
[13] Ac-18AM1-C(O)$NH_2$ (Rosseneu et al., WO93/25581).

In TABLE IX, * indicates peptides that are N-terminal acetylated and C-terminal amidated: * indicates peptides that are N-terminal dansylated: sp indicates peptides that exhibited solubility problems under the experimental conditions; X is Aib; Z is Nal; O is Orn; He (%) designates percent helicity; mics designates micelles: and—indicates deleted amino acids.

9. EXAMPLE
Pharmacokinetics of the ApoA-I Agonists

The following experiments can be used to demonstrate that the ApoA-I agonists are stable in the circulation and associate with the HDL component of plasma.

9.1. SYNTHESIS OF RADIOLABELLED PEPTIDE

Radiolabelled peptides are synthesized by coupling a $^{14}$C-labeled amino acid as the N-terminal amino acid. The synthesis is carried out according to L. Lapatsanis, Synthesis, 1983, 671–173. Briefly, 250 μM of unlabeled N-terminal amino acid is dissolved in 225 μl of a 9% $Na_2CO_3$ solution and added to a solution (9% $Na_2CO_3$) of 9.25 MBq (250 μM) $^{14}$C-labeled N-terminal amino acid. The liquid is cooled down to 0° C., mixed with 600 μM (202 mg) 9-fluorenylmethyl-N-succinimidylcarbonate (Fmoc-OSu) in 0.75 ml DMF and shaken at room temperature for 4 hr. Thereafter the mixture is extracted with Diethylether (2×5 ml) and chloroform (1×5 ml), the remaining aqueous phase is acidified with 30% HCl and extracted with chloroform (5×8 ml). The organic phase is dried over $Na_2SO_4$, filtered off and the volume was reduced under nitrogen flow to 5 ml. The purity is estimated by TLC ($CHCl_3$:MeOH:Hac, 9:1:0.1 v/v/v, stationary phase RPTLC silicagel 60, Merck, Germany).

The chloroform solution containing $^{14}$C-labeled Fmoc amino acid is used directly for peptide synthesis. A peptide resin containing amino acids 2–22 is synthesized automatically as described in Section 6. The sequence of the peptide is determined by Edman degradation. The coupling is performed as described in Section 6.1.

9.2. PHARMACOKINETICS IN MICE

In each experiment, 2.5 mg/kg radiolabelled peptide is injected intraperitoneally into mice which are fed normal mouse chow or the atherogenic Thomas-Harcroft modified diet (resulting in severely elevated VLDL and IDL cholesterol). Blood samples are taken at multiple time intervals for assessment of radioactivity in plasma.

9.3. STABILITY IN HUMAN SERUM

The stability of the ApoA-I agonists of the invention in human serum is demonstrated as described below.

9.3.1. EXPERIMENTAL METHODS

100 μg of $^{14}$C-labeled peptide (prepared as described in Section 9.1, supra), is mixed with 2 ml of fresh human plasma (at 37° C.) and delipidated either immediately (control sample) or after 8 days of incubation at 37° C. (test sample). Delipidation is carried out by extracting the lipids with an equal volume of 2:1 (v/v) chloroform:methanol.

The samples are loaded onto a reverse-phase $C_{18}$ HPLC column and eluted with a linear gradient (25–58% over 33 min.) of acetonitrile (containing 0.1% TFA). Elution profiles are followed by absorbance (220 nm) and radioactivity.

9.4. FORMATION OF Pre-β LIKE PARTICLES

The ability of the ApoA-I agonists of the invention to form pre-β-like particles is demonstrated as described below.

9.4.1. EXPERIMENTAL METHOD

Human HDL is isolated by KBr density ultra centrifugation at density d=1.21 g/ml to obtain top fraction followed by Superose 6 gel filtration chromatography to separate HDL from other lipoproteins. Isolated HDL is adjusted to a final concentration of 1.0 mg/ml with physiological saline based on protein content determined by Bradford protein assay. An aliquot of 300 μl is removed from the isolated HDL preparation and incubated with 100 µl $^{14}$C-labeled peptide for two hours at 37° C. Five separate incubations are analyzed including a blank containing 100 µl physiological saline and four dilutions of $^{14}$C-labeled peptide: (i) 0.20 µg/gl peptide:HDL, ratio=1:15; (ii) 0.30 µg/gl peptide:HDL, ratio=1:10; (iii) 0.60 µg/gl peptide:HDL, ratio=1:5; and (iv) 1.00 µg/µl peptide:HDL, ratio=1:3. Following the two hour incubation, a 200 µl aliquot of the sample (total volume=400 µl) is loaded onto a Superose 6 gel filtration column for lipoprotein separation and analysis, and 100 µl is used to determine total radioactivity loaded onto the column.

9.5. ASSOCIATION OF Apo-A-I AGONISTS WITH HUMAN LIPOPROTEINS

9.5.1. EXPERIMENTAL METHODS

The ability of the ApoA-I agonists of the invention to associate with human lipoprotein fractions is determined by incubating $^{14}$C-labeled peptide with each lipoprotein class (HDL, LDL and VLDL) and a mixture of the different lipoprotein classes.

HDL, LDL and VLDL are isolated by KBr density gradient ultracentrifugation at d=1.21 g/ml and purified by FPLC on a Superose 6B column size exclusion column (chromatography is carried out at a flow rate of 0.7 ml/min. and a running buffer of 10 mM Tris (pH 8), 115 mM NaCl, 2 mM EDTA and 0.01% NaN$_3$). $^{14}$C-labeled peptide is incubated with HDL, LDL and VLDL at a peptide:phospholipid ratio of 1:5 (mass ratio) for 2 h at 37° C. The required amount of lipoprotein (volumes based on amount needed to yield 1000 µg) is mixed with 0.2 ml of peptide stock solution (1 mg/ml) and the solution is brought up to 2.2 ml using 0.9% of NaCl.

After incubating for 2 hr. at 37° C., an aliquot (0.1 ml) is removed for liquid scintillation counting to determine the total radioactivity, the density of the remaining incubation mixture is adjusted to 1.21 g/ml with KBr, and the samples are centrifuged at 100,000 rpm (300,000 g) for 24 hours at 4° C. in a TLA 100.3 rotor using a Beckman tabletop ultracentrifuge. The resulting supernatant is fractionated by removing 0.3 ml aliquots from the top of each sample for a total of 5 fractions, and 0.05 ml of each fraction is used for liquid scintillation counting. The top two fractions contain the floating lipoproteins, the other fractions (3–5) correspond to proteins/peptides in solution.

9.6. THE ApoA-I AGONISTS OF THE INVENTION SELECTIVELY BIND HDL LIPIDS IN HUMAN PLASMA

9.6.1. EXPERIMENTAL METHOD

To demonstrate that the ApoA-I agonists of the invention selectively bind HDL proteins in human plasma, 2 ml of human plasma is incubated with 20, 40, 60, 80, and 100 µg of $^{14}$C-labeled peptide for 2 hr. at 37° C. The lipoproteins are separated by adjusting the density to 1.21 g/ml and centrifugation in a TLA 100.3 rotor at 100,000 rpm (300,000 g) for 36 hr. at 4° C. The top 900 µl (in 300 µl fractions) is taken for analysis. 50 µl from each 300 µl fraction is counted for radioactivity and 200 µl from each fraction is analyzed by FPLC (Superose 6/Superose 12 combination column).

10. EXAMPLE
The ApoA-I Agonists Promote Cholesterol Efflux

To demonstrate that the ApoA-I agonists of the invention promote cholesterol efflux, HepG2 hepatoma cells are plated into 6-well culture dishes and grown to confluence. Cells are labeled with $^3$H-cholesterol by drying the cholesterol, then adding 1% bovine serum albumin (BSA) in phosphate buffered saline (PBS), sonicating the solution, and adding 0.2 ml of this labeling solution and 1.8 ml growth medium to the cells, so that each well contains 2 µCi of radioactivity. Cells are incubated for 24 hr. with the labeling medium.

Peptide (or protein):DMPC complexes are prepared at a 1:2 peptide (or protein):DMPC ratio (w:w). To prepare the complexes, peptide or native human ApoA-I protein is added to a DMPC solution in PBS and incubated at room temperature overnight, by which time the solution will clarify. Peptide or protein concentration in the final solution is about 1 mg/ml.

Labeling media is removed from the cells and the cells are washed with PBS prior to addition of complexes. 1.6 ml of growth medium is added to each well, followed by peptide (or protein):DMPC complex and sufficient PBS to bring the final volume to 2 ml per well. The final peptide or ApoA-I concentrations are about 1, 2.5, 5, 7.5 and 25 µg/ml medium. After 24 hours of incubation at 37° C., the medium is removed, and the cells are washed with 2 ml of 1% BSA/PBS, followed by 2 washes with 2 ml each of PBS. The amount of $^3$H-cholesterol effluxed into the medium is determined by liquid scintillation counting.

11. EXAMPLE
Use of the ApoA-I Agonists in Animal Model Systems

The efficacy of the ApoA-I agonists of the invention can be demonstrated in rabbits using the protocols below.

11.1. PREPARATION OF THE PHOSPHOLIPID/PEPTIDE COMPLEXES

Small discoidal particles consisting of phospholipid (DPPC) and peptide are prepared following the cholate dialysis method. The phospholipid is dissolved in chloroform and dried under a stream of nitrogen. The peptide is dissolved in buffer (saline) at a concentration of 1–2 mg/ml. The lipid film is redissolved in buffer containing cholate (43° C.) and the peptide solution is added at a 3:1 phospholipid/peptide ratio. The mixture is incubated overnight at 43° C. and then dialyzed at 43° C. (24 hr.), room temperature (24 hr.) and 4° C. (24 hr.), with three changes of buffer (large volumes) at temperature point. The complexes are filter sterilized (0.22µ) for injection and storage at 4° C.

11.2. ISOLATION AND CHARACTERIZATION OF THE PEPTIDE/PHOSPHOLIPID PARTICLES

The particles are separated on a gel filtration column (Superose 6 HR). The position of the peak containing the particles is identified by measuring the phospholipid concentration in each fraction. From the elution volume, the Stokes radius can be determined. The concentration of peptide in the complex is determined by determining the phenylalanine content (by HPLC) following a 16 hr. acid hydrolysis.

11.3. INJECTION IN THE RABBIT

Male New Zealand White rabbits (2.5–3 kg) are injected intravenously with a dose of phospholipid/peptide complex (5–10 mg/kg bodyweight peptide or 10 mg/kg bodyweight ApoA-I (control)), expressed as peptide or protein content) in a single bolus injection not exceeding 10–15 ml. The animals are slightly sedated before the manipulations. Blood samples (collected on EDTA) are taken before and 5, 15, 30, 60, 240 and 1440 minutes after injection. The hematocrit (Hct) is determined for each sample. Samples are aliquoted and stored at −20° C. before analysis.

11.4. ANALYSIS OF THE RABBIT SERA

Plasma Lipids. The total plasma cholesterol, plasma triglycerides and plasma phospholipids is determined enzymatically using commercially available assays according to the manufacturer's protocols (Boehringer Mannheim, Mannheim, Germany and Biomérieux, 69280, Marcy-l'étoile, France).

LipoDrotein Profiles. The plasma lipoprotein profiles of the fractions obtained after the separation of the plasma into its lipoprotein fractions is determined by spinning in a sucrose density gradient. The fractions are collected and in each individual fraction the phospholipid and cholesterol content is measured enzymatically.

12. EXAMPLE

Preparation of Peptide-Lipid Complex by Co-Lyophilization Approach

The following protocol was utilized to prepare peptide-lipid complexes.

One mg of peptide 210 (SEQ ID NO:210) was dissolved in 250 μl HPLC grade methanol (Perkin Elmer) in a one ml clear glass vial with cap (Waters #WAT025054). Dissolving of the peptide was aided by occasional vortexing over a period of 10 minutes at room temperature. To this mixture an aliquot containing 3 mg dipalmitoyl-phosphatidylcholine (DPPC; Avanti Polar Lipids, 99% Purity, product #850355) from a 100 mg/ml stock solution in methanol was added. The volume of the mixture was brought to 400 μl by addition of methanol, and the mixture was further vortexed intermittently for a period of 10 minutes at room temperature. To the tube 200 μl of xylene (Sigma-Aldrich 99% pure, HPLC-grade) was added and the tubes were vortexed for 10 seconds. Two small holes were punched into the top of the tube with a 20 gauge syringe needle, the tube was frozen for 15 seconds in liquid nitrogen, and the tube was lyophilized overnight under vacuum. To the tube 200 mls of 0.9% NaCl solution was added. The tube was vortexed for 20 seconds. At this time the solution in the tube was milky in appearance. The tube was then incubated in a water bath for 30 minutes at 41° C. The solution became clear (i.e., similar to water in appearance) after a few minutes of incubation at 41° C.

12.1. CHARACTERIZATION OF COMPLEXES BY SUPEROSE 6 GEL FILTRATION CHROMATOGRAPHY

Peptide-phospholipid complexes containing peptide 210 (SEQ ID NO:210) were prepared by colyophilization as described above. The preparation contained 1 mg peptide and 3 mg DPPC by weight. After reconstituting the complexes in 200 μl of 0.9% NaCl, 20 μl (containing 100 μg peptide 210) of the complexes were applied to a Pharmacia Superose 6 column using 0.9% NaCl as the liquid phase at a flow rate of 0.5 ml/minute. The chromatography was monitored by absorbance or scattering of light of wavelength 280 nm. One ml fractions were collected. Aliquots containing 20 μl of the fractions were assayed for phospholipid content using the bioMerieux Phospholipides Enzymatique PAP 150 kit (#61491) according to the instructions supplied by the manufacturer. The vast majority of both phospholipid and UV absorbance were recovered together in a few fractions with peaks at approximately 15.1 mls. This elution volume corresponds to a Stokes' diameter of 106 Angstroms.

For comparison, a separate chromatogram of 20 μl of human $HDL_2$ was run under the same conditions and using the same column as the peptide 210 (SEQ ID NO:210) complexes. The $HDL_2$ was prepared as follows: 300 mls frozen human plasma (Mannheim Blutspendzentrale #1185190) was thawed, adjusted to density 1.25 with solid potassium bromide, and centrifuged 45 hours at 40,000 RPM using a Ti45 rotor (Beckman) at 20° C. The floating layer was collected, dialyzed against distilled water, adjusted to density 1.07 with solid potassium bromide, and centrifuged as described above for 70 hours. The bottom layer (at a level of one cm above the tube bottom) was collected, brought to 0.01% sodium azide, and stored at 4° C. for 4 days until chromatography. The column eluate was monitored by absorbance or scattering of light of wavelength 254 nm. A series of proteins of known molecular weight and Stokes' diameter were used as standards to calibrate the column for the calculation of Stokes' diameters of the particles (Pharmacia Gel Filtration Calibration Kit Instruction Manual, Pharmacia Laboratory Separation, Piscataway, N.J., revised April, 1985). The $HDL_2$ eluted with a retention volume of 14.8 mls, corresponding to a Stokes' diameter of 108 nm.

13. EXAMPLE

Preparation of Antibodies

To prepare antibodies to the ApoA-I agonists of the invention, peptide is conjugated to keyhole limpet hemocyanine (KLH; 1 mg peptide to 10 mg KLH). The KLH conjugate (LMG) is suspended in complete Freund's adjuvant and injected into rabbits at time 0, and boosted with 0.25 mg KLH conjugate at 4 weeks and again at 5 weeks. Pre-bleeds and six week post-bleeds are tested for antibody titer against authentic antigen by ELISA.

The production bleeds are pooled from 2 rabbits each. Antibodies directed exclusively against the peptide antigens are isolated as follows:

1. Free peptide is attached to cyanogen bromide activated Sepharose 4B (Pharmacia) according to the manufacturer's protocol.
2. The antisera is preabsorbed on a column of irrelevant peptides and on columns of irrelevant human and mouse serum proteins.
3. The pre-absorbed antisera is passed through the corresponding peptide column (see point 1).
4. The columns are washed with 0.1 M borate buffered saline (pH 8.2) and the bound antibodies are eluted using a low pH gradient step from pH 4.0 to pH 3.0 to pH 2.0 (0.1 M glycine buffer) and finally with 0.1 M HCl.
5. The eluted material is neutralized with excess borate saline, concentrated by ultrafiltration (Amicon, YM30) and dialyzed against borate saline.
6. The protein concentration is determined by absorbance at 280 nm.

The resulting antibodies are tested for species specificity using purified human ApoA-I or purified mouse ApoA-I in a direct ELISA binding assay.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated herein by reference for all purposes.

What is claimed is:

1. An ApoA-I agonist compound comprising:

(i) an 18 to 22-residue peptide or peptide analogue which forms an amphipathic α-helix in the presence of lipids and which comprises formula (I):

$$Z_1—X_1—X_2—X_3—X_4—X_5—X_6—X_7—X_8—X_9—X_{10}—X_{11}—X_{12}—X_{13}—X_{14}—X_{15}—X_{16}—X_{17}—X_{18}—Z_2$$

or a pharmaceutically acceptable salt thereof, wherein $X_1$ is Pro (P), Ala (A), Gly (G), Asn (N), Gln (Q) or D-pro (p);

$X_2$ is an aliphatic residue;

$X_3$ is Leu (L);

$X_4$ is an acidic residue;

$X_5$ is Leu (L) or Phe (F);

$X_6$ is Leu (L) or Phe (F);

$X_7$ is a basic residue;

$X_8$ is an acidic residue;

$X_9$ is Leu (L) or Trp (W);

$X_{10}$ is Leu (L) or Trp (W);

$X_{11}$ is an acidic residue or Asn (N);

$X_{12}$ is an acidic residue;

$X_{13}$ is Leu (L), Trp (W) or Phe (F);

$X_{14}$ is a basic residue or Leu (L);

$X_{15}$ is Gln (Q) or Asn (N);

$X_{16}$ is a basic residue;

$X_{17}$ is Leu (L);

$X_{18}$ is a basic residue;

wherein at least one L-enantiomeric residue of formula (I) other than Pro (P) at $X_1$ is replaced with an identical D-enantiomeric residue;

$Z_1$ is $H_2N—$, or $RC(O)NR—$;

$Z_2$ is $—C(O)NRR$, $—C(O)OR$ or $—C(O)OH$;

each R is independently —H, $(C_1–C_6)$ alkyl, $(C_1–C_6)$ alkenyl, $(C_1–C_6)$ alkynyl, $(C_5–C_{20})$ aryl, $(C_6–C_{26})$ alkaryl, 5–20 membered heteroaryl or 6-26 membered alkheteroaryl or a 1 to 4-residue peptide or peptide analogue in which one or more bonds between residues 1 through 4 are independently a substituted amide, an isostere of an amide or an amide mimetic;

each "—" between residues $X_1$ through $X_{18}$ independently designates an amide linkage, a substituted amide linkage, an isostere of an amide or an amide mimetic;

(ii) a 14 to 21-residue deleted peptide or peptide analogue according to formula (I) in which at least one and up to eight of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$ and $X_{18}$ are optionally deleted and wherein at least one remaining L-enantiomeric residue of formula I is replaced with an identical D-enantiomeric residue; or (iii) an 18 to 22-residue altered peptide or peptide analogue according to formula (I) in which at least one of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$ and $X_{18}$ is conservatively substituted and wherein at least one L-enantiomeric residue of the resulting altered peptide or peptide analogue is replaced with an identical D-enantiomeric residue; or an N-terminally blocked form, a C-terminally blocked form or an N- and C-terminally blocked form of formula (I).

2. The ApoA-I agonist compound of claim 1 which is the altered peptide or peptide analogue according to formula (I).

3. The ApoA-I agonist compound of claim 1 which is the deleted peptide or peptide analogue according to formula (I).

4. The ApoA-I agonist compound of claim 3 in which one or two helical turns of the peptide or peptide analogue is optionally deleted.

5. The ApoA-I agonist compound of claim 1 which is an 18-residue peptide or peptide analogue according to formula (I).

6. The ApoA-I agonist compound of claim 5 in which the "—" between residues designates —C(O)NH—;

$Z_1$ is $H_2N$—; and $Z_2$ is —C(O)OH or a salt thereof.

7. The ApoA-I agonist compound of claim 6 in which;

$X_1$ is Ala (A), Gly (G), Asn (N) or Pro (P);

$X_2$ is Ala (A), Val (V) or Leu (L);

$X_3$ is Leu (L);

$X_4$ is Asp (D) or Glu (E);

$X_5$ is Leu (L) or Phe (F);

$X_6$ is Leu (L) or Phe (F);

$X_7$ is Arg (R), Lys (K) or Orn;

$X_8$ is Asp (D) or Glu (E);

$X_9$ is Leu (L) or Trp (W);

$X_{10}$ is Leu (L) or Trp (W);

$X_{11}$ is Glu (E) or Asn (N);

$X_{12}$ is Glu (E);

$X_{13}$ is Leu (L), Trp (W) or Phe (F);

$X_{14}$ is Arg (R), Lys (K) or Orn;

$X_{15}$ is Gln (Q) or Asn (N);

$X_{16}$ is Arg (R), Lys (K) or Orn;

$X_{17}$ is Leu (L); and $X_{18}$ is Arg (R), Lys (K) or Orn.

8. A multimeric ApoA-I agonist compound which comprises formula (II):

  (II)

or a pharmaceutically acceptable salt thereof, wherein:

each m is independently an integer from 0 to 1;

n is an integer from 0 to 10;

each "HH" is independently a peptide or peptide analogue according to claim 1, the deleted peptide or peptide analogue according to claim 1 or the altered peptide or peptide analogue according to claim 1;

each "LL" is independently a bifunctional linker; and each "—" independently designates a covalent linkage; or an N-terminally blocked form, a C-terminally blocked form or an N- and C-terminally blocked form of formula (II).

9. A multimeric ApoA-I agonist compound which comprises formula (III):

  (III)

or a pharmaceutically acceptable salt thereof, wherein:

each X is independently $HH-[LL_m—HH-]_n LL_m—HH$;

each HH is independently a peptide or peptide analogue according to claim 1, the deleted peptide or peptide analogue according to claim 1 or the altered peptide or peptide analogue according to claim 1;

each LL is independently a bifunctional linker;

each m is independently an integer from 0 to 1;

each n is independently an integer from 0 to 8;

$N_{ya}$ and $N_{yb}$ are each independently a multifunctional linking moiety where $y_a$ and $y_b$ represent the number of functional groups on $N_{ya}$ and $N_{yb}$, respectively;

each $y_a$ or $y_b$ is independently an integer from 3 to 8;

p is an integer from 0 to 7; and each "—" independently designates a covalent bond; or an N-terminally blocked form, a C-terminally blocked form or an N- and C-terminally blocked form of formula (III).

10. A multimeric ApoA-I agonist compound which comprises formula (IV) or (V):

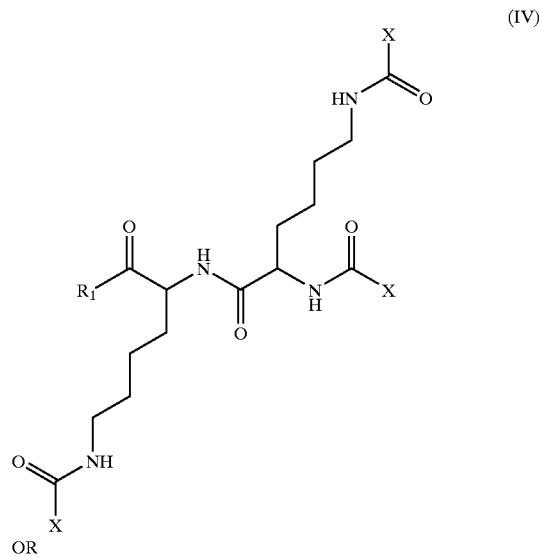

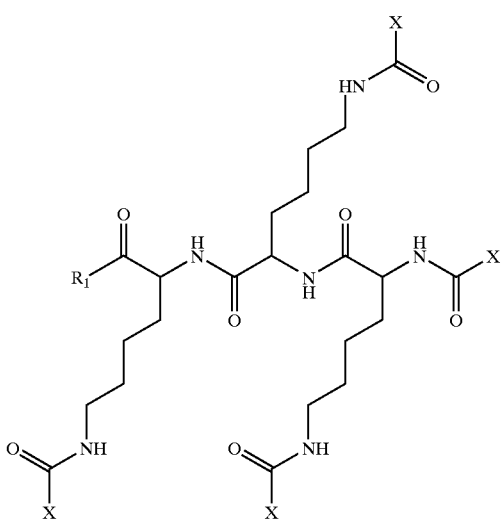

(V)

or a pharmaceutically acceptable salt thereof, wherein:
  each X is independently HH—[LL$_m$—HH—]$_n$LL$_m$—HH;
  each HH is independently a peptide or peptide analogue according to claim 1, the deleted peptide or peptide analogue according claim 1 or the altered peptide or peptide analogue according to claim 1;
  each LL is independently a bifunctional linker;
  each n is independently an integer from 0 to 1;
  each m is independently an integer from 0 to 8;
  R$_1$ is —OR or —NRR; and
  each R is independently —H, (C$_1$–C$_6$) alkyl, (C$_1$–C$_6$) alkenyl, (C$_1$–C$_6$) alkynyl, (C$_5$–C$_{20}$) aryl, (C$_6$–C$_{26}$) alkaryl, 5–20 membered heteroaryl or 6–26 membered alkheteroaryl; or
  an N-terminally blocked form or a C-terminally blocked form of formula (IV) or (V).

11. The multimeric ApoA-I agonist compound of claim 8, 9 or 10 in which the bifunctional linker is cleavable.

12. The multimeric ApoA-I agonist compound of claim 8, 9, or 10 in which n is 0.

13. The multimeric ApoA-I agonist compound of claim 10 in which m is 0.

14. The multimeric ApoA-I agonist compound of claim 8, 9 or 10 in which each HH is independently an altered peptide or peptide analogue.

15. The multimeric ApoA-I agonist compound of claim 1, 9, or 10 in which each HH is independently a deleted peptide or peptide analogue.

16. An ApoA-I agonist compound-lipid complex comprising a lipid and an ApoA-I agonist compound according to claim 1, 8, 9 or 10.

17. The ApoA-I agonist compound-lipid complex of claim 16 in which the lipid is sphingomyelin.

18. A pharmaceutical composition comprising a pharmaceutically acceptable carrier, excipient or diluent and an ApoA-I agonist compound according to claim 1, 8, 9 or 10.

19. A pharmaceutical composition comprising an ApoA-I agonist compound-lipid complex wherein the ApoA-I agonist compound-lipid complex is comprised of an ApoA-I agonist compound according to claim 1, 8, 9 or 10, a lipid and a pharmaceutically acceptable carrier, excipient or diluent.

20. The pharmaceutical composition of claim 19 in which the lipid is sphingomyelin.

21. The pharmaceutical composition of claim 20 which is a lyophilized powder.

22. A method of treating a subject suffering from a disorder associated with dyslipidemia, said method comprising the step of administering to the subject an effective amount of an ApoA-I agonist compound according to claim 1, 8, 9, or 10.

23. A method of treating a subject suffering from septic shock, said method comprising the step of administering to the subject an effective amount of an ApoA-I agonist compound according to claim 1, 8, 9, or 10.

24. The method of claim 22 in which said subject is a human.

25. The method of claim 23 in which said subject is a human.

26. The method of claim 23 in which about 0.5 mg/kg to about 100 mg/kg ApoA-I agonist compound is administered to said subject.

27. The method of claim 23 in which about 0.5 mg/kg to about 100 mg/kg ApoA-I agonist compound is administered to said subject.

* * * * *

SEQUENCE LISTING (1) GENERAL INFORMATION:

(iii) NUMBER OF SEQUENCES: 258

(2) INFORMATION FOR SEQ ID NO: 1:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 16
        (D) OTHER INFORMATION: Xaa = Naphthylalanine (xi) SEQUENCE DESCRIPTION: SEQ ID NO: 1:

Pro Val Leu Asp Leu Phe Arg Glu Leu Leu Asn Glu Leu Leu Glu Xaa
1               5                   10                  15

Leu Lys Gln Lys Leu Lys
            20

(2) INFORMATION FOR SEQ ID NO: 2:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 2:

Gly Val Leu Asp Leu Phe Arg Glu Leu Leu Asn Glu Leu Leu Glu Ala
1               5                   10                  15

Leu Lys Gln Lys Leu Lys Lys
            20

(2) INFORMATION FOR SEQ ID NO: 3:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 3:

Pro Val Leu Asp Leu Phe Arg Glu Leu Leu Asn Glu Leu Leu Glu Trp
1               5                   10                  15

Leu Lys Gln Lys Leu Lys
            20

(2) INFORMATION FOR SEQ ID NO: 4:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 4:

Pro Val Leu Asp Leu Phe Arg Glu Leu Leu Asn Glu Leu Leu Glu Ala
1               5                   10                  15
Leu Lys Gln Lys Leu Lys
            20

(2) INFORMATION FOR SEQ ID NO: 5:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO: 5:

Xaa Val Leu Asp Leu Phe Arg Glu Leu Leu Asn Glu Leu Leu Glu Ala
1               5                   10                  15
Leu Lys Gln Lys Leu Lys Lys
            20

(2) INFORMATION FOR SEQ ID NO: 6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 6:

Pro Val Leu Asp Leu Phe Arg Glu Leu Leu Asn Glu Xaa Leu Glu Ala
1               5                   10                  15
Leu Lys Gln Lys Leu Lys
            20

(2) INFORMATION FOR SEQ ID NO: 7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 7:

Pro Val Leu Asp Leu Phe Lys Glu Leu Leu Asn Glu Leu Leu Glu Ala
1               5                   10                  15
Leu Lys Gln Lys Leu Lys
            20

(2) INFORMATION FOR SEQ ID NO: 8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 8:

Pro Val Leu Asp Leu Phe Arg Glu Leu Leu Asn Glu Gly Leu Glu Ala
1               5                   10                  15

Leu Lys Gln Lys Leu Lys
            20

(2) INFORMATION FOR SEQ ID NO: 9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 9:

Pro Val Leu Asp Leu Phe Arg Glu Leu Gly Asn Glu Leu Leu Glu Ala
1               5                   10                  15

Leu Lys Gln Lys Leu Lys
            20

(2) INFORMATION FOR SEQ ID NO: 10:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 17
        (D) OTHER INFORMATION: Xaa = Naphthylalanine (xi) SEQUENCE DESCRIPTION: SEQ ID NO: 10:

Pro Val Leu Asp Leu Phe Arg Glu Leu Leu Asn Glu Leu Leu Glu Ala
1               5                   10                  15

Xaa Lys Gln Lys Leu Lys
            20

(2) INFORMATION FOR SEQ ID NO: 11:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 11:

Pro Val Leu Asp Leu Phe Lys Glu Leu Leu Gln Glu Leu Leu Glu Ala
1               5                   10                  15

Leu Lys Gln Lys Leu Lys
            20

(2) INFORMATION FOR SEQ ID NO: 12:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 12:

Pro Val Leu Asp Leu Phe Arg Glu Leu Leu Asn Glu Leu Leu Glu Ala
1               5                   10                  15

Gly Lys Gln Lys Leu Lys
            20

(2) INFORMATION FOR SEQ ID NO: 13:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 13:

Gly Val Leu Asp Leu Phe Arg Glu Leu Leu Asn Glu Gly Leu Glu Ala
1               5                   10                  15

Leu Lys Gln Lys Leu Lys
            20

(2) INFORMATION FOR SEQ ID NO: 14:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 18
        (D) OTHER INFORMATION: Xaa = Orn (xi) SEQUENCE DESCRIPTION: SEQ ID NO: 14:

Pro Val Leu Asp Leu Phe Arg Glu Leu Leu Asn Glu Leu Leu Glu Ala
1               5                   10                  15

Leu Xaa Gln Xaa Leu Xaa
            20

(2) INFORMATION FOR SEQ ID NO: 15:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 15:

Pro Val Leu Asp Leu Phe Arg Glu Leu Trp Asn Glu Leu Leu Glu Ala
1               5                   10                  15

Leu Lys Gln Lys Leu Lys
            20

(2) INFORMATION FOR SEQ ID NO: 16:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 16:

```
Pro Val Leu Asp Leu Arg Glu Leu Leu Asn Glu Leu Leu Glu Ala
1               5                   10                  15
Leu Lys Gln Lys Leu Lys
            20
```

(2) INFORMATION FOR SEQ ID NO: 17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 17:

```
Pro Val Leu Glu Leu Phe Lys Glu Leu Leu Gln Glu Leu Leu Glu Ala
1               5                   10                  15
Leu Lys Gln Lys Leu Lys
            20
```

(2) INFORMATION FOR SEQ ID NO: 18:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 18:

```
Gly Val Leu Asp Leu Phe Arg Glu Leu Leu Asn Glu Leu Leu Glu Ala
1               5                   10                  15
Leu Lys Gln Lys Leu Lys
            20
```

(2) INFORMATION FOR SEQ ID NO: 19:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO: 19:

```
Xaa Val Leu Asp Leu Phe Arg Glu Leu Leu Asn Glu Gly Leu Glu Ala
1               5                   10                  15
```

```
Leu Lys Gln Lys Leu Lys
            20

(2) INFORMATION FOR SEQ ID NO: 20:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 20:

Pro Val Leu Asp Leu Phe Arg Glu Gly Leu Asn Glu Leu Leu Glu Ala
1               5                   10                  15
Leu Lys Gln Lys Leu Lys
            20

(2) INFORMATION FOR SEQ ID NO: 21:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO: 21:

Xaa Val Leu Asp Leu Phe Arg Glu Leu Leu Asn Glu Leu Leu Glu Ala
1               5                   10                  15
Leu Lys Gln Lys Leu Lys
            20

(2) INFORMATION FOR SEQ ID NO: 22:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 22:

Pro Val Leu Asp Leu Phe Arg Glu Leu Leu Asn Glu Leu Leu Glu Gly
1               5                   10                  15
Leu Lys Gln Lys Leu Lys
            20

(2) INFORMATION FOR SEQ ID NO: 23:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 23:

Pro Leu Leu Glu Leu Phe Lys Glu Leu Leu Gln Glu Leu Leu Glu Ala
```

```
                  1               5              10              15
Leu Lys Gln Lys Leu Lys
             20

(2) INFORMATION FOR SEQ ID NO: 24:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 24:

Pro Val Leu Asp Leu Phe Arg Glu Leu Leu Asn Glu Leu Leu Glu Ala
 1               5                  10                  15
Leu Gln Lys Lys Leu Lys
             20

(2) INFORMATION FOR SEQ ID NO: 25:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 25:

Pro Val Leu Asp Phe Phe Arg Glu Leu Leu Asn Glu Xaa Leu Glu Ala
 1               5                  10                  15
Leu Lys Gln Lys Leu Lys
             20

(2) INFORMATION FOR SEQ ID NO: 26:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 26:

Pro Val Leu Asp Leu Phe Arg Glu Leu Leu Asn Glu Leu Leu Glu Leu
 1               5                  10                  15
Leu Lys Gln Lys Leu Lys
             20

(2) INFORMATION FOR SEQ ID NO: 27:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
```

```
            (A) NAME/KEY: Other
            (B) LOCATION: 14
            (D) OTHER INFORMATION: Xaa = Naphthylalanine (xi) SEQUENCE DESCRIPTION: SEQ ID NO: 27:

Pro Val Leu Asp Leu Phe Arg Glu Leu Leu Asn Glu Leu Xaa Glu Ala
1               5                   10                  15

Leu Lys Gln Lys Leu Lys
            20

(2) INFORMATION FOR SEQ ID NO: 28:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 28:

Pro Val Leu Asp Leu Phe Arg Glu Leu Leu Asn Glu Leu Trp Glu Ala
1               5                   10                  15

Leu Lys Gln Lys Leu Lys
            20

(2) INFORMATION FOR SEQ ID NO: 29:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 29:

Ala Val Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO: 30:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...22
            (D) OTHER INFORMATION: N-terminal dansylated peptide (xi) SEQUENCE DESCRIPTION: SEQ ID NO: 30:

Pro Val Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO: 31:

(i) SEQUENCE CHARACTERISTICS:
            (A) LENGTH: 22 amino acids
```

```
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO: 31:

Pro Val Leu Asp Leu Phe Leu Glu Leu Leu Asn Glu Xaa Leu Glu Ala
 1               5                  10                  15

Leu Lys Gln Lys Leu Lys
            20

(2) INFORMATION FOR SEQ ID NO: 32:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = Aib (xi) SEQUENCE DESCRIPTION: SEQ ID NO: 32:

Xaa Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO: 33:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 33:

Pro Val Leu Asp Leu Phe Arg Glu Lys Leu Asn Glu Leu Leu Glu Ala
 1               5                  10                  15

Leu Lys Gln Lys Leu Lys
            20

(2) INFORMATION FOR SEQ ID NO: 34:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 5
            (D) OTHER INFORMATION: Xaa = Naphthylalanine (xi) SEQUENCE DESCRIPTION: SEQ ID NO: 34:
```

```
Pro Val Leu Asp Xaa Phe Arg Glu Leu Leu Asn Glu Leu Leu Glu Ala
1               5                   10                  15
Leu Lys Gln Lys Leu Lys
            20
```

(2) INFORMATION FOR SEQ ID NO: 35:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 35:

```
Pro Val Leu Asp Trp Phe Arg Glu Leu Leu Asn Glu Leu Leu Glu Ala
1               5                   10                  15
Leu Lys Gln Lys Leu Lys
            20
```

(2) INFORMATION FOR SEQ ID NO: 36:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 36:

```
Pro Leu Leu Glu Leu Leu Lys Glu Leu Leu Gln Glu Leu Leu Glu Ala
1               5                   10                  15
Leu Lys Gln Lys Leu Lys
            20
```

(2) INFORMATION FOR SEQ ID NO: 37:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 37:

```
Pro Val Leu Asp Leu Phe Arg Glu Trp Leu Asn Glu Leu Leu Glu Ala
1               5                   10                  15
Leu Lys Gln Lys Leu Lys
            20
```

(2) INFORMATION FOR SEQ ID NO: 38:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 38:

Pro Val Leu Asp Leu Phe Arg Glu Leu Leu Asn Glu Xaa Leu Glu Ala
 1               5                  10                  15

Trp Lys Gln Lys Leu Lys
            20

(2) INFORMATION FOR SEQ ID NO: 39:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 39:

Pro Val Leu Asp Leu Phe Arg Glu Leu Leu Glu Glu Leu Leu Lys Ala
 1               5                  10                  15

Leu Lys Lys Lys Leu Lys
            20

(2) INFORMATION FOR SEQ ID NO: 40:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 40:

Pro Val Leu Asp Leu Phe Asn Glu Leu Leu Arg Glu Leu Leu Glu Ala
 1               5                  10                  15

Leu Gln Lys Lys Leu Lys
            20

(2) INFORMATION FOR SEQ ID NO: 41:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 41:

Pro Val Leu Asp Leu Trp Arg Glu Leu Leu Asn Glu Xaa Leu Glu Ala
 1               5                  10                  15

Leu Lys Gln Lys Leu Lys
            20

(2) INFORMATION FOR SEQ ID NO: 42:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO: 42:

Pro Val Leu Asp Glu Phe Arg Glu Lys Leu Asn Glu Xaa Trp Glu Ala
1               5                   10                  15

Leu Lys Gln Lys Leu Lys
            20

(2) INFORMATION FOR SEQ ID NO: 43:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO: 43:

Pro Val Leu Asp Glu Phe Arg Glu Lys Leu Trp Glu Xaa Leu Glu Ala
1               5                   10                  15

Leu Lys Gln Lys Leu Lys
            20

(2) INFORMATION FOR SEQ ID NO: 44:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...22
            (D) OTHER INFORMATION: All genetically encoded amino acids
                are in the D-configuration (xi) SEQUENCE DESCRIPTION: SEQ ID NO: 44:

Pro Val Leu Asp Glu Phe Arg Glu Lys Leu Asn Glu Xaa Leu Glu Ala
1               5                   10                  15

Leu Lys Gln Lys Leu Lys
            20

(2) INFORMATION FOR SEQ ID NO: 45:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13

(D) OTHER INFORMATION: Xaa = Aib (xi) SEQUENCE DESCRIPTION: SEQ ID NO: 45:

Pro Val Leu Asp Glu Phe Arg Glu Lys Leu Asn Glu Xaa Leu Glu Ala
1               5                   10                  15

Leu Lys Gln Lys Leu Lys
            20

(2) INFORMATION FOR SEQ ID NO: 46:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO: 46:

Pro Val Leu Asp Leu Phe Arg Glu Lys Leu Asn Glu Xaa Leu Glu Ala
1               5                   10                  15

Leu Lys Gln Lys Leu Lys
            20

(2) INFORMATION FOR SEQ ID NO: 47:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 47:

Val Leu Asp Leu Phe Arg Glu Leu Leu Asn Glu Gly Leu Glu Ala Leu
1               5                   10                  15

Lys Gln Lys Leu Lys
            20

(2) INFORMATION FOR SEQ ID NO: 48:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = D-Pro (xi) SEQUENCE DESCRIPTION: SEQ ID NO: 48:

Xaa Xaa Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO: 49:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 49:

Pro Val Leu Asp Leu Phe Arg Asn Leu Leu Glu Lys Leu Leu Glu Ala
1               5                   10                  15

Leu Glu Gln Lys Leu Lys
            20

(2) INFORMATION FOR SEQ ID NO: 50:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 50:

Pro Val Leu Asp Leu Phe Arg Glu Leu Leu Trp Glu Xaa Leu Glu Ala
1               5                   10                  15

Leu Lys Gln Lys Leu Lys
            20

(2) INFORMATION FOR SEQ ID NO: 51:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 51:

Pro Val Leu Asp Leu Phe Trp Glu Leu Leu Asn Glu Xaa Leu Glu Ala
1               5                   10                  15

Leu Lys Gln Lys Leu Lys
            20

(2) INFORMATION FOR SEQ ID NO: 52:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13

(D) OTHER INFORMATION: Xaa = Aib (xi) SEQUENCE DESCRIPTION: SEQ ID NO: 52:

Pro Val Trp Asp Glu Phe Arg Glu Lys Leu Asn Glu Xaa Leu Glu Ala
1               5                   10                  15
Leu Lys Gln Lys Leu Lys
            20

(2) INFORMATION FOR SEQ ID NO: 53:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 53:

Val Val Leu Asp Leu Phe Arg Glu Leu Leu Asn Glu Leu Leu Glu Ala
1               5                   10                  15
Leu Lys Gln Lys Leu Lys
            20

(2) INFORMATION FOR SEQ ID NO: 54:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 54:

Pro Val Leu Asp Leu Phe Arg Glu Leu Leu Asn Glu Trp Leu Glu Ala
1               5                   10                  15
Leu Lys Gln Lys Leu Lys
            20

(2) INFORMATION FOR SEQ ID NO: 55:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 55:

Pro Leu Phe Arg Glu Leu Leu Asn Glu Leu Leu Glu Ala Leu Lys Gln
1               5                   10                  15
Lys Leu Lys (2) INFORMATION FOR SEQ ID NO: 56:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 56:

```
Pro Val Leu Asp Leu Phe Arg Glu Leu Leu Asn Glu Leu Leu Glu Ala
1               5                   10                  15
Leu Lys Gln Lys Lys Lys
            20
```

(2) INFORMATION FOR SEQ ID NO: 57:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 57:

```
Pro Val Leu Asp Leu Phe Arg Asn Leu Leu Glu Glu Leu Leu Lys Ala
1               5                   10                  15
Leu Glu Gln Lys Leu Lys
            20
```

(2) INFORMATION FOR SEQ ID NO: 58:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 58:

```
Pro Val Leu Asp Glu Phe Arg Glu Lys Leu Asn Glu Xaa Leu Glu Ala
1               5                   10                  15
Leu Lys Gln Lys Leu
            20
```

(2) INFORMATION FOR SEQ ID NO: 59:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 59:

```
Leu Val Leu Asp Leu Phe Arg Glu Leu Leu Asn Glu Leu Leu Glu Ala
1               5                   10                  15
Leu Lys Gln Lys Leu Lys
            20
```

(2) INFORMATION FOR SEQ ID NO: 60:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 60:

Pro Val Leu Asp Leu Phe Arg Glu Leu Leu Asn Glu Leu Leu Glu Ala
1               5                   10                  15

Leu Lys Gln (2) INFORMATION FOR SEQ ID NO: 61:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 61:

Pro Val Leu Asp Glu Phe Arg Trp Lys Leu Asn Glu Xaa Leu Glu Ala
1               5                   10                  15

Leu Lys Gln Lys Leu Lys
            20

(2) INFORMATION FOR SEQ ID NO: 62:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 62:

Pro Val Leu Asp Glu Trp Arg Glu Lys Leu Asn Glu Xaa Leu Glu Ala
1               5                   10                  15

Leu Lys Gln Lys Leu Lys
            20

(2) INFORMATION FOR SEQ ID NO: 63:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 63:

Pro Val Leu Asp Phe Phe Arg Glu Lys Leu Asn Glu Xaa Leu Glu Ala
1               5                   10                  15

Leu Lys Gln Lys Leu Lys
            20

(2) INFORMATION FOR SEQ ID NO: 64:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 64:

Pro Trp Leu Asp Glu Phe Arg Glu Lys Leu Asn Glu Xaa Leu Glu Ala
 1               5                  10                  15
Leu Lys Gln Lys Leu Lys
            20

(2) INFORMATION FOR SEQ ID NO: 65:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 12
        (D) OTHER INFORMATION: Xaa = Aib (xi) SEQUENCE DESCRIPTION: SEQ ID NO: 65:

Val Leu Asp Glu Phe Arg Glu Lys Leu Asn Glu Xaa Leu Glu Ala Leu
 1               5                  10                  15
Lys Gln Lys Leu Lys
            20

(2) INFORMATION FOR SEQ ID NO: 66:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 66:

Pro Val Leu Asp Leu Phe Arg Asn Leu Leu Glu Glu Leu Leu Glu Ala
 1               5                  10                  15
Leu Gln Lys Lys Leu Lys
            20

(2) INFORMATION FOR SEQ ID NO: 67:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 67:

```
Val Leu Asp Leu Phe Arg Glu Leu Leu Asn Glu Leu Leu Glu Ala Leu
1               5                   10                  15

Lys Gln Lys Leu Lys
            20
```

(2) INFORMATION FOR SEQ ID NO: 68:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 68:

```
Pro Val Leu Asp Glu Phe Arg Glu Leu Leu Lys Glu Xaa Leu Glu Ala
1               5                   10                  15

Leu Lys Gln Lys Leu Lys
            20
```

(2) INFORMATION FOR SEQ ID NO: 69:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 69:

```
Pro Val Leu Asp Glu Phe Arg Lys Lys Leu Asn Glu Xaa Leu Glu Ala
1               5                   10                  15

Leu Lys Gln Lys Leu Lys
            20
```

(2) INFORMATION FOR SEQ ID NO: 70:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 70:

```
Pro Val Leu Asp Glu Phe Arg Glu Leu Leu Tyr Glu Xaa Leu Glu Ala
1               5                   10                  15

Leu Lys Gln Lys Leu Lys
            20
```

(2) INFORMATION FOR SEQ ID NO: 71:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 14
        (D) OTHER INFORMATION: Xaa = Aib (xi) SEQUENCE DESCRIPTION: SEQ ID NO: 71:

Pro Val Leu Asp Glu Phe Arg Glu Lys Leu Asn Glu Leu Xaa Glu Ala
 1               5                  10                  15

Leu Lys Gln Lys Leu Lys
            20

(2) INFORMATION FOR SEQ ID NO: 72:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 72:

Pro Val Leu Asp Leu Phe Arg Glu Leu Leu Asn Glu Xaa Leu Trp Ala
 1               5                  10                  15

Leu Lys Gln Lys Leu Lys
            20

(2) INFORMATION FOR SEQ ID NO: 73:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 73:

Pro Val Leu Asp Glu Phe Trp Glu Lys Leu Asn Glu Xaa Leu Glu Ala
 1               5                  10                  15

Leu Lys Gln Lys Leu Lys
            20

(2) INFORMATION FOR SEQ ID NO: 74:

(i) SEQUENCE CHARACTERISTICS:
        (A) LENGTH: 22 amino acids
        (B) TYPE: amino acid
        (C) STRANDEDNESS: single (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 74:

Pro Val Leu Asp Lys Phe Arg Glu Lys Leu Asn Glu Xaa Leu Glu Ala
1               5                   10                  15

Leu Lys Gln Lys Leu Lys
            20

(2) INFORMATION FOR SEQ ID NO: 75:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 75:

Pro Val Leu Asp Glu Phe Arg Glu Lys Leu Asn Glu Glu Leu Glu Ala
1               5                   10                  15

Leu Lys Gln Lys Leu Lys
            20

(2) INFORMATION FOR SEQ ID NO: 76:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 76:

Pro Val Leu Asp Glu Phe Arg Glu Leu Leu Phe Glu Xaa Leu Glu Ala
1               5                   10                  15

Leu Lys Gln Lys Leu Lys
            20

(2) INFORMATION FOR SEQ ID NO: 77:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 77:

Pro Val Leu Asp Glu Phe Arg Glu Lys Leu Asn Lys Xaa Leu Glu Ala

```
                  1               5                  10                 15
Leu Lys Gln Lys Leu Lys
            20

(2) INFORMATION FOR SEQ ID NO: 78:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 78:

Pro Val Leu Asp Glu Phe Arg Asp Lys Leu Asn Glu Xaa Leu Glu Ala
  1               5                  10                 15
Leu Lys Gln Lys Leu Lys
            20

(2) INFORMATION FOR SEQ ID NO: 79:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 79:

Pro Val Leu Asp Glu Phe Arg Glu Leu Leu Asn Glu Leu Leu Glu Ala
  1               5                  10                 15
Leu Lys Gln Lys Leu Lys
            20

(2) INFORMATION FOR SEQ ID NO: 80:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 80:

Pro Val Leu Asp Leu Phe Glu Arg Leu Leu Asn Glu Leu Leu Glu Ala
  1               5                  10                 15
Leu Gln Lys Lys Leu Lys
            20

(2) INFORMATION FOR SEQ ID NO: 81:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
```

(A) NAME/KEY: Other
        (B) LOCATION: 13
        (D) OTHER INFORMATION: Xaa = Aib (xi) SEQUENCE DESCRIPTION: SEQ ID NO: 81:

Pro Val Leu Asp Glu Phe Arg Glu Lys Leu Asn Trp Xaa Leu Glu Ala
1               5                   10                  15

Leu Lys Gln Lys Leu Lys
            20

(2) INFORMATION FOR SEQ ID NO: 82:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 11
        (D) OTHER INFORMATION: Xaa = Aib (xi) SEQUENCE DESCRIPTION: SEQ ID NO: 82:

Leu Asp Glu Phe Arg Glu Lys Leu Asn Glu Xaa Leu Glu Ala Leu Lys
1               5                   10                  15

Gln Lys Leu Lys
            20

(2) INFORMATION FOR SEQ ID NO: 83:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 83:

Pro Val Leu Asp Glu Phe Arg Glu Lys Leu Asn Glu Xaa Leu Glu Ala
1               5                   10                  15

Leu Trp Gln Lys Leu Lys
            20

(2) INFORMATION FOR SEQ ID NO: 84:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 84:

Pro Val Leu Asp Glu Phe Arg Glu Lys Leu Asn Glu Leu Leu Glu Ala
1               5                   10                  15

Leu Lys Gln Lys Leu Lys
            20

(2) INFORMATION FOR SEQ ID NO: 85:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 85:

```
Pro Leu Asp Leu Phe Arg Glu Leu Leu Asn Glu Leu Leu Glu Ala Leu
1               5                   10                  15
Lys Gln Lys Leu Lys
            20
```

(2) INFORMATION FOR SEQ ID NO: 86:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 86:

```
Pro Val Leu Glu Leu Phe Glu Arg Leu Leu Asp Glu Leu Leu Asn Ala
1               5                   10                  15
Leu Gln Lys Lys Leu Lys
            20
```

(2) INFORMATION FOR SEQ ID NO: 87:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All amino acids are in the D-
            configuration (xi) SEQUENCE DESCRIPTION: SEQ ID NO: 87:

```
Pro Leu Leu Glu Leu Leu Lys Glu Leu Leu Gln Glu Leu Leu Glu Ala
1               5                   10                  15
Leu Lys Gln Lys Leu Lys
            20
```

(2) INFORMATION FOR SEQ ID NO: 88:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 88:

Pro Val Leu Asp Lys Phe Arg Glu Leu Leu Asn Glu Xaa Leu Glu Ala
1               5                   10                  15

Leu Lys Gln Lys Leu Lys
            20

(2) INFORMATION FOR SEQ ID NO: 89:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 89:

Pro Val Leu Asp Glu Phe Arg Glu Lys Leu Asn Glu Xaa Leu Trp Ala
1               5                   10                  15

Leu Lys Gln Lys Leu Lys
            20

(2) INFORMATION FOR SEQ ID NO: 90:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 10
        (D) OTHER INFORMATION: Xaa = Aib (xi) SEQUENCE DESCRIPTION: SEQ ID NO: 90:

Asp Glu Phe Arg Glu Lys Leu Asn Glu Xaa Leu Glu Ala Leu Lys Gln
1               5                   10                  15

Lys Leu Lys (2) INFORMATION FOR SEQ ID NO: 91:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 91:

Pro Val Leu Asp Glu Phe Arg Glu Leu Leu Asn Glu Xaa Leu Glu Ala
1               5                   10                  15

Leu Lys Gln Lys Leu Lys
            20

(2) INFORMATION FOR SEQ ID NO: 92:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 92:

```
Pro Val Leu Asp Glu Phe Arg Glu Leu Tyr Asn Glu Xaa Leu Glu Ala
 1               5                  10                  15
Leu Lys Gln Lys Leu Lys
            20
```

(2) INFORMATION FOR SEQ ID NO: 93:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 93:

```
Pro Val Leu Asp Glu Phe Arg Glu Lys Leu Asn Glu Xaa Leu Lys Ala
 1               5                  10                  15
Leu Lys Gln Lys Leu Lys
            20
```

(2) INFORMATION FOR SEQ ID NO: 94:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 94:

```
Pro Val Leu Asp Glu Phe Arg Glu Lys Leu Asn Glu Ala Leu Glu Ala
 1               5                  10                  15
Leu Lys Gln Lys Leu Lys
            20
```

(2) INFORMATION FOR SEQ ID NO: 95:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:

(A) NAME/KEY: Other
            (B) LOCATION: 13
            (D) OTHER INFORMATION: Xaa = Aib (xi) SEQUENCE DESCRIPTION: SEQ ID NO: 95:

Pro Val Leu Asp Leu Phe Arg Glu Leu Leu Asn Leu Xaa Leu Glu Ala
1               5                   10                  15

Leu Lys Gln Lys Leu Lys
            20

(2) INFORMATION FOR SEQ ID NO: 96:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...22
            (D) OTHER INFORMATION: All genetically encoded amino acids
                are in the D-configuration (xi) SEQUENCE DESCRIPTION: SEQ ID NO: 96:

Pro Val Leu Asp Leu Phe Arg Glu Leu Leu Asn Glu Xaa Leu Glu Ala
1               5                   10                  15

Leu Lys Gln Lys Leu Lys
            20

(2) INFORMATION FOR SEQ ID NO: 97:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 97:

Pro Val Leu Asp Leu Phe Arg Glu Leu Leu Asn Glu Leu Leu Glu
1               5                   10                  15

FORMATION FOR SEQ ID NO: 98:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 98:

Pro Val Leu Asp Leu Phe Arg Glu Leu Leu Asn Glu Leu Glu Ala
1               5                   10                  15

Leu Lys Gln Lys Leu Lys
            20

(2) INFORMATION FOR SEQ ID NO: 99:

(i) SEQUENCE CHARACTERISTICS:
            (A) LENGTH: 22 amino acids
            (B) TYPE: amino acid
            (C) STRANDEDNESS: single (D) TOPOLOGY: linear (ii) MOLECULE TYPE: None (xi) SEQUENCE DESCRIPTION: SEQ ID NO: 99:

Lys Leu Lys Gln Lys Leu Ala Glu Leu Leu Glu Asn Leu Leu Glu Arg
1               5                   10                  15

Phe Leu Asp Leu Val Pro
            20

(2) INFORMATION FOR SEQ ID NO: 100:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (ix) FEATURE:
          (A) NAME/KEY: Other
          (B) LOCATION: 1...22
          (D) OTHER INFORMATION: All amino acids are in the D-
              configuration (xi) SEQUENCE DESCRIPTION: SEQ ID NO: 100:

Pro Val Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO: 101:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (ix) FEATURE:
          (A) NAME/KEY: Other
          (B) LOCATION: 13
          (D) OTHER INFORMATION: Xaa = Aib (xi) SEQUENCE DESCRIPTION: SEQ ID NO: 101:

Pro Val Leu Asp Leu Phe Arg Glu Leu Leu Asn Trp Xaa Leu Glu Ala
1               5                   10                  15

Leu Lys Gln Lys Leu Lys
            20

(2) INFORMATION FOR SEQ ID NO: 102:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (ix) FEATURE:
          (A) NAME/KEY: Other
          (B) LOCATION: 13
          (D) OTHER INFORMATION: Xaa = Aib (xi) SEQUENCE DESCRIPTION: SEQ ID NO: 102:

```
Pro Val Leu Asp Leu Phe Arg Glu Leu Leu Asn Leu Xaa Leu Glu Ala
1               5                   10                  15
Leu Lys Glu Lys Leu Lys
            20
```

(2) INFORMATION FOR SEQ ID NO: 103:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 103:

```
Pro Val Leu Asp Glu Phe Arg Glu Leu Leu Asn Glu Glu Leu Glu Ala
1               5                   10                  15
Leu Lys Gln Lys Leu Lys
            20
```

(2) INFORMATION FOR SEQ ID NO: 104:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 104:

```
Pro Leu Leu Asn Glu Leu Leu Glu Ala Leu Lys Gln Lys Leu Lys
1               5                   10                  15
```

FORMATION FOR SEQ ID NO: 105:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 105:

```
Pro Ala Ala Asp Ala Phe Arg Glu Ala Ala Asn Glu Ala Ala Glu Ala
1               5                   10                  15
Ala Lys Gln Lys Ala Lys
            20
```

(2) INFORMATION FOR SEQ ID NO: 106:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 106:

```
Pro Val Leu Asp Leu Phe Arg Glu Lys Leu Asn Glu Glu Leu Glu Ala
1               5                   10                  15
Leu Lys Gln Lys Leu Lys
            20
```

(2) INFORMATION FOR SEQ ID NO: 107:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All amino acids are in the D-
           configuration (xi) SEQUENCE DESCRIPTION: SEQ ID NO: 107:

```
Lys Leu Lys Gln Lys Leu Ala Glu Leu Leu Glu Asn Leu Leu Glu Arg
 1               5                  10                  15
Phe Leu Asp Leu Val Pro
            20
```

(2) INFORMATION FOR SEQ ID NO: 108:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 108:

```
Pro Val Leu Asp Leu Phe Arg Trp Leu Leu Asn Glu Xaa Leu Glu Ala
 1               5                  10                  15
Leu Lys Gln Lys Leu Lys
            20
```

(2) INFORMATION FOR SEQ ID NO: 109:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 109:

```
Pro Val Leu Asp Glu Phe Arg Glu Lys Leu Asn Glu Arg Leu Glu Ala
 1               5                  10                  15
Leu Lys Gln Lys Leu Lys
            20
```

(2) INFORMATION FOR SEQ ID NO: 110:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None

```
    (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO: 110:

Pro Val Leu Asp Glu Phe Arg Glu Lys Leu Asn Glu Xaa Xaa Glu Ala
1               5                   10                  15

Leu Lys Gln Lys Leu Lys
            20

(2) INFORMATION FOR SEQ ID NO: 111:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO: 111:

Pro Val Leu Asp Glu Phe Arg Glu Lys Leu Trp Glu Xaa Trp Glu Ala
1               5                   10                  15

Leu Lys Gln Lys Leu Lys
            20

(2) INFORMATION FOR SEQ ID NO: 112:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO: 112:

Pro Val Leu Asp Glu Phe Arg Glu Lys Leu Asn Glu Xaa Ser Glu Ala
1               5                   10                  15

Leu Lys Gln Lys Leu Lys
            20

(2) INFORMATION FOR SEQ ID NO: 113:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 113:

Pro Val Leu Asp Glu Phe Arg Glu Lys Leu Asn Glu Pro Leu Glu Ala
1               5                   10                  15

Leu Lys Gln Lys Leu Lys
            20
```

(2) INFORMATION FOR SEQ ID NO: 114:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 114:

Pro Val Leu Asp Glu Phe Arg Glu Lys Leu Asn Glu Xaa Met Glu Ala
1               5                   10                  15

Leu Lys Gln Lys Leu Lys
            20

(2) INFORMATION FOR SEQ ID NO: 115:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 115:

Pro Lys Leu Asp Glu Phe Arg Glu Lys Leu Asn Glu Xaa Leu Glu Ala
1               5                   10                  15

Leu Lys Gln Lys Leu Lys
            20

(2) INFORMATION FOR SEQ ID NO: 116:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 116:

Pro His Leu Asp Glu Phe Arg Glu Lys Leu Asn Glu Xaa Leu Glu Ala
1               5                   10                  15

Leu Lys Gln Lys Leu Lys
            20

(2) INFORMATION FOR SEQ ID NO: 117:

(i) SEQUENCE CHARACTERISTICS:
        (A) LENGTH: 22 amino acids
        (B) TYPE: amino acid (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 117:

Pro Glu Leu Asp Glu Phe Arg Glu Lys Leu Asn Glu Xaa Leu Glu Ala
1               5                   10                  15

Leu Lys Gln Lys Leu Lys
            20

(2) INFORMATION FOR SEQ ID NO: 118:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO: 118:

Pro Val Leu Asp Glu Phe Arg Glu Lys Leu Asn Glu Xaa Leu Glu Ala
1               5                   10                  15

Leu Glu Gln Lys Leu Lys
            20

(2) INFORMATION FOR SEQ ID NO: 119:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 17
        (D) OTHER INFORMATION: Xaa = Aib (xi) SEQUENCE DESCRIPTION: SEQ ID NO: 119:

Pro Val Leu Asp Glu Phe Arg Glu Lys Leu Asn Glu Glu Leu Glu Ala
1               5                   10                  15

Xaa Lys Gln Lys Leu Lys
            20

(2) INFORMATION FOR SEQ ID NO: 120:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other (B) LOCATION: 16
            (D) OTHER INFORMATION: Xaa = Aib (xi) SEQUENCE DESCRIPTION: SEQ ID NO: 120:

Pro Val Leu Asp Glu Phe Arg Glu Lys Leu Asn Glu Glu Leu Glu Xaa
1               5                   10                  15

Leu Lys Gln Lys Leu Lys
            20

(2) INFORMATION FOR SEQ ID NO: 121:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 121:

Pro Val Leu Asp Glu Phe Arg Glu Lys Leu Asn Glu Glu Leu Glu Ala
1               5                   10                  15

Leu Trp Gln Lys Leu Lys
            20

(2) INFORMATION FOR SEQ ID NO: 122:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 122:

Pro Val Leu Asp Glu Phe Arg Glu Lys Leu Asn Glu Glu Leu Glu Trp
1               5                   10                  15

Leu Lys Gln Lys Leu Lys
            20

(2) INFORMATION FOR SEQ ID NO: 123:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 123:

Gln Val Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO: 124:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None

```
    (ix) FEATURE:
         (A) NAME/KEY: Other
         (B) LOCATION: 18
         (D) OTHER INFORMATION: Xaa = Orn (xi) SEQUENCE DESCRIPTION: SEQ ID NO: 124:

Pro Val Leu Asp Leu Phe Xaa Glu Leu Leu Asn Glu Leu Leu Glu Ala
1               5                   10                  15

Leu Xaa Gln Xaa Leu Xaa
            20

(2) INFORMATION FOR SEQ ID NO: 125:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO: 125:

Asn Val Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO: 126:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO: 126:

Pro Val Leu Asp Leu Phe Arg Glu Leu Leu Asn Glu Leu Gly Glu Ala
1               5                   10                  15

Leu Lys Gln Lys Leu Lys
            20

(2) INFORMATION FOR SEQ ID NO: 127:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO: 127:

Pro Val Leu Asp Leu Phe Arg Glu Leu Leu Asn Glu Leu Leu Glu Leu
1               5                   10                  15

Leu Lys Gln Lys Leu Lys
            20

(2) INFORMATION FOR SEQ ID NO: 128:

(i) SEQUENCE CHARACTERISTICS:
         (A) LENGTH: 22 amino acids
         (B) TYPE: amino acid
         (C) STRANDEDNESS: single
         (D) TOPOLOGY: linear
```

(ii) MOLECULE TYPE: None (xi) SEQUENCE DESCRIPTION: SEQ ID NO: 128:

Pro Val Leu Asp Leu Phe Arg Glu Leu Leu Asn Glu Leu Leu Glu Phe
 1               5                  10                  15

Leu Lys Gln Lys Leu Lys
            20

(2) INFORMATION FOR SEQ ID NO: 129:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 129:

Pro Val Leu Glu Leu Phe Asn Asp Leu Leu Arg Glu Leu Leu Glu Ala
 1               5                  10                  15

Leu Gln Lys Lys Leu Lys
            20

(2) INFORMATION FOR SEQ ID NO: 130:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 130:

Pro Val Leu Glu Leu Phe Asn Asp Leu Leu Arg Glu Leu Leu Glu Ala
 1               5                  10                  15

Leu Lys Gln Lys Leu Lys
            20

(2) INFORMATION FOR SEQ ID NO: 131:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 131:

Pro Val Leu Glu Leu Phe Lys Glu Leu Leu Asn Glu Leu Leu Asp Ala
 1               5                  10                  15

Leu Arg Gln Lys Leu Lys
            20

(2) INFORMATION FOR SEQ ID NO: 132:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 132:

```
Pro Val Leu Asp Leu Phe Arg Glu Leu Leu Glu Asn Leu Leu Glu Ala
1               5                   10                  15
Leu Gln Lys Lys Leu Lys
            20
```

(2) INFORMATION FOR SEQ ID NO: 133:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 133:

```
Pro Val Leu Glu Leu Phe Glu Arg Leu Leu Glu Asp Leu Leu Gln Ala
1               5                   10                  15
Leu Asn Lys Lys Leu Lys
            20
```

(2) INFORMATION FOR SEQ ID NO: 134:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 134:

```
Pro Val Leu Glu Leu Phe Glu Arg Leu Leu Glu Asp Leu Leu Lys Ala
1               5                   10                  15
Leu Asn Gln Lys Leu Lys
            20
```

(2) INFORMATION FOR SEQ ID NO: 135:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 135:

```
Asp Val Leu Asp Leu Phe Arg Glu Leu Leu Asn Glu Leu Leu Glu Ala
1               5                   10                  15
Leu Lys Gln Lys Leu Lys
            20
```

(2) INFORMATION FOR SEQ ID NO: 136:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 136:

```
Pro Ala Leu Glu Leu Phe Lys Asp Leu Leu Gln Glu Leu Leu Glu Ala
1               5                   10                  15
```

```
Leu Lys Gln Lys Leu Lys
            20

(2) INFORMATION FOR SEQ ID NO: 137:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 17
        (D) OTHER INFORMATION: Xaa = Naphthylalanine (xi) SEQUENCE DESCRIPTION: SEQ ID NO: 137:

Pro Val Leu Asp Leu Phe Arg Glu Leu Leu Asn Glu Gly Leu Glu Ala
 1               5                  10                  15
Xaa Lys Gln Lys Leu Lys
            20

(2) INFORMATION FOR SEQ ID NO: 138:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 138:

Pro Val Leu Asp Leu Phe Arg Glu Leu Leu Asn Glu Gly Leu Glu Trp
 1               5                  10                  15
Leu Lys Gln Lys Leu Lys
            20

(2) INFORMATION FOR SEQ ID NO: 139:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 139:

Pro Val Leu Asp Leu Phe Arg Glu Leu Trp Asn Glu Gly Leu Glu Ala
 1               5                  10                  15
Leu Lys Gln Lys Leu Lys
            20

(2) INFORMATION FOR SEQ ID NO: 140:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
```

(B) LOCATION: 18
            (D) OTHER INFORMATION: Xaa = Orn (xi) SEQUENCE DESCRIPTION: SEQ ID NO: 140:

Pro Val Leu Asp Leu Phe Arg Glu Leu Leu Asn Glu Gly Leu Glu Ala
 1               5                  10                  15

Leu Xaa Gln Xaa Leu Xaa
            20

(2) INFORMATION FOR SEQ ID NO: 141:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 141:

Pro Val Leu Asp Phe Phe Arg Glu Leu Leu Asn Glu Gly Leu Glu Ala
 1               5                  10                  15

Leu Lys Gln Lys Leu Lys
            20

(2) INFORMATION FOR SEQ ID NO: 142:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 142:

Pro Val Leu Glu Leu Phe Arg Glu Leu Leu Asn Glu Gly Leu Glu Ala
 1               5                  10                  15

Leu Lys Gln Lys Leu Lys
            20

(2) INFORMATION FOR SEQ ID NO: 143:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: N-terminal acetylated and
            C-terminal amidated peptide (xi) SEQUENCE DESCRIPTION: SEQ ID NO: 143:

Pro Val Leu Asp Leu Phe Arg Glu Leu Leu Asn Glu Gly Leu Glu Ala
 1               5                  10                  15

Leu Lys Gln Lys Leu Lys
            20

(2) INFORMATION FOR SEQ ID NO: 144:

(i) SEQUENCE CHARACTERISTICS:
        (A) LENGTH: 22 amino acids (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = D-Pro (xi) SEQUENCE DESCRIPTION: SEQ ID NO: 144:

Xaa Val Leu Glu Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 145:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 145:

Gly Val Leu Glu Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 146:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 146:

Pro Val Leu Glu Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 147:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 147:

Pro Val Leu Glu Leu Phe Glu Asn Leu Leu Glu Arg Leu Phe Asp Ala
1               5                   10                  15

Leu Gln Lys Lys Leu Lys
            20

(2) INFORMATION FOR SEQ ID NO: 148:

```
      (i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 148:

Pro Val Leu Glu Leu Phe Glu Asn Leu Leu Glu Arg Leu Gly Asp Ala
1               5                   10                  15

Leu Gln Lys Lys Leu Lys
            20

(2) INFORMATION FOR SEQ ID NO: 149:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 149:

Pro Val Leu Glu Leu Phe Glu Asn Leu Trp Glu Arg Leu Leu Asp Ala
1               5                   10                  15

Leu Gln Lys Lys Leu Lys
            20

(2) INFORMATION FOR SEQ ID NO: 150:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 150:

Pro Leu Leu Glu Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 151:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 151:

Pro Val Leu Glu Leu Phe Glu Asn Leu Gly Glu Arg Leu Leu Asp Ala
1               5                   10                  15

Leu Gln Lys Lys Leu Lys
            20

(2) INFORMATION FOR SEQ ID NO: 152:

(i) SEQUENCE CHARACTERISTICS:
          (A) LENGTH: 22 amino acids
          (B) TYPE: amino acid
```

(C) STRANDEDNESS: single
        (D) TOPOLOGY: linear (ii) MOLECULE TYPE: None (xi) SEQUENCE DESCRIPTION: SEQ ID NO: 152:

Pro Val Phe Glu Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 153:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 153:

Ala Val Leu Glu Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 154:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 154:

Pro Val Leu Glu Leu Phe Glu Asn Leu Leu Glu Arg Gly Leu Asp Ala
1               5                   10                  15

Leu Gln Lys Lys Leu Lys
            20

(2) INFORMATION FOR SEQ ID NO: 155:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 155:

Pro Val Leu Glu Leu Phe Leu Asn Leu Trp Glu Arg Leu Leu Asp Ala
1               5                   10                  15

Leu Gln Lys Lys Leu Lys
            20

(2) INFORMATION FOR SEQ ID NO: 156:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 156:

Pro Val Leu Glu Leu Phe Leu Asn Leu Leu Glu Arg Leu Leu Asp Ala
1               5                   10                  15

Leu Gln Lys Lys Leu Lys
            20

(2) INFORMATION FOR SEQ ID NO: 157:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 157:

Pro Val Leu Glu Phe Phe Glu Asn Leu Leu Glu Arg Leu Leu Asp Ala
1               5                   10                  15

Leu Gln Lys Lys Leu Lys
            20

(2) INFORMATION FOR SEQ ID NO: 158:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 158:

Pro Val Leu Glu Leu Phe Leu Asn Leu Leu Glu Arg Leu Leu Asp Trp
1               5                   10                  15

Leu Gln Lys Lys Leu Lys
            20

(2) INFORMATION FOR SEQ ID NO: 159:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 159:

Pro Val Leu Asp Leu Phe Glu Asn Leu Leu Glu Arg Leu Leu Asp Ala
1               5                   10                  15

Leu Gln Lys Lys Leu Lys
            20

(2) INFORMATION FOR SEQ ID NO: 160:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 160:

```
Pro Val Leu Glu Leu Phe Glu Asn Leu Leu Glu Arg Leu Leu Asp Trp
1               5                   10                  15

Leu Gln Lys Lys Leu Lys
            20
```

(2) INFORMATION FOR SEQ ID NO: 161:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 161:

```
Pro Val Leu Glu Leu Phe Glu Asn Leu Leu Glu Arg Leu Leu Glu Ala
1               5                   10                  15

Leu Gln Lys Lys Leu Lys
            20
```

(2) INFORMATION FOR SEQ ID NO: 162:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 162:

```
Pro Val Leu Glu Leu Phe Glu Asn Trp Leu Glu Arg Leu Leu Asp Ala
1               5                   10                  15

Leu Gln Lys Lys Leu Lys
            20
```

(2) INFORMATION FOR SEQ ID NO: 163:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 163:

```
Pro Val Leu Glu Leu Phe Glu Asn Leu Leu Glu Arg Leu Trp Asp Ala
1               5                   10                  15

Leu Gln Lys Lys Leu Lys
            20
```

(2) INFORMATION FOR SEQ ID NO: 164:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 164:

```
Pro Val Leu Glu Leu Phe Glu Asn Leu Leu Glu Arg Leu Leu Asp Ala
1               5                   10                  15
```

```
Trp Gln Lys Lys Leu Lys
        20
```

(2) INFORMATION FOR SEQ ID NO: 165:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 165:

```
Pro Val Leu Glu Leu Phe Glu Asn Leu Leu Glu Arg Leu Leu Asp Leu
 1               5                  10                  15
Leu Gln Lys Lys Leu Lys
        20
```

(2) INFORMATION FOR SEQ ID NO: 166:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 166:

```
Pro Val Leu Glu Leu Phe Leu Asn Leu Leu Glu Lys Leu Leu Asp Ala
 1               5                  10                  15
Leu Gln Lys Lys Leu Lys
        20
```

(2) INFORMATION FOR SEQ ID NO: 167:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 167:

```
Pro Val Leu Glu Leu Phe Glu Asn Gly Leu Glu Arg Leu Leu Asp Ala
 1               5                  10                  15
Leu Gln Lys Lys Leu Lys
        20
```

(2) INFORMATION FOR SEQ ID NO: 168:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 168:

```
Pro Val Leu Glu Leu Phe Glu Gln Leu Leu Glu Lys Leu Leu Asp Ala
 1               5                  10                  15
Leu Gln Lys Lys Leu Lys
        20
```

(2) INFORMATION FOR SEQ ID NO: 169:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO: 169:

Pro Val Leu Glu Leu Phe Glu Asn Leu Leu Glu Lys Leu Leu Asp Ala
1               5                   10                  15

Leu Gln Lys Lys Leu Lys
            20

(2) INFORMATION FOR SEQ ID NO: 170:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: None (ix) FEATURE:
       (A) NAME/KEY: Other
       (B) LOCATION: 12
       (D) OTHER INFORMATION: Xaa = Orn (xi) SEQUENCE DESCRIPTION: SEQ ID NO: 170:

Pro Val Leu Glu Leu Phe Glu Asn Leu Leu Glu Xaa Leu Leu Asp Ala
1               5                   10                  15

Leu Gln Xaa Xaa Leu Xaa
            20

(2) INFORMATION FOR SEQ ID NO: 171:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO: 171:

Pro Val Leu Glu Leu Phe Glu Asn Leu Leu Glu Lys Leu Leu Asp Leu
1               5                   10                  15

Leu Gln Lys Lys Leu Lys
            20

(2) INFORMATION FOR SEQ ID NO: 172:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO: 172:

Pro Val Leu Glu Leu Phe Leu Asn Leu Leu Glu Arg Leu Gly Asp Ala
1               5                   10                  15

```
Leu Gln Lys Lys Leu Lys
        20

(2) INFORMATION FOR SEQ ID NO: 173:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 173:

Pro Val Leu Asp Leu Phe Asp Asn Leu Leu Asp Arg Leu Leu Asp Leu
1               5                   10                  15

Leu Asn Lys Lys Leu Lys
        20

(2) INFORMATION FOR SEQ ID NO: 174:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All amino acids are in the D-
            configuration (xi) SEQUENCE DESCRIPTION: SEQ ID NO: 174:

Pro Val Leu Glu Leu Phe Glu Asn Leu Leu Glu Arg Leu Leu Asp Ala
1               5                   10                  15

Leu Gln Lys Lys Leu Lys
        20

(2) INFORMATION FOR SEQ ID NO: 175:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 175:

Pro Val Leu Glu Leu Phe Glu Asn Leu Leu Glu Arg Leu Leu Glu Leu
1               5                   10                  15

Leu Asn Lys Lys Leu Lys
        20

(2) INFORMATION FOR SEQ ID NO: 176:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 176:
```

```
Pro Val Leu Glu Leu Trp Glu Asn Leu Leu Glu Arg Leu Leu Asp Ala
1               5                   10                  15
Leu Gln Lys Lys Leu Lys
            20
```

(2) INFORMATION FOR SEQ ID NO: 177:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 177:

```
Gly Val Leu Glu Leu Phe Leu Asn Leu Leu Glu Arg Leu Leu Asp Ala
1               5                   10                  15
Leu Gln Lys Lys Leu Lys
            20
```

(2) INFORMATION FOR SEQ ID NO: 178:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 178:

```
Pro Val Leu Glu Leu Phe Asp Asn Leu Leu Glu Lys Leu Leu Glu Ala
1               5                   10                  15
Leu Gln Lys Lys Leu Arg
            20
```

(2) INFORMATION FOR SEQ ID NO: 179:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 179:

```
Pro Val Leu Glu Leu Phe Asp Asn Leu Leu Glu Arg Leu Leu Asp Ala
1               5                   10                  15
Leu Gln Lys Lys Leu Lys
            20
```

(2) INFORMATION FOR SEQ ID NO: 180:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 180:

```
Pro Val Leu Glu Leu Phe Asp Asn Leu Leu Asp Lys Leu Leu Asp Ala
1               5                   10                  15
```

Leu Gln Lys Lys Leu Arg
        20

(2) INFORMATION FOR SEQ ID NO: 181:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 181:

Pro Val Leu Glu Leu Phe Glu Asn Leu Leu Glu Arg Trp Leu Asp Ala
1               5                   10                  15

Leu Gln Lys Lys Leu Lys
        20

(2) INFORMATION FOR SEQ ID NO: 182:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 182:

Pro Val Leu Glu Leu Phe Glu Asn Leu Leu Glu Lys Leu Leu Glu Ala
1               5                   10                  15

Leu Gln Lys Lys Leu Lys
        20

(2) INFORMATION FOR SEQ ID NO: 183:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 183:

Pro Leu Leu Glu Leu Phe Glu Asn Leu Leu Glu Lys Leu Leu Asp Ala
1               5                   10                  15

Leu Gln Lys Lys Leu Lys
        20

(2) INFORMATION FOR SEQ ID NO: 184:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 184:

Pro Val Leu Glu Leu Phe Leu Asn Leu Leu Glu Arg Leu Leu Asp Ala
1               5                   10                  15

Trp Gln Lys Lys Leu Lys
        20

(2) INFORMATION FOR SEQ ID NO: 185:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 19
        (D) OTHER INFORMATION: Xaa = Orn (xi) SEQUENCE DESCRIPTION: SEQ ID NO: 185:

```
Pro Val Leu Glu Leu Phe Glu Asn Leu Leu Glu Arg Leu Leu Asp Ala
1               5                   10                  15
Leu Gln Xaa Xaa Leu Xaa
            20
```

(2) INFORMATION FOR SEQ ID NO: 186:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 186:

```
Pro Val Leu Glu Leu Phe Glu Gln Leu Leu Glu Arg Leu Leu Asp Ala
1               5                   10                  15
Leu Gln Lys Lys Leu Lys
            20
```

(2) INFORMATION FOR SEQ ID NO: 187:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 187:

```
Pro Val Leu Glu Leu Phe Glu Asn Leu Leu Glu Arg Leu Leu Asp Ala
1               5                   10                  15
Leu Asn Lys Lys Leu Lys
            20
```

(2) INFORMATION FOR SEQ ID NO: 188:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 188:

```
Pro Val Leu Glu Leu Phe Glu Asn Leu Leu Asp Arg Leu Leu Asp Ala
1               5                   10                  15
Leu Gln Lys Lys Leu Lys
```

20

(2) INFORMATION FOR SEQ ID NO: 189:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 189:

```
Asp Val Leu Glu Leu Phe Glu Asn Leu Leu Glu Arg Leu Leu Asp Ala
 1               5                  10                  15
Leu Gln Lys Lys Leu Lys
            20
```

(2) INFORMATION FOR SEQ ID NO: 190:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 190:

```
Pro Val Leu Glu Phe Trp Asp Asn Leu Leu Asp Lys Leu Leu Asp Ala
 1               5                  10                  15
Leu Gln Lys Lys Leu Arg
            20
```

(2) INFORMATION FOR SEQ ID NO: 191:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 191:

```
Pro Val Leu Asp Leu Leu Arg Glu Leu Leu Glu Glu Leu Lys Gln Lys
 1               5                  10                  15
Leu Lys
```

(2) INFORMATION FOR SEQ ID NO: 192:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and C-terminal amidated (xi) SEQUENCE DESCRIPTION: SEQ ID NO: 192:

Pro Val Leu Asp Leu Phe Lys Glu Leu Leu Glu Glu Leu Lys Gln Lys
1               5                   10                  15

Leu Lys (2) INFORMATION FOR SEQ ID NO: 193:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 193:

Pro Val Leu Asp Leu Phe Arg Glu Leu Leu Glu Glu Leu Lys Gln Lys
1               5                   10                  15

Leu Lys (2) INFORMATION FOR SEQ ID NO: 194:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 194:

Pro Val Leu Glu Leu Phe Arg Glu Leu Leu Glu Glu Leu Lys Gln Lys
1               5                   10                  15

Leu Lys (2) INFORMATION FOR SEQ ID NO: 195:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 195:

Pro Val Leu Glu Leu Phe Lys Glu Leu Leu Glu Glu Leu Lys Gln Lys
1               5                   10                  15

Leu Lys (2) INFORMATION FOR SEQ ID NO: 196:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 196:

Pro Val Leu Asp Leu Phe Arg Glu Leu Leu Glu Glu Leu Lys Asn Lys
 1               5                  10                  15

Leu Lys (2) INFORMATION FOR SEQ ID NO: 197:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 197:

Pro Leu Leu Asp Leu Phe Arg Glu Leu Leu Glu Glu Leu Lys Gln Lys
 1               5                  10                  15

Leu Lys (2) INFORMATION FOR SEQ ID NO: 198:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 198:

Gly Val Leu Asp Leu Phe Arg Glu Leu Leu Glu Glu Leu Lys Gln Lys
 1               5                  10                  15

Leu Lys (2) INFORMATION FOR SEQ ID NO: 199:

(i) SEQUENCE CHARACTERISTICS:
        (A) LENGTH: 18 amino acids

```
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 199:

Pro Val Leu Asp Leu Phe Arg Glu Leu Trp Glu Glu Leu Lys Gln Lys
 1               5                  10                  15

Leu Lys (2) INFORMATION FOR SEQ ID NO: 200:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 200:

Asn Val Leu Asp Leu Phe Arg Glu Leu Leu Glu Glu Leu Lys Gln Lys
 1               5                  10                  15

Leu Lys (2) INFORMATION FOR SEQ ID NO: 201:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 201:

Pro Leu Leu Asp Leu Phe Lys Glu Leu Leu Glu Glu Leu Lys Gln Lys
 1               5                  10                  15

Leu Lys (2) INFORMATION FOR SEQ ID NO: 202:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
```

(A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 202:

Pro Ala Leu Glu Leu Phe Lys Asp Leu Leu Glu Glu Leu Arg Gln Lys
 1               5                  10                  15

Leu Arg (2) INFORMATION FOR SEQ ID NO: 203:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 203:

Ala Val Leu Asp Leu Phe Arg Glu Leu Leu Glu Glu Leu Lys Gln Lys
 1               5                  10                  15

Leu Lys (2) INFORMATION FOR SEQ ID NO: 204:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 204:

Pro Val Leu Asp Phe Phe Arg Glu Leu Leu Glu Glu Leu Lys Gln Lys
 1               5                  10                  15

Leu Lys (2) INFORMATION FOR SEQ ID NO: 205:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 205:

```
Pro Val Leu Asp Leu Phe Arg Glu Trp Leu Glu Glu Leu Lys Gln Lys
1               5                   10                  15

Leu Lys (2) INFORMATION FOR SEQ ID NO: 206:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 206:

Pro Leu Leu Glu Leu Leu Lys Glu Leu Leu Glu Glu Leu Lys Gln Lys
1               5                   10                  15

Leu Lys (2) INFORMATION FOR SEQ ID NO: 207:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 207:

Pro Val Leu Glu Leu Leu Lys Glu Leu Leu Glu Glu Leu Lys Gln Lys
1               5                   10                  15

Leu Lys (2) INFORMATION FOR SEQ ID NO: 208:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 208:

Pro Ala Leu Glu Leu Phe Lys Asp Leu Leu Glu Glu Leu Arg Gln Arg
1               5                   10                  15

Leu Lys (2) INFORMATION FOR SEQ ID NO: 209:
```

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 209:

Pro Val Leu Asp Leu Phe Arg Glu Leu Leu Asn Glu Leu Leu Gln Lys
1               5                   10                  15

Leu Lys (2) INFORMATION FOR SEQ ID NO: 210:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 210:

Pro Val Leu Asp Leu Phe Arg Glu Leu Leu Glu Glu Leu Lys Gln Lys
1               5                   10                  15

Leu Lys (2) INFORMATION FOR SEQ ID NO: 211:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 211:

Pro Val Leu Asp Leu Phe Arg Glu Leu Leu Glu Glu Leu Xaa Gln Xaa
1               5                   10                  15

Leu Xaa (2) INFORMATION FOR SEQ ID NO: 212:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 212:

Pro Val Leu Asp Leu Phe Xaa Glu Leu Leu Glu Glu Leu Xaa Gln Xaa
1               5                   10                  15

Leu Lys (2) INFORMATION FOR SEQ ID NO: 213:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 213:

Pro Ala Leu Glu Leu Phe Lys Asp Leu Leu Glu Glu Phe Arg Gln Arg
1               5                   10                  15
Leu Lys (2) INFORMATION FOR SEQ ID NO: 214:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 214:

Pro Val Leu Asp Leu Phe Arg Glu Leu Leu Glu Glu Leu Lys Gln Lys
1               5                   10                  15
Leu Lys (2) INFORMATION FOR SEQ ID NO: 215:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 215:

Pro Val Leu Asp Leu Phe Arg Glu Leu Leu Glu Glu Trp Lys Gln Lys
1               5                   10                  15
Leu Lys (2) INFORMATION FOR SEQ ID NO: 216:

(i) SEQUENCE CHARACTERISTICS:

(A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 216:

Pro Val Leu Glu Leu Phe Lys Glu Leu Leu Glu Glu Leu Lys Gln Lys
1               5                   10                  15

Leu Lys (2) INFORMATION FOR SEQ ID NO: 217:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 217:

Pro Val Leu Asp Leu Phe Arg Glu Leu Leu Glu Leu Leu Lys Gln Lys
1               5                   10                  15

Leu Lys (2) INFORMATION FOR SEQ ID NO: 218:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 218:

Pro Val Leu Asp Leu Phe Arg Glu Leu Leu Asn Glu Leu Leu Gln Lys
1               5                   10                  15

Leu Lys (2) INFORMATION FOR SEQ ID NO: 219:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 219:

Pro Val Leu Asp Leu Phe Arg Glu Leu Leu Asn Glu Leu Trp Gln Lys
1               5                   10                  15

Leu Lys (2) INFORMATION FOR SEQ ID NO: 220:

(i) SEQUENCE CHARACTERISTICS:
            (A) LENGTH: 18 amino acids (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 220:

Pro Val Leu Asp Leu Phe Arg Glu Leu Leu Glu Glu Leu Gln Lys Lys
1               5                   10                  15

Leu Lys (2) INFORMATION FOR SEQ ID NO: 221:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 221:

Asp Val Leu Asp Leu Phe Arg Glu Leu Leu Glu Glu Leu Lys Gln Lys
1               5                   10                  15

Leu Lys (2) INFORMATION FOR SEQ ID NO: 222:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 222:

Pro Val Leu Asp Ala Phe Arg Glu Leu Leu Glu Ala Leu Leu Gln Leu
1               5                   10                  15

Lys Lys (2) INFORMATION FOR SEQ ID NO: 223:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 223:

Pro Val Leu Asp Ala Phe Arg Glu Leu Leu Glu Ala Leu Ala Gln Leu
1               5                   10                  15

Lys Lys (2) INFORMATION FOR SEQ ID NO: 224:

(i) SEQUENCE CHARACTERISTICS:
        (A) LENGTH: 18 amino acids
        (B) TYPE: amino acid (C) STRANDEDNESS: single
            (D) TOPOLOGY: linear (ii) MOLECULE TYPE: None (xi) SEQUENCE DESCRIPTION: SEQ ID NO: 224:

Pro Val Leu Asp Leu Phe Arg Glu Gly Trp Glu Glu Leu Lys Gln Lys
 1               5                  10                  15

Leu Lys (2) INFORMATION FOR SEQ ID NO: 225:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 225:

Pro Val Leu Asp Ala Phe Arg Glu Leu Ala Glu Ala Leu Ala Gln Leu
 1               5                  10                  15

Lys Lys (2) INFORMATION FOR SEQ ID NO: 226:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 226:

Pro Val Leu Asp Ala Phe Arg Glu Leu Gly Glu Ala Leu Leu Gln Leu
 1               5                  10                  15

Lys Lys (2) INFORMATION FOR SEQ ID NO: 227:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 227:

Pro Val Leu Asp Leu Phe Arg Glu Leu Gly Glu Glu Leu Lys Gln Lys
 1               5                  10                  15

Leu Lys (2) INFORMATION FOR SEQ ID NO: 228:

(i) SEQUENCE CHARACTERISTICS:
            (A) LENGTH: 18 amino acids
            (B) TYPE: amino acid
            (C) STRANDEDNESS: single (D) TOPOLOGY: linear (ii) MOLECULE TYPE: None (ix) FEATURE:
              (A) NAME/KEY: Other
              (B) LOCATION: 1...18
              (D) OTHER INFORMATION: N-terminal acetylated and
                  C-terminal amidated (xi) SEQUENCE DESCRIPTION: SEQ ID NO: 228:

Pro Val Leu Asp Leu Phe Arg Glu Gly Leu Glu Glu Leu Lys Gln Lys
 1               5                  10                  15

Leu Lys (2) INFORMATION FOR SEQ ID NO: 229:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: None (ix) FEATURE:
              (A) NAME/KEY: Other
              (B) LOCATION: 1...18
              (D) OTHER INFORMATION: N-terminal acetylated and
                  C-terminal amidated (xi) SEQUENCE DESCRIPTION: SEQ ID NO: 229:

Pro Val Leu Asp Leu Phe Arg Glu Leu Leu Glu Glu Gly Lys Gln Lys
 1               5                  10                  15

Leu Lys (2) INFORMATION FOR SEQ ID NO: 230:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: None (xi) SEQUENCE DESCRIPTION: SEQ ID NO: 230:

Pro Val Leu Glu Leu Phe Glu Arg Leu Leu Glu Asp Leu Gln Lys Lys
 1               5                  10                  15

Leu Lys (2) INFORMATION FOR SEQ ID NO: 231:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: None (xi) SEQUENCE DESCRIPTION: SEQ ID NO: 231:

Pro Val Leu Asp Leu Phe Arg Glu Leu Leu Glu Lys Leu Glu Gln Lys
 1               5                  10                  15

Leu Lys (2) INFORMATION FOR SEQ ID NO: 232:

(i) SEQUENCE CHARACTERISTICS:
           (A) LENGTH: 18 amino acids
           (B) TYPE: amino acid
           (C) STRANDEDNESS: single
           (D) TOPOLOGY: linear (ii) MOLECULE TYPE: None (ix) FEATURE:
           (A) NAME/KEY: Other
           (B) LOCATION: 1...18
           (D) OTHER INFORMATION: N-terminal acetylated and
               C-terminal amidated (xi) SEQUENCE DESCRIPTION: SEQ ID NO: 232:

Pro Leu Leu Glu Leu Phe Lys Glu Leu Leu Glu Glu Leu Lys Gln Lys
 1               5                  10                  15

Leu Lys (2) INFORMATION FOR SEQ ID NO: 233:

(i) SEQUENCE CHARACTERISTICS:

(xi) SEQUENCE DESCRIPTION: SEQ ID NO: 233:

This sequence is intentionally skipped (2) INFORMATION FOR SEQ ID NO: 234:

(i) SEQUENCE CHARACTERISTICS:

(xi) SEQUENCE DESCRIPTION: SEQ ID NO: 234:

This sequence is intentionally skipped (2) INFORMATION FOR SEQ ID NO: 235:

(i) SEQUENCE CHARACTERISTICS:

(xi) SEQUENCE DESCRIPTION: SEQ ID NO: 235:

This sequence is intentionally skipped (2) INFORMATION FOR SEQ ID NO: 236:

(i) SEQUENCE CHARACTERISTICS:

(xi) SEQUENCE DESCRIPTION: SEQ ID NO: 236:

This sequence is intentionally skipped (2) INFORMATION FOR SEQ ID NO: 237:

(i) SEQUENCE CHARACTERISTICS:
           (A) LENGTH: 18 amino acids
           (B) TYPE: amino acid
           (C) STRANDEDNESS: single
           (D) TOPOLOGY: linear (ii) MOLECULE TYPE: None (xi) SEQUENCE DESCRIPTION: SEQ ID NO: 237:

Leu Asp Asp Leu Leu Gln Lys Trp Ala Glu Ala Phe Asn Gln Leu Leu
 1               5                  10                  15

Lys Lys (2) INFORMATION FOR SEQ ID NO: 238:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 238:

Glu Trp Leu Lys Ala Phe Tyr Glu Lys Val Leu Glu Lys Leu Lys Glu
1               5                   10                  15

Leu Phe (2) INFORMATION FOR SEQ ID NO: 239:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 239:

Glu Trp Leu Glu Ala Phe Tyr Lys Lys Val Leu Glu Lys Leu Lys Glu
1               5                   10                  15

Leu Phe (2) INFORMATION FOR SEQ ID NO: 240:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO: 240:

Asp Trp Leu Lys Ala Phe Tyr Asp Lys Val Ala Glu Lys Leu Lys Glu
1               5                   10                  15

Ala Phe (2) INFORMATION FOR SEQ ID NO: 241:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 241:

Asp Trp Phe Lys Ala Phe Tyr Asp Lys Val Phe Glu Lys Phe Lys Glu
1               5                   10                  15
Phe Phe (2) INFORMATION FOR SEQ ID NO: 242:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 242:

Gly Ile Lys Lys Phe Leu Gly Ser Ile Trp Lys Phe Ile Lys Ala Phe
1               5                   10                  15
Val Gly (2) INFORMATION FOR SEQ ID NO: 243:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 243:

Asp Trp Phe Lys Ala Phe Tyr Asp Lys Val Ala Glu Lys Phe Lys Glu
1               5                   10                  15
Ala Phe (2) INFORMATION FOR SEQ ID NO: 244:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 244:

Asp Trp Leu Lys Ala Phe Tyr Asp Lys Val Ala Glu Lys Leu Lys Glu
1               5                   10                  15
Ala Phe (2) INFORMATION FOR SEQ ID NO: 245:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 245:

Asp Trp Leu Lys Ala Phe Tyr Asp Lys Val Phe Glu Lys Phe Lys Glu
1               5                   10                  15
Phe Phe (2) INFORMATION FOR SEQ ID NO: 246:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 246:

Glu Trp Leu Glu Ala Phe Tyr Lys Lys Val Leu Glu Lys Leu Lys Glu
 1               5                  10                  15
Leu Phe (2) INFORMATION FOR SEQ ID NO: 247:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 247:

Asp Trp Phe Lys Ala Phe Tyr Asp Lys Phe Phe Glu Lys Phe Lys Glu
 1               5                  10                  15
Phe Phe (2) INFORMATION FOR SEQ ID NO: 248:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 248:

Glu Trp Leu Lys Ala Phe Tyr Glu Lys Val Leu Glu Lys Leu Lys Glu
 1               5                  10                  15
Leu Phe (2) INFORMATION FOR SEQ ID NO: 249:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 249:

Glu Trp Leu Lys Ala Glu Tyr Glu Lys Val Glu Glu Lys Leu Lys Glu
 1               5                  10                  15
Leu Phe (2) INFORMATION FOR SEQ ID NO: 250:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 250:

```
Glu Trp Leu Lys Ala Glu Tyr Glu Lys Val Leu Glu Lys Leu Lys Glu
 1               5                  10                  15
Leu Phe
```

(2) INFORMATION FOR SEQ ID NO: 251:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO: 251:

```
Glu Trp Leu Lys Ala Phe Tyr Lys Lys Val Leu Glu Lys Leu Lys Glu
 1               5                  10                  15
Leu Phe
```

(2) INFORMATION FOR SEQ ID NO: 252:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...15
        (D) OTHER INFORMATION: N-terminal acetylated and
            C-terminal amidated (xi) SEQUENCE DESCRIPTION: SEQ ID NO: 252:

```
Pro Val Leu Asp Leu Phe Arg Glu Leu Leu Glu Gln Lys Leu Lys
 1               5                  10                  15
```

(2) INFORMATION FOR SEQ ID NO: 253:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (ix) FEATURE:
            (A) NAME/KEY: Other
            (B) LOCATION: 1...16
            (D) OTHER INFORMATION: N-terminal acetylated and
                C-terminal amidated (xi) SEQUENCE DESCRIPTION: SEQ ID NO: 253:

Pro Val Leu Asp Leu Phe Arg Glu Leu Leu Glu Glu Leu Lys Gln Lys
1               5                   10                  15

(2) INFORMATION FOR SEQ ID NO: 254:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...16
        (D) OTHER INFORMATION: N-terminal acetylated and
            C-terminal amidated (xi) SEQUENCE DESCRIPTION: SEQ ID NO: 254:

Pro Val Leu Asp Leu Phe Arg Glu Leu Leu Glu Lys Leu Lys Gln Lys
1               5                   10                  15

(2) INFORMATION FOR SEQ ID NO: 255:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...15
        (D) OTHER INFORMATION: N-terminal acetylated and
            C-terminal amidated (xi) SEQUENCE DESCRIPTION: SEQ ID NO: 255:

Pro Val Leu Asp Leu Phe Arg Glu Leu Leu Glu Lys Leu Gln Lys
1               5                   10              15

(2) INFORMATION FOR SEQ ID NO: 256:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...16
        (D) OTHER INFORMATION: N-terminal acetylated and
            C-terminal amidated (xi) SEQUENCE DESCRIPTION: SEQ ID NO: 256:

Pro Val Leu Asp Leu Phe Arg Glu Leu Leu Glu Ala Leu Lys Gln Lys
1               5                   10                  15

-continued (2) INFORMATION FOR SEQ ID NO: 257:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: None (ix) FEATURE:
(A) NAME/KEY: Other
(B) LOCATION: 1...16
(D) OTHER INFORMATION: N-terminal acetylated and C-terminal amidated (xi) SEQUENCE DESCRIPTION: SEQ ID NO: 257:

```
Pro Val Leu Asp Leu Phe Glu Asn Leu Leu Glu Arg Leu Lys Gln Lys
1               5                   10                  15
```

(2) INFORMATION FOR SEQ ID NO: 258:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: None (ix) FEATURE:
(A) NAME/KEY: Other
(B) LOCATION: 1...16
(D) OTHER INFORMATION: N-terminal acetylated and C-terminal amidated (xi) SEQUENCE DESCRIPTION: SEQ ID NO: 258:

```
Pro Val Leu Asp Leu Phe Arg Glu Leu Leu Asn Glu Leu Lys Gln Lys
1               5                   10                  15
```